United States Patent [19]

Suzuki et al.

[11] Patent Number: 5,609,563

[45] Date of Patent: Mar. 11, 1997

[54] ENDOSCOPE APPARATUS PROVIDED WITH CURVATURE AND FLUID FLOW CONTROL

[75] Inventors: Akira Suzuki; Hiroki Hibino, both of Hachioji; Yoshikatsu Nagayama, Sagamihara; Motokazu Nakamura, Hachioji, all of Japan

[73] Assignee: Olympus Optical Co., Ltd., Tokyo, Japan

[21] Appl. No.: 309,528

[22] Filed: Sep. 20, 1994

Related U.S. Application Data

[63] Continuation of Ser. No. 990,483, Dec. 11, 1992, abandoned.

[30] Foreign Application Priority Data

| Dec. 12, 1991 | [JP] | Japan | 3-328999 |
| Feb. 24, 1992 | [JP] | Japan | 4-036349 |
| May 21, 1992 | [JP] | Japan | 4-129073 |
| Aug. 5, 1992 | [JP] | Japan | 4-209230 |

[51] Int. Cl.⁶ ............... A61B 1/005; A61B 1/015
[52] U.S. Cl. .......... 600/118; 600/131; 600/167; 600/107; 600/159
[58] Field of Search .............. 128/4–11; 348/65; 600/131, 132, 146, 118, 167, 107

[56] References Cited

U.S. PATENT DOCUMENTS

| 3,806,664 | 1/1970 | Browne et al. | |
| 3,917,917 | 11/1975 | Murata | 200/5 R X |
| 4,566,437 | 1/1986 | Yamaguchi | 128/4 |
| 4,617,915 | 10/1986 | Arakawa | 128/4 |
| 4,924,851 | 5/1990 | Oenier et al. | 128/4 |
| 4,979,497 | 12/1990 | Matura et al. | 128/4 |
| 5,125,394 | 6/1992 | Chatenever et al. | 128/4 |
| 5,159,446 | 10/1992 | Hibino et al. | 358/98 |
| 5,343,855 | 9/1994 | Iida et al. | 128/6 |

OTHER PUBLICATIONS

Patent Abstracts vol. 15, No. 464 (E–1137) & JP–A–31 98 485 (Sanyo Electric Co. Ltd.) Aug. 29, 1991.
Patent Abstract EP–A–0 212 784 (Beltronics Inc.) column 1, line 29–column 2, line 11.

Primary Examiner—Richard J. Apley
Assistant Examiner—John P. Leubecker
Attorney, Agent, or Firm—Armstrong, Westerman, Hattori, McLeland & Naughton

[57] ABSTRACT

In an endoscope, a curvature indicating element for curvature-indicating a curvable curvature section provided adjacent to a distal end of an elongated inserting section having elasticity is arranged at a location close to a thumb of a hand grasped by an operator in the operating section provided at a proximal end portion of an inserting section. An operating element for controlling operation of fluid such as outflow, inflow or the like is arranged at location opposite to the curvature indicating element in the operating section. Thus, operations of the curvature operation, outflow and inflow of the fluid and the like can be executed simultaneously under a condition where the operating section is grasped.

14 Claims, 34 Drawing Sheets

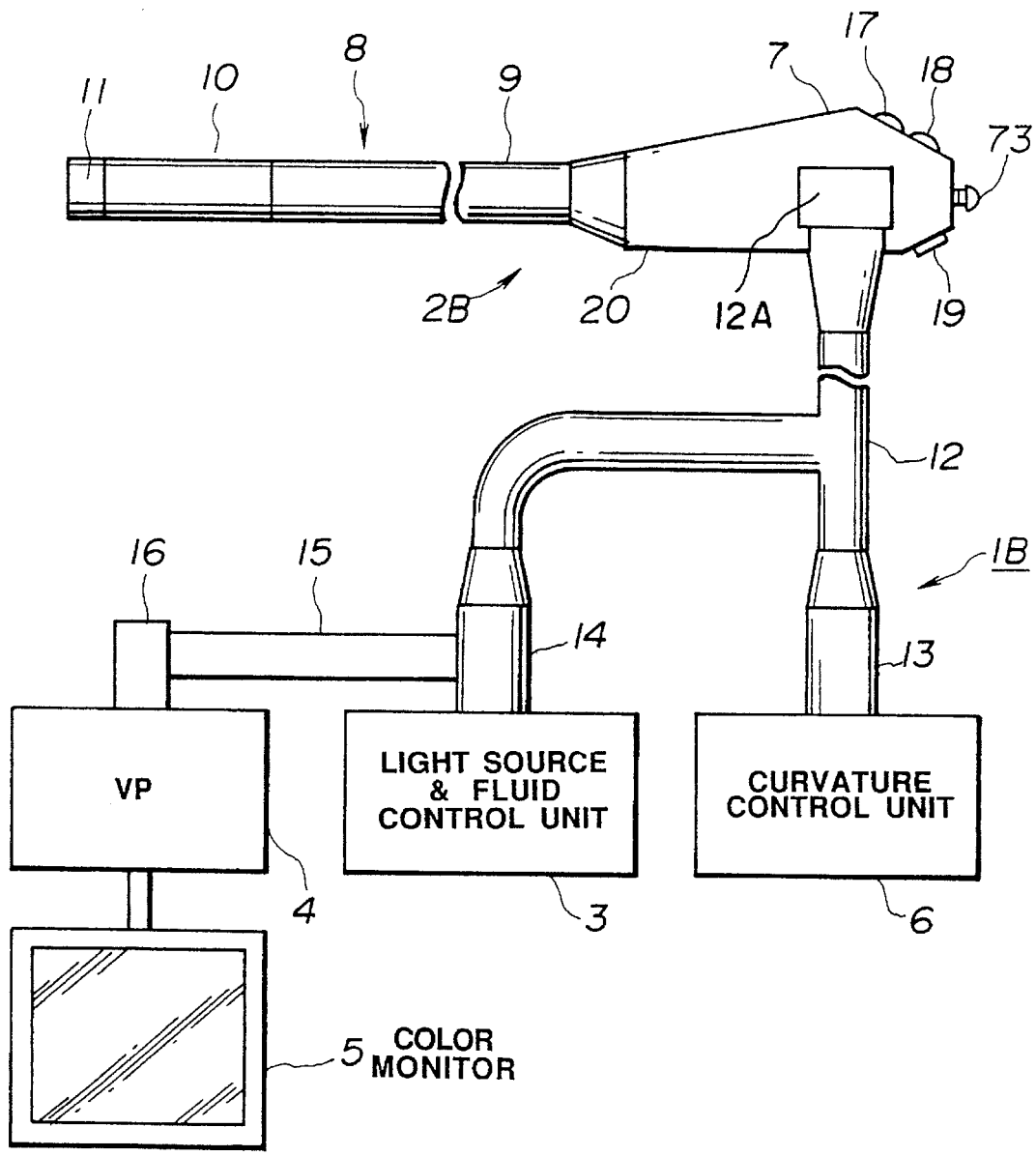

ENDOSCOPE APPARATUS PROVIDED WITH CURVATURE AND FLUID FLOW CONTROL

This application is a continuation of application Ser. No. 07/990,483 filed Dec. 11, 1992, now abandoned.

BACKGROUND OF THE INVENTION

1. Field of the Invention

The present invention relates to an endoscope apparatus having switches arranged at respective positions thereof which allow the switches to be easily operated, such as a switch for controlling a curvature operation.

2. Related Art and Prior Art Statement

In recent years, an endoscope has widely been used in which an elongated inserting section is inserted into a body cavity, whereby internal organs within the body cavity are observed by an objective optical system which forms observing means provided at a forward end portion of the inserting section, or, as the occasion demands, a treatment instrument inserted into a treatment-instrument channel is used for executing various types of medical care treatments.

Further, an industrial endoscope has widely been utilized for observation, inspection and so on of internal wounds or flaws, corrosion or erosion or the like in a boiler, a gas turbine engine, piping of a chemical plant or the like, a body of a vehicle engine, and the like.

Generally, such an endoscope has a curvature mechanism for curving a curvature portion provided in the vicinity of the forward end portion of the inserting section so as to be capable of directing a viewing direction of an objective optical system at the forward end portion of the inserting section toward a direction of an objective part, wherein curvature operating means adjacent to the hand is operated, whereby the curvature portion can be remotely curved through the curvature mechanism.

In a case of a mechanical curvature mechanism, since the curvature mechanism must be driven by manual operation, a considerable capacity or ability is required during operation. For this reason, an endoscope has been known which is provided with an electromotion curvature drive mechanism in which electromotion drive means such as a motor or the like is arranged to electrically drive the curvature mechanism, and the curvature mechanism can be curved by a switch operation requiring almost no power or capacity at hand.

The endoscope having such electromotion curvature drive mechanism is combined with a curvature control device for controlling curvature of the endoscope, a light source device and the like, to form an endoscope apparatus, and has been utilized.

Furthermore, extraneous matter such as body fluid and the like frequently adhere to an outer surface of the objective optical system at the forward end portion of the inserting section, because the endoscope is inserted into a body so that an observing function is reduced. Water-feed and gas-feed mechanisms are arranged as a mechanism for removing the extraneous matters so as to remove or solve the above-discussed problem. A switch or a button adjacent to the hand is operated, whereby cleaning water is jetted toward the outer surface of the objective optical system, to wash away the extraneous matters and, subsequently, a switch or a button for feeding air is operated to blow away and remove droplets of the cleaning water remaining on the outer surface of the objective optical system, so that the outer surface of the objective optical system can be set to a clean condition having no extraneous matters.

Moreover, there is also an endoscope apparatus in which an endoscope is provided with suction means for sucking or drawing and discharging fluid such as body liquid or the like which interferes with observation within the body, and which can control suction operation by a suction switch or button.

There are many cases where the above-described operation switches executing various operations such as curving, air-feeding, water-feeding and suction, are arranged at the operating section connected to a proximal end of the inserting section. There is an endoscope apparatus in which such operations can be executed by a hand which grasps or grips the operation section.

An endoscope apparatus provided with an electromotion curvature drive mechanism, an arrangement in which control means for controlling an operating speed by operating time, a quantity of operation, an operational capacity and the like of the curvature operating switch is incorporated in a curvature control device has been disclosed in, for example, Japanese Patent Laid-Open No. HEI 1-317423, Japanese Patent Laid-Open No. SHO 58-78635, Japanese Patent Publication No. SHO 63-59329 and Japanese Patent Laid-Open No. SHO 58-69523.

A curvature operating switch at a rearward end portion of an operating section is also well-known. In this case, it is difficult to operate the curvature operating switch by a hand which grasps the operating section. Further, there is also a prior art device in which, even if the curvature operating switch can be operated by the hand grasping the operating section, it is difficult to execute operation of gas-feed/water-feed and suction.

Furthermore, in other prior art devices, a curvature switch executing curvature operation and a switch executing gas-feed/water-feed and suction are arranged respectively on surfaces adjacent to each other or adjoining each other. Accordingly, there is room for improvement of operation by the hand which grasps the operating section.

That is, in a case where various kinds of switches are operated under a condition where the operating section is grasped by one hand, at least two fingers are required such as, for example, a case of being grasped by the fifth finger and the third finger, or the like. In this case, fingers capable of being used in operation are three including the thumb, the first finger and the second finger, for example. Accordingly, if curvature operation is executed by the thumb, operations of gas-feed/water-feed and suction are executed by the first finger and the second finger, respectively.

If the curvature switch and the switch executing gas-feed/water-feed and suction are arranged respectively on the surfaces adjoining each other, in a case where the switch for executing gas-feed/water-feed and suction is operated, it is impossible to use the endoscope apparatus because the third finger and the second finger, for example, are grasped. For this reason, grasping capability is reduced so that operation becomes unsteady, increasing the burden in a case where grasping is executed by the fifth finger and the third finger which are used for grasping. Thus, the hand tends to become tired.

Moreover, also even in a case where curvature operation is executed, it is possible to curve the curvature portion in an optional curving direction out of a plurality of curving directions. However, in a case where curvature operation in a specific curving direction out of a plurality of curving directions is used most frequently, it is desirable that an operating position executing curvature operation into the specific curving direction is arranged at a location which lessens fatigue of the finger.

Generally, a curving operation curving upwardly is used most often. In the prior art, however, a position of the switch executing or performing the upward curvature operation is not arranged at a position closest to the thumb (in a case where the operating section is grasped). Accordingly, there is a problem that, if the curvature operation continues, the thumb tends to become tired.

In this manner, in the prior art, the arrangement of various switches at the operating section is not ideal, and there is room for improvement.

Further, there is a case where an electronic endoscope building therein image pickup means has been used in recent years. In this electronic endoscope, there is an arrangement which comprises a freeze switch for freezing an image displayed on a monitor to create a still picture, a release switch for indicating operation for recording an image by a recording device, or the like. Accordingly, if the number of switches increases, the number of operations of the switches increases. Thus, it is desirable to appropriately arrange the switches.

SUMMARY OF THE INVENTION

It is an object of the invention to provide an endoscope capable of improving operability such as the curvature operation, operation of gas-feed/water-feed and the like, in consideration of human engineering or biotechnology.

It is another object of the invention to provide an endoscope in which, even if curvature operation continues, the operator fatigue is lessened.

According to the invention, there is provided an endoscope in which a curvature direction indicating element for indicating the curvature of the curvature section provided adjacent to a distal end of an elongated inserting section having elasticity is arranged at a position closer to a thumb of a hand grasped by an operator at an operating section which is arranged at a proximal end portion of the inserting section, wherein an operating element for controlling an operation such as outflow and inflow of fluid and the like is arranged at a location opposite the curvature direction indicating element at the operating section, and wherein both the curvature operation and an operation such as outflow and inflow of the fluid or the like can be executed simultaneously when the operating section is grasped by the hand of an operator, improving operability.

Furthermore, the curving direction indicating element is arranged such that an upward-direction curvature indicating element for upwardly curving an upward-direction curvature indicating element for upwardly curving a curvature section which is used most often is arranged at a location closest to the thumb of the hand grasped by an operator so that even if the curving operation is executed continuously, fatigue can be reduced or can decrease.

BRIEF DESCRIPTION OF THE DRAWINGS

FIG. 2 is a cross-sectional view showing the curvature operation switch;

FIG. 3 is an electric block diagram and a curvature mechanism except for a fluid control system of an endoscope apparatus;

FIG. 4 is a view showing an entire arrangement of the endoscope apparatus;

FIG. 5 is a view showing an arrangement of the endoscope and a light-source and fluid control device;

FIG. 6 is a perspective view showing a case where an operating section is grasped by a right hand;

FIGS. 8 to 10 relate to a second embodiment of the invention. FIG. 8 being a view for description, showing an arrangement of a curvature switch, a selecting or changeover switch and the like at an operating section of an endoscope;

FIG. 9 is a view showing an entire arrangement of an endoscope apparatus;

FIG. 10 is an electric block diagram and a curvature mechanism except for a fluid control system of the endoscope apparatus;

FIG. 12 is a view for description, showing a curvature mechanism;

FIG. 13 is a cross-sectional view showing a curvature operating switch;

FIG. 14 is a view showing an outer appearance of a two-stage ON-OFF switch;

FIG. 15 is a cross-sectional view taken along a line I—I in FIG. 14;

FIG. 16 is a view for connection, showing a circuit arrangement of the two-stage ON-OFF switch;

FIG. 17 is a view for description, showing a circuit arrangement of a curvature operating control system;

FIG. 19 is a view for description, showing a circuit arrangement of a curvature operating control system;

FIG. 20 is a view for description, showing a relationship between an ON-OFF condition of a two-stage ON-OFF switch and motor driving current;

FIG. 22 is a view as viewed from a line II—II in FIG. 21;

FIG. 23 is a view for description, showing a circuit arrangement of a curvature operating control system;

FIG. 25 is a perspective view showing an operating section formed with operating means such as a curvature switch or the like;

FIG. 26 is an arrangement view showing a curvature drive mechanism within the operating section;

FIG. 27 is a perspective view showing a chain aid in FIG. 26;

FIG. 28 is an enlarged cross-sectional view taken along a line A—A in FIG. 26;

FIG. 29 is a connection view showing an arrangement of a control system such as a curvature switch, a gas-feed/water-feed switch and the like;

FIG. 30 is a view for description, showing a water tank;

FIG. 32 is a connection view showing an arrangement of a control system such as the curvature switch, a gas-feed/water-feed switch and the like in the seventh embodiment of the invention;

FIG. 34 is a connection view showing an arrangement of a control system such as the curvature switch, a gas-feed/water-feed switch or the like in the eighth embodiment of the invention;

FIG. 36 is a connection view showing an arrangement of a control system such as a curvature switch, freeze switch and the like in the ninth embodiment of the invention;

FIG. 38 is a perspective view showing a forceps raising-up switch formed by a seesaw switch provided on an operating section;

FIG. 39 is a perspective view showing a forceps raising-up mechanism formed on a forward-end arrangement portion;

FIG. 40 is a connection view showing a mechanism of a control system such as a curvature switch, the forceps raising-up switch and the like;

FIG. 42 is a perspective view showing a zoom switch formed by a seesaw switch provided at an operating section;

FIG. 43 is a view showing, under a WIDE condition, an objective lens system provided with a zoom lens mechanism formed on a forward-end arrangement portion;

FIG. 44 is a view showing, under a TELE condition, the objective lens system provided with the zoom lens mechanism formed on the forward-end arrangement portion;

FIG. 45 is a connection view showing an arrangement of a control system such as a curvature switch, a zoom switch or the like in the eleventh embodiment of the invention;

FIG. 47 is a connection view showing an arrangement of a control system such as a curvature switch, a zoom switch or the like in the twelfth embodiment of the invention.

DETAILED DESCRIPTION OF THE PREFERRED EMBODIMENTS

Various embodiments of the invention will hereunder be described with reference to the accompanying drawings. A first embodiment of the invention will first be described with reference to FIGS. 1 to 6.

Figure 4:
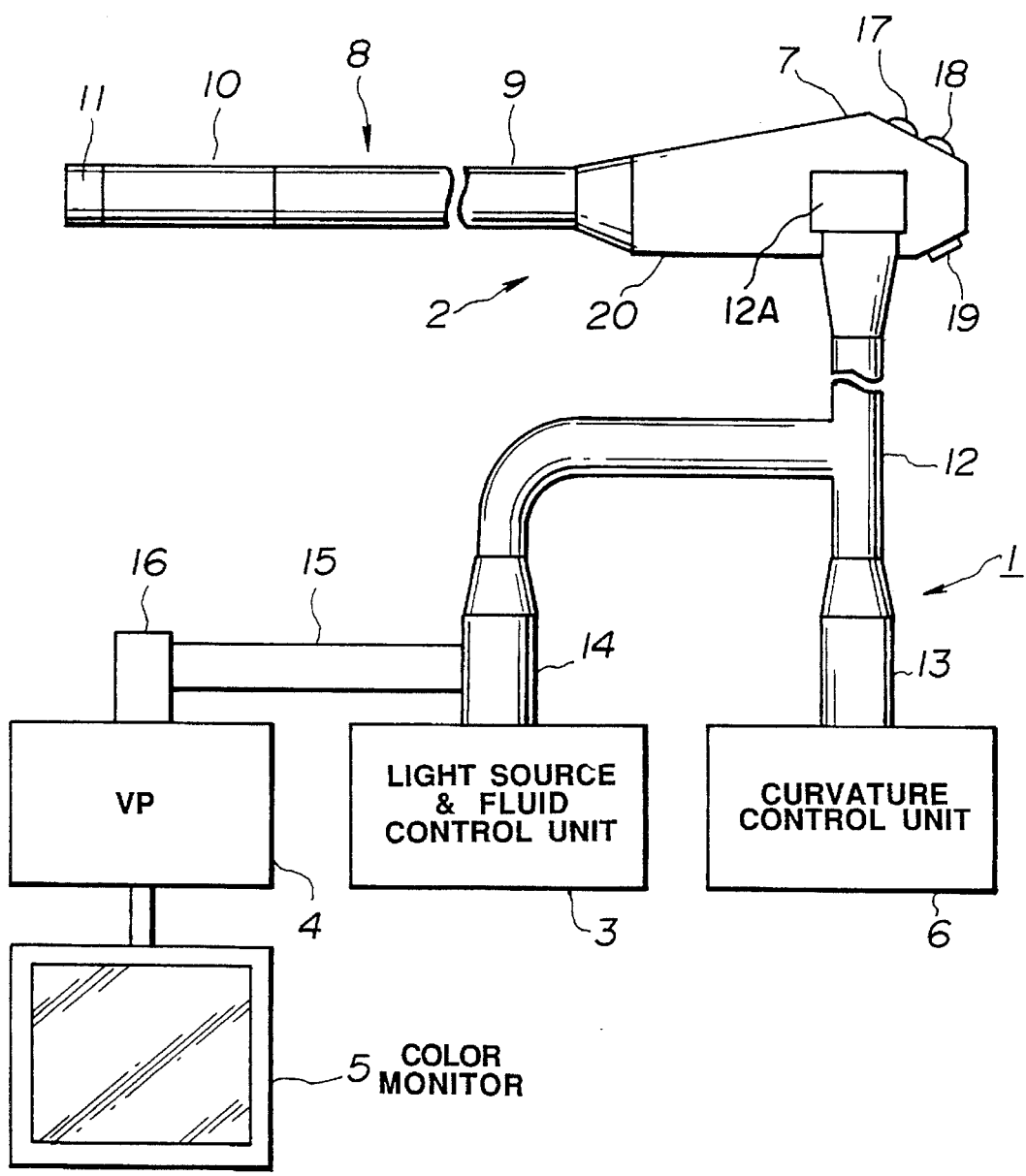
Figure 5:
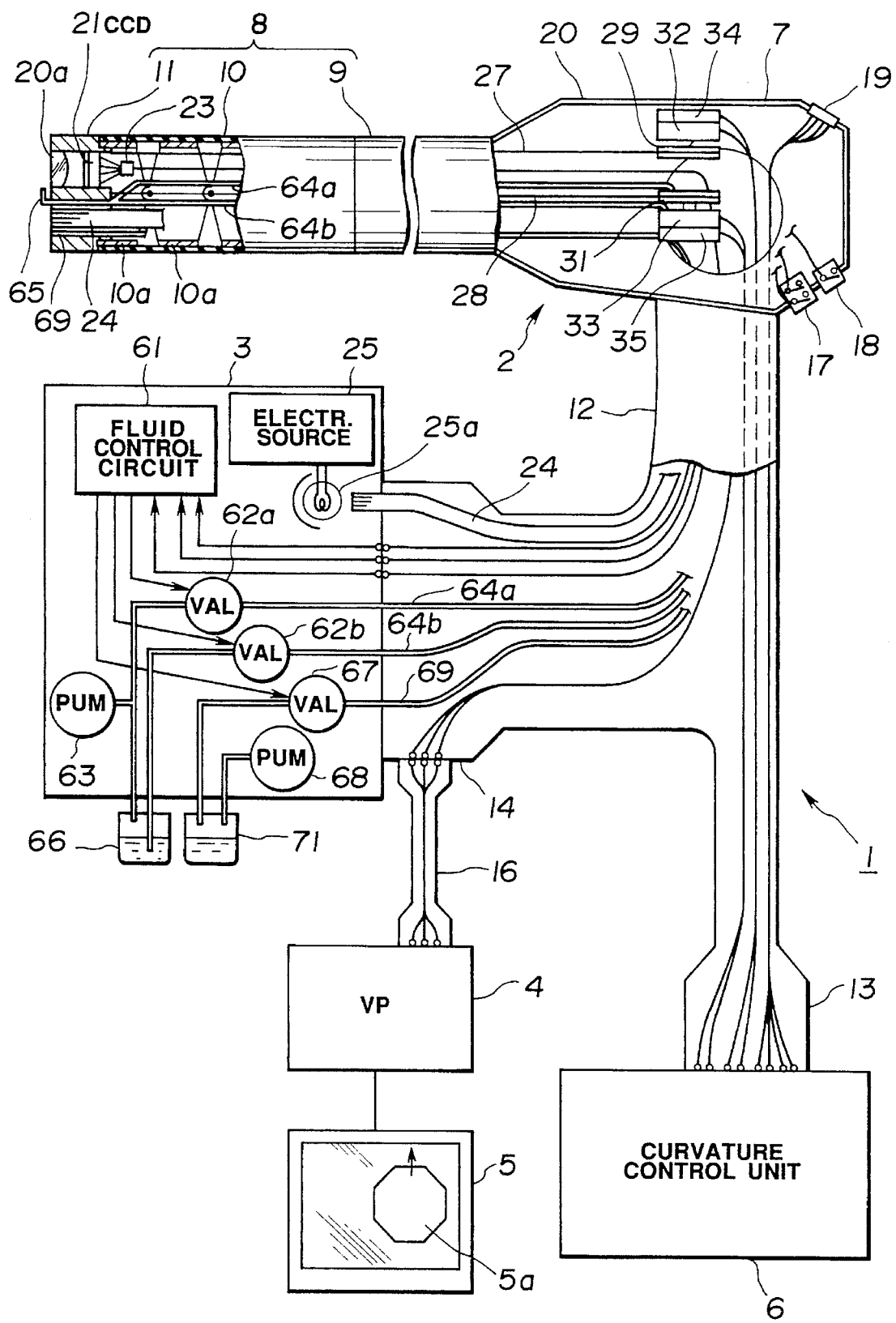

An endoscope apparatus 1 provided with the first embodiment of the invention illustrated in FIGS. 4 and 5 comprises an electronic endoscope 2 provided therein with a solid-state image pickup element such as a CCD 21, a light-source and fluid control device 3 for supplying an illuminating light to an illuminating-light transmitting element of the electronic endoscope 2 and for controlling outflow/inflow operation of fluid through lines of the electronic endoscope 2, a video processor (hereinafter referred simply to as "VP") 4 for driving a CCD to be described later, to convert an image pickup signal from the CCD to an image signal, a color monitor 5 for representing or projecting an image signal from the VP 4, and a curvature-motor control device 6 for controlling the curvature of a curving section 10 of the electronic endoscope 2.

The electronic endoscope 2 comprises an operating section 7 great in width provided with a plurality of operating switches for executing operations such as curvature, and an inserting section 8 connected to a front part of the inserting section 7 and formed in an elongated manner so as to be capable of being inserted into a subject. Connected to the inserting section 8 are a flexible tube portion 9, the curvable curvature portion 10 and a hard forward-end arrangement portion 11 in order from the side of the operating section 7.

The curvature section 10 is arranged such that a plurality of curvature pieces 10a, 10a, . . . are connected to each other by rivets or the like for angular movement so that the curvature section 10 is curvable in upper and lower and left- and right- hand directions, i.e., vertical and lateral directions. In FIG. 5, an arrangement is shown in which the curvature pieces are connected to each other in a vertical direction for angular movement, for example, for simplification.

The operating section 7 has a grasping portion 20 held when the operator grasps the endoscope to execute insertion/removal, curvature operation and the like, and formed adjacent to the inserting section 8, and a switch box 7a formed at a rearward end of the grasping portion 20 and provided with a plurality of operating switches.

The operating section 7 having the grasping portion 20 and the switch box 7a is substantially square and tubular in configuration. A universal cable 12 which branches into two sections extends from a position adjacent to a projection 12A at a rearward end of one of the side surfaces of the operating section 7 (under a condition of grasping the grasping portion 20, a setting is made such that a portion adjacent to the switch box 7a is normally brought to an upper side and, accordingly, there is also a case where an upper portion is used in place of the rearward end).

The universal cable 12 has one end thereof provided with a connector 13 for a motor control device detachably connected to the curvature motor control device 6, and the other end provided with a light guide connector 14 which is detachably connected to the light source device 3.

A video control cable 15 extends from a side of the light guide connector 14. The video control cable 15 has an end thereof provided with a video-processor (VP) connector 16 detachably connected to the VP 4.

Figure 1:
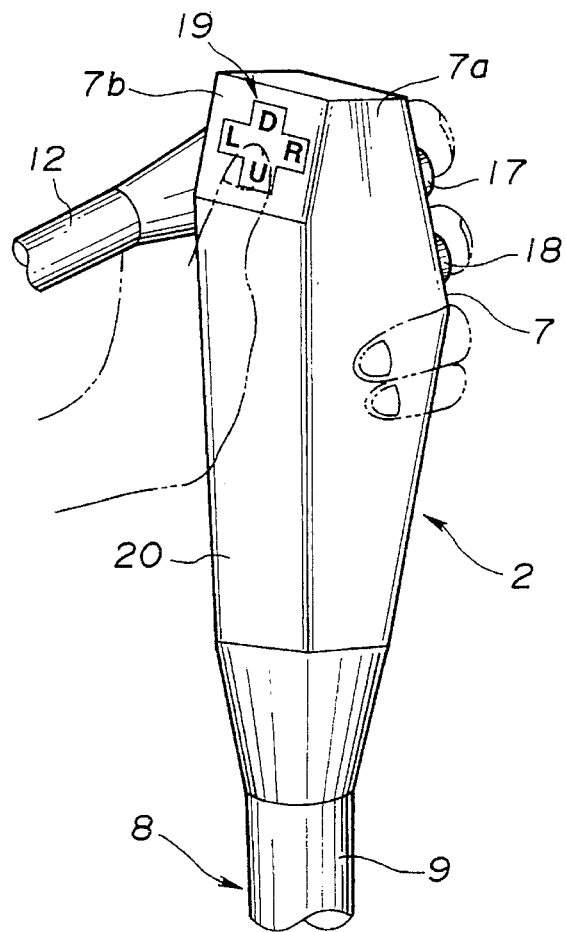
FIGS. 1 to 6 relate to a first embodiment of the invention, FIG. 1 being a view for description, showing an arrangement and an operational example of a curvature switch and the like in an operating section of an endoscope.

Moreover, as shown in FIG. 1, the switch box 7a provided at an upper portion of the grasping portion 20 in the operating section 7 is formed with a curvature operating switch portion 19 which executes curvature operation with respect to one of two substantially opposed surfaces. A gas-feed/water-feed switch 17 and a suction switch 18 are provided on the other surface which is brought to the side of a rear surface with respect to the aforesaid surface.

The gas-feed/water-feed switch 17 is an operating element for controlling operation of gas-feed/water-feed which is provided for cleaning an outer surface of an observing window provided in a front surface of the forward-end arrangement portion 11. The suction switch 18 is an operating element for controlling suction movement or operation for sucking body liquid or the like.

As shown in FIG. 5, the gas-feed/water-feed switch 17 is connected to a fluid control circuit 61 within the light source and fluid control device 3 by a signal line through the universal cable 12. The gas-feed/water-feed switch 17 is formed by a two-stage switch which is turned OFF and ON in a two-stage manner. A small amount of depression turns ON a first switch portion, while a greater amount of depression turns ON also a second switch. The gas-feed/water-feed switch 17 is brought to a toggle switch which is turned OFF in a case of being next operated. When the first switch is turned ON, the fluid control circuit 61 executes gas feed operation, while, when the first and second switches are turned ON, water feed operation is executed.

For example, when operation is executed to turn ON the first switch which functions as a gas feed switch, the fluid control device 61 opens a gas feed valve 62a, to feed gas due to a gas-feed/water-feed pump 63 toward the forward end of the inserting section 8 through a gas feed line 64a, to thereby jet the gas from a gas-feed/water-feed nozzle 65.

Moreover, if an even greater amount of depression turns ON also the second switch, the fluid control circuit 61 closes the gas feed valve 62a, and opens a water feed valve 62b, to feed the gas due to the gas-feed/water-feed pump 63 to a water feed tank 66, to thereby raise the pressure of gas within the water feed tank 66.

The compressed gas feeds the cleaning water within the water feed tank 66 toward the forward end of the inserting section 8 through a water feed line 64b. The cleaning water is jetted through the gas-feed/water-feed nozzle 65 which is formed at the forward end of a common line which joins the gas feed line 64a.

An objective lens 20a is arranged so as to be opposed against an outlet of the gas-feed/water-feed nozzle 65. It is possible to remove extraneous matter adhering to the outer surface of the objective lens 20a by the gas or fluid jetted through the gas-feed/water-feed nozzle 65.

Furthermore, the suction switch 18 is connected to the fluid control circuit 61 within the light source and fluid control device 3 by a signal line through the universal cable 12. Operation of the suction switch 18 causes the fluid control circuit 61 to open a suction valve 67, causing a suction pump to suck the fluid through a suction line 69. The suction line 69 opens at the forward end portion of the inserting section 8. The suction line 69 sucks body fluid through the opening of the suction line 69, and receives the fluid sucked in a waste-liquid container 71 which is interposed at a location short of the suction pump 68.

Figure 3:
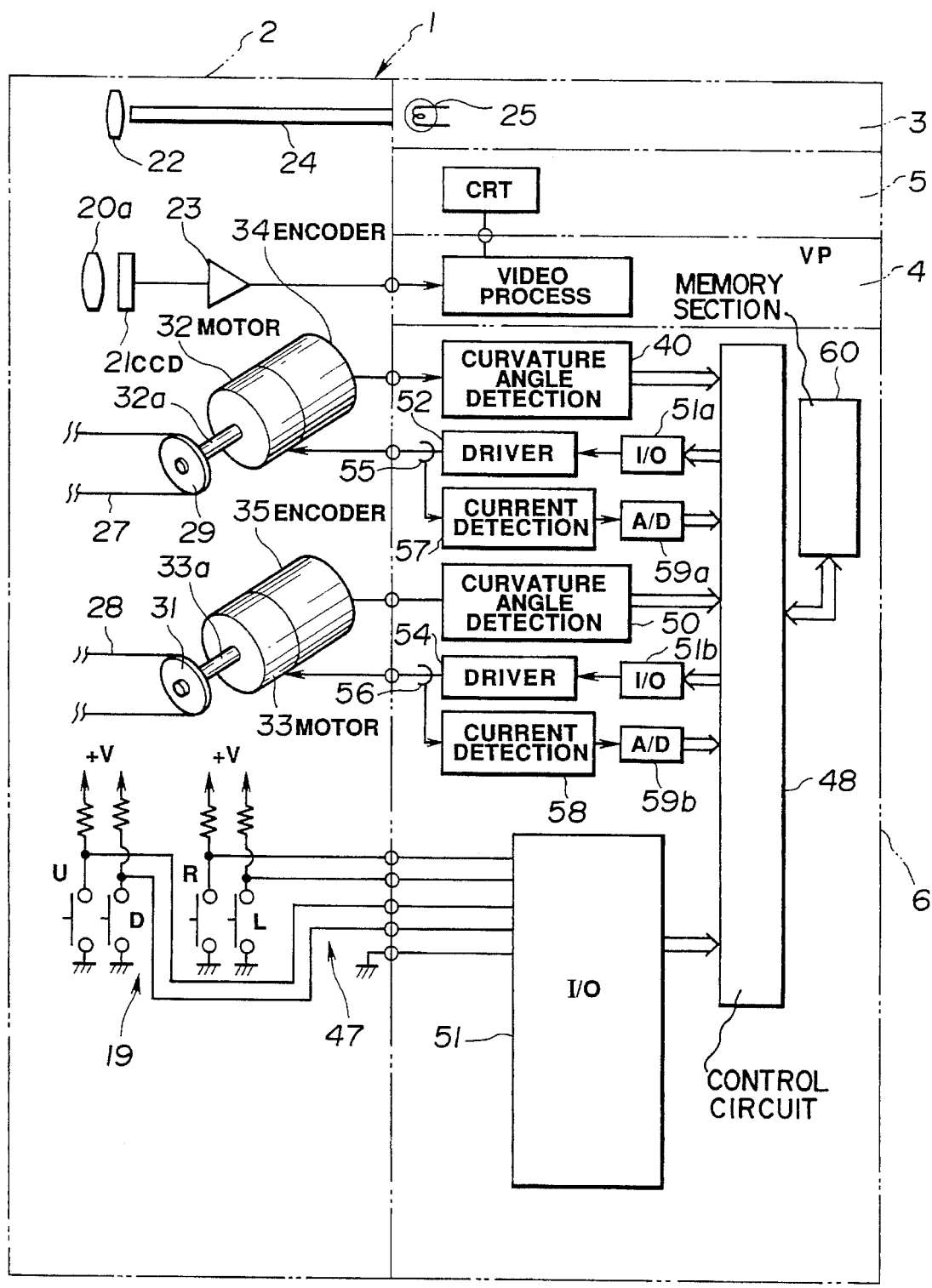

Further, a curvature operating switch portion 19 formed as operating means for executing a command of curvature indication or instruction on a surface substantially opposed against the surface which is formed with the gas-feed/water-feed switch 17 and the suction switch 18 in the switch box 7a of the operating section 7 is formed by four cruciform switches including an upper curvature switch U, a lower curvature switch D, a leftward curvature switch L, and a rightward curvature switch R, such that indication of curving the curvature section 10 in four directions, including upper-lower-leftward-rightward directions, can be issued, as shown in FIGS. 1 and 3.

The curvature operating switch portion 19 is provided at an upper side (that is, the side opposite to the inserting section 8) of the grasping portion 20 grasped by the operator. When the grasping portion 20 is grasped by the operator, the curvature operating switch portion 19 is located adjacent to a thumb of a hand of the operator. Operation of the curvature operating switch portion 19 can be arranged to be executed by the thumb.

Moreover, a surface on which the curvature operating switch portion 19 is formed is brought to an inclined surface 7b which is inclined from a surface of the grasping portion 20. That is, the inclined surface 7b is inclined such that an upper side of the inclined surface 7b is inclined in a direction spaced away from the thumb of the hand of the operator (that is, in a forward direction of the operator). Accordingly, in a case where the curvature operating switch portion 19 is operated by the fingers, the operator is more likely to be able to confirm the condition than in a case where the surface on which the curvature operating switch portion 19 is formed is not brought to the inclined surface 7b.

Furthermore, the universal cable 12 through which the light guide is inserted extends to the outside at a location adjacent to the curvature operating switch portion 19, at a surface adjacent to the inclined surface portion 7b provided with the curvature operating switch portion 19. That is, the curvature operating switch portion 19 is arranged at a location adjacent to the base portion of the universal cable 12.

Figure 6:
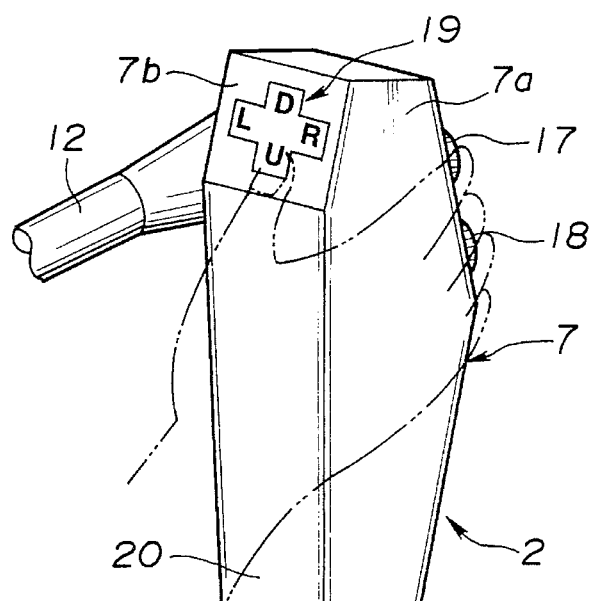

Here, generally, there are many cases where various kinds of operations such as insertion/removal, and curvature operation are executed under a condition where the endoscope is grasped so that the operating section 7 is located short of the operator. In this case, the endoscope is normally grasped by the left hand, and the upward direction of the operating section 7 faces downwardly as shown in FIG. 1 such that the inserting section 8 faces downwardly vertically as shown in FIG. 1 (the endoscope is grasped by a right hand for a left-handed person, as shown in FIG. 6).

Accordingly, in the present embodiments, in a case where the curvature operating switch portion 19 is such that the inserting section 8 faces vertically downward as shown in FIG. 1, the curvature operating switch portion 19 is arranged on the side of the upper portion of the operating section 7 and on a surface of the operating section 7 grasped which is opposed against the operator.

Moreover, as shown in FIG. 1, the four switches U, D, L and R of the curvature operating switch portion 19 are such that the upward curvature switch U is located adjacent to the grasping portion 20, the downward curvature switch D is located on the remote side away from the grasping portion 20, the left-hand curvature switch L is located on the side where the universal cable 12 projects, and the right-hand curvature switch R is located at the side opposite the projecting side.

These directions take measures against the directions preset or predetermined in an observing field of view on the basis of the objective lens 20a. In the first embodiment, a direction which is set as being an upward direction (lower side in FIG. 5, for example) of the observing field of view on the basis of the objective lens 20a (a photoelectric conversion surface in front of the CCD 21 in FIG. 5) is brought to an upward side in a case where the endoscope image 5a is displayed on the screen of the monitor 5 through the CCD 21. When the upward curving switch U is operated, it is possible to change the observing field of view to an upward direction as indicated by an arrow. Other directions are also set similarly.

Figure 2:
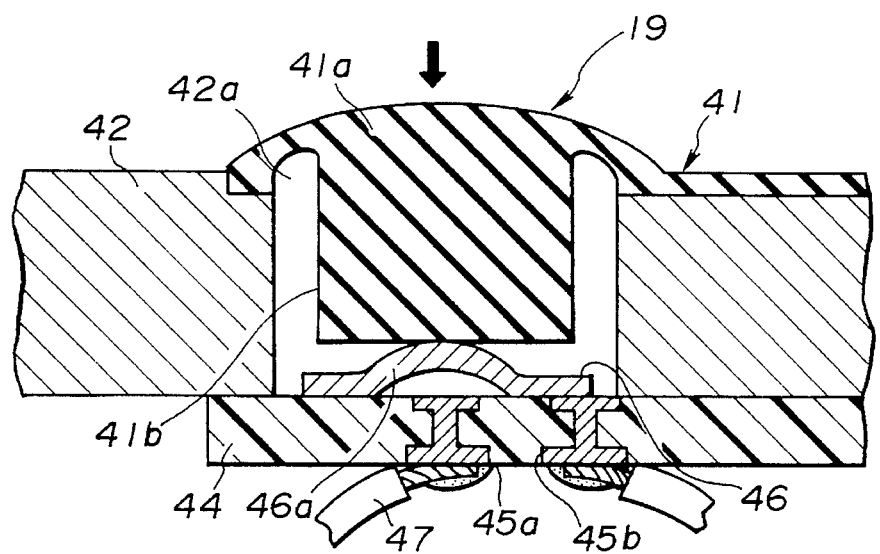

A structure of the curvature operating switch portion 19 will be described by the use of FIG. 2. In this connection, FIG. 2 is a cross-sectional view of only one of four switches. The four switches are the same in arrangement as each other, and the detailed description of the other three switches will be omitted.

The curvature operating switch portion 19 has a surface thereof which is covered with a cover 41 which is made of soft elastomers. The cover 41 has a projection 41a whose tip is located at each of the centers of the respective switches to integrally cover the four switches. Further, the cover 41 is water-tightly adhered to a casing 42 of the operating section 7. A tubular or columnar element 41b is provided in projection below the projection 41a of the cover 41, and is received in a through bore 42a provided in the casing 42. A substrate 44 in which an electric wiring pattern is arranged is fixed at a location below the casing 42. A switch contact 45a and a switch contact 45b are formed on the substrate 44 in a spaced relation to each other in a through-hole pattern.

A leaf spring 46 having a circular projection 46a at its center is arranged between the columnar element 41b and the substrate 44. The leaf spring 46 has one end thereof which is in contact with the switch contact 45b, while the switch contact 45a is located in a direction just below (in the figure) the projection 46a of the leaf spring 46. Furthermore, a pair of signal lines 47, 47 are connected respectively to the switch contacts 45a and 45b. These signal lines 47, 47 are connected to the curvature motor control device 6 through the universal cable 12.

When the projection 41a of the cover 41 is depressed, the columnar element 41b depresses the leaf spring 46. The projection 46a of the leaf spring 46 is then deformed. Thus, the switch contact 45a and the switch contact 45b are in contact with each other.

In connection with the above, the curvature operating switch portion 19 may be of a joy-stick type, not of a flat type. The four-direction switch may be separated into four. Moreover, the curvature operating switch portion 19 may be an upward and downward two-directional switch, not the four-directional switch.

A light guide fiber 24 consisting of a fiber bundle is inserted into the inserting section 8 and the universal cable 12. An illuminating light from an illuminating lamp 25a is incident upon the end surface adjacent to the connector 14. The illuminating lamp 25a is supplied with electric power for radiating the illuminating lamp 25a from a power source 25.

The illuminating light incident upon the end surface adjacent to the connector 14 is transmitted by the light guide fiber 24, and goes out toward a location in front of the forward end portion 11 from the other end surface mounted on the illuminating window at the forward end portion 11, to illuminate a location adjacent to an object (not shown).

The illuminated location adjacent to the object focuses an optical image on a focal surface by the objective lens 20a which is mounted on the observing window in the forward end portion 11. The CCD 21 having a function of photoelectric transferring is arranged on the focal surface, and cooperates with the objective lens 20a to form an image pickup means.

A signal cable is electrically connected to the CCD 21. The signal cable reaches the VP connector 16 through an amplifier 23. The connector 16 is connected to a signal processing circuit within the video processor 4. A standard image signal is generated by the signal processing circuit. An image of the object is displayed in color by the monitor 5.

The curving section 10 is provided therewithin, at a location adjacent to the rearward end of the forward end portion 11, with a curvature tube in which the plurality of curvature pieces 10a, 10a, . . . are formed in a longitudinal connection row vertically and laterally for angular movement within the curving section 10. A vertical curvature operating wire 27 and a lateral curvature operating wire 28 are inserted in the plurality of curvature pieces 10a, 10a, . . . . A forward end of each of the wires is fixed to a forward end element forming the forward end portion 11 or to the most forward curvature piece 10a. These curvature operating wires 27 and 28 are inserted into the curvature portion 10 and the flexible tube portion 9, and have respective rearward ends thereof which are wound about pulleys 29 and 31 within the operating section 7.

The pulleys 29 and 31 are fixedly mounted respectively on shafts 32a and 33a of respective DC motors 32 and 33, for example, which serve as electric curvature drive means. The pulleys 29 and 31 are also rotated by rotation of these DC motors 32 and 33.

In a case where the curvature section 10 is curved vertically, the motor 32 is driven. By rotation of the pulley 29, the curvature operating wire 27 is such that one of folded-back portions is pulled or drawn, while the other folded-back portion is slackened. The curvature section 10 is curved toward the pulled wire.

Further, in a case where the curvature section 10 is curved in a lateral direction, the motor 33 is driven. By rotation of the pulley 31, the curvature operating wire 28 is such that one of folded-back portions is pulled, while the other folded-back is slackened. The curvature section 10 is curved toward the pulled wire.

In the curvature driving DC motors 32 and 33, the pair of shafts 32a and 33a project toward a side opposite to the pulleys 29 and 31. A pair of rotary encoders 34 and 35 are mounted respectively on the shafts 32a and 33a so as to be capable of detecting quantities of rotation of the respective DC motors 32 and 33.

The switch of the curvature operating switch portion 19 is depressed so as to be turned "ON", to thereby drive the DC motors 32 and 33. At this time, by rotary encoders 34 and 35, quantities of rotation of the respective DC motors 32 and 33 are detected.

As shown in FIG. 3, the quantities of rotation detected by the DC motors 32 and 33 are inputted respectively into curvature-angle detecting circuits 40 and 50. The quantities of rotation correspond to the quantity of curvature of the curvature section 10. Accordingly, the curvature-angle detecting circuits 40 and 50 are converted to curvature-angle data of the curvature section 10 by the inputted quantity of rotation, and are inputted to a control circuit 48.

The upper and lower curvature switches U and D and the leftward and rightward curvature switches L and R input ON/OFF signals to the control circuit 48 through an input/output interface (hereinafter referred simply to as "I/O") 51 within the curvature motor control device 6. Contacts of the respective switches U, D, L and R adjacent to the I/O 51 are pulled up to the electric power source ends by resistors through a signal line 47, respectively. Other contacts of the respective switches U, D, L and R are grounded. The switches U, D, L and R output ON-signals of "L", respectively, at turning-ON of the switches.

The control circuit 48 executes control of normal and reverse rotation of the motor 32, that is, control of upper and lower curvature, through an I/O 51a and a driver 52, while the control circuit 48 executes control of normal and reverse rotation of the motor 33, that is, leftward and rightward curvature through an I/O 51b and a driver 54. Drive current for driving the motors 32 and 33 is detected by current detecting circuits 57 and 58 through current probes 55 and 56, and is outputted to the control circuit 48 through an A/D converter 59.

By control of the control circuit 48, the driver 52 supplies positive electric power, for example, in a case of upward curvature, and negative electric power, for example, in a case of downward curvature, with respect to the motor 32. The supplied electric power is converted to current through the current probe 55 by the current detecting circuit 57 and is A/D-converted and, subsequently, is outputted to the control circuit 48. Furthermore, by control of the control circuit 48, the driver 54 supplies positive electric power, for example, in a case of leftward curvature, and negative electric power, for example, in a case of right-hand curvature, with respect to the motor 33. The supplied electric power is converted to current through the current probe 56 by the current detecting circuit 58 and is A/D-converted, subsequently, is outputted to the control circuit 48.

On the other hand, a function is stored in a memory section 60 as a relationship between detected data of the curvature-angle detecting circuit 40 (50) and the current detecting circuit 57 (58). In a case where there is spacing more than 50%, for example, between the detected data of the curvature-angle detecting circuit 40 (or 50) and the current detecting circuit 57 (or 58) with respect to the function stored in the memory section 60, the control circuit 48 slows down an increasing rate of current supply to the driver 52 (or 54), thereby slowing the curvature rate of the curvature section 10.

In the embodiment, the curvature angle of the curvature section 10 is detected by the control circuit 48 through the curvature-angle detecting circuits 40 and 50, while a contact condition between the curvature section 10 and a subject is detected as a consumed electric power by the current detecting circuits 57 and 58. At a predetermined curvature angle, consumed currents (or consumed electric power) of the respective motors 32 and 33 at the time the curvature section 10 is not in contact with the subject (at the time an unrequired or unnecessary load is not applied) are brought to a decided predetermined value.

On the contrary, when curvature is intended to be further applied to the curvature section 10 under a condition that the curvature section 10 is in contact with, for example, a mucous membrane of the subject, curvature is applied contrary to a reaction force from the mucous membrane. Accordingly, as compared with time the curvature section 10 is not in contact with the mucous membrane, current required to produce the same curvature angle increases. A case in which the current increases more than a current value at non-contact in a certain curvature angle by a value equal to or more than a predetermined value indicates that the reaction force from the mucous membrane is considerably high. Accordingly, inadvertent curvature more than this is dangerous. In the present embodiment, assuming that a predetermined value that is a ratio between a current value at non-contact at a certain curvature angle and a current value at contact at the same curvature angle is 50%, for example, data are stored in the memory section 60, and a value equal to or more than this predetermined value is brought to a dangerous level.

In view of the above, the endoscope apparatus 1 controls the motors 32 and 33 such that an increasing rate of the current supply to the motors 32 and 33 slows down, in a case where the state of affairs or circumstances occur that a predetermined value is brought to a value equal to or larger than 50%, whereby movement of the curvature section 10 can become slow. Thus, improvement of the curvature operability and safety of a patient are secured.

For example, in a case where the endoscope is inserted by a method in which a curvature resistance cannot be but increases, such as a well-known FOOKING THE FOLD method, the dangerous level is set relatively high. In a case where a thin tubular cavity organ is desired to pass, the dangerous level is set low so that it is possible to ensure safety and reliability.

As shown in FIG. 1 or FIG. 6, in the present embodiment, the curvature operating switch section 19 is arranged so that operation of the curvature operating switch section 19 can be executed by a thumb of a hand of an operator when the operator grasps the grasping portion 20. The upward curvature switch U of the curvature operating switch portion 19, which is normally the most in curvature frequency, is arranged at a side which is the closest to the thumb of the grasping hand, and the upward curvature switch U is arranged at a position which is the easiest in operation of the upward curvature switch U.

There are many cases where the operator has the upward curvature switch U such that the inserting section 8 is located at a vertically lower position with the operating section 7 located this side. Accordingly, in a case where upward curvature is applied, it is possible to depress the upward curvature switch U without extension of the thumb. Accordingly, the operator feels less fatigue even in a case where upward curvature which is used most often, is applied. For this reason, even in a case where the curvature operation continues, it is possible to continue inspection without undue fatigue, because operation of the upward curvature is used most often.

Further, since the surface on which the curvature operating switch section 19 is arranged is brought to the inclined surface 7b which is inclined with respect to the surface (which extends in the longitudinal direction of the inserting section 8) of the grasping portion 20, operation is executed more easily than a case of being not inclined (in a case where the curvature operating switch section 19 is provided on a surface which is formed by extension of the grasping portion 20).

Furthermore, since the gas-feed/water-feed switch 17 and the suction switch 18 are formed on a surface which is opposite to the surface on which the curvature switch section 19 is formed, it is possible to execute ON/OFF operation by such operation that the gas-feed/water-feed switch 17 and the suction switch 18 are depressed by distal ends including the first finger and the third finger (the tips of fingers) as shown in FIG. 1 or 6. In a case also of being turned OFF, since portions except for the tips of fingers are in contact with a portion of the switch box 7a under such a condition approximate to grasping, stability of the operating section 7 under a grasped condition increases. For this reason, there is no case where the operating section 7 has a switch operation which is executed in an unsure manner. Thus, the switch operation is easy and simple.

In connection with the above, the curvature driving may depend upon hydraulic pressure and SMA, rather than upon the motor. The curvature driving can be applied also to an industrial endoscope, not only to the medical endoscope.

According to the electronic endoscope 2 of the present embodiment, it is possible to make easy the curvature operation, by arrangement of curvature indicating input means, while taking ergonomics into consideration.

Figure 7:
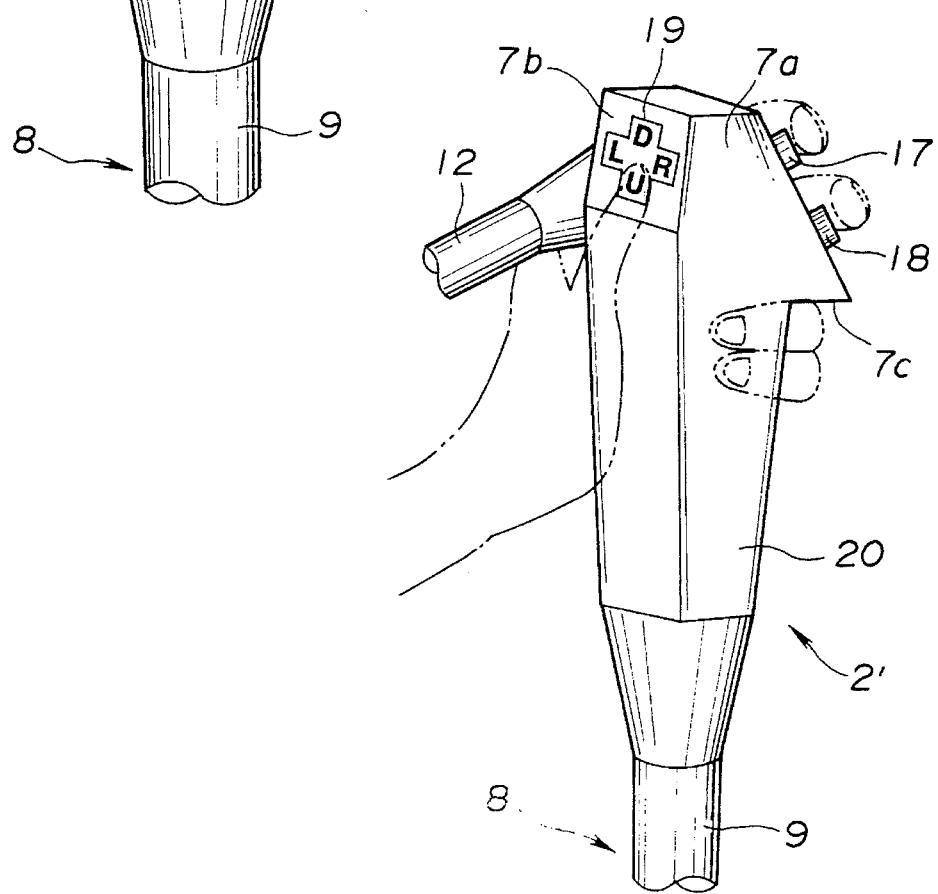
FIG. 7 is a perspective view showing an operating section according to a modification of the first embodiment of the invention.

FIG. 7 shows an electronic endoscope 2' which is a modification of the first embodiment of the invention. The electronic endoscope 2' is arranged such that, in the endoscope 2 illustrated in FIG. 1, the switch box 7a at the upper portion of the grasping portion 20 is formed on a step surface or the projecting surface 7c in which the lower end of the surface on which the gas-feed/water-feed switch 17 and the suction switch 18 are formed projects in a stepwise manner.

That is, the projecting surface 7c in which the side adjacent to the switch box 7a projects is formed on a connection boundary portion between the grasping portion 20 forming the operating section 7 and the switch box 7a formed at an upper portion of the grasping portion 20.

Accordingly, if the grasping portion 20 below the projecting surface 7c is grasped by the fifth finger and the third finger as illustrated in FIG. 7 so that the side of the third finger is abutted against the projecting surface 7c, the projecting surface 7c functions as a portion fastened so as not to come out, by the third finger. For this reason, even if a grasping force is low, it is possible to positively prevent the operating section 7 grasped from dropping out, and it is possible to increase a grasping area in case of being grasped. Thus, safety in the operation of the switches increases.

Other features are similar to those of the first embodiment.

A second embodiment of the invention will next be described with reference to FIGS. 8 to 10 of the accompanying drawings. This embodiment is arranged such that correspondence between a plurality of switches forming a curvature operating switch section and corresponding curvature driving directions can be switched.

Figure 8:
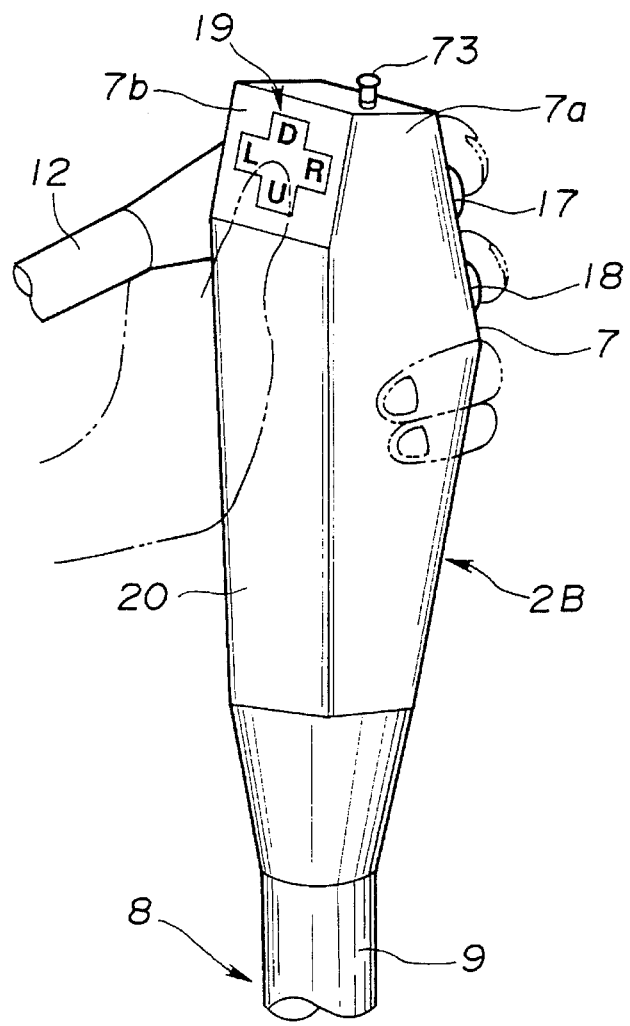

An operating section of an endoscope 2B according to the second embodiment is illustrated in FIG. 8. A change-over switch 73 is arranged at an upper surface, for example, of a switch box 7a. By operation of the change-over switch 73, a plurality of switches U, D, R and L forming a curvature operating switch section 19 and corresponding curvature driving directions can be switched.

FIG. 9 shows an entire arrangement of an electronic endoscope apparatus 1B provided with the electronic endoscope 2B. FIG. 9 is the same in block arrangement as FIG. 4, except that the change-over switch 73 is arranged on the electronic endoscope 2B. FIG. 10 shows an internal arrangement except for a hydraulic control system of the apparatus 1B.

Figure 10:
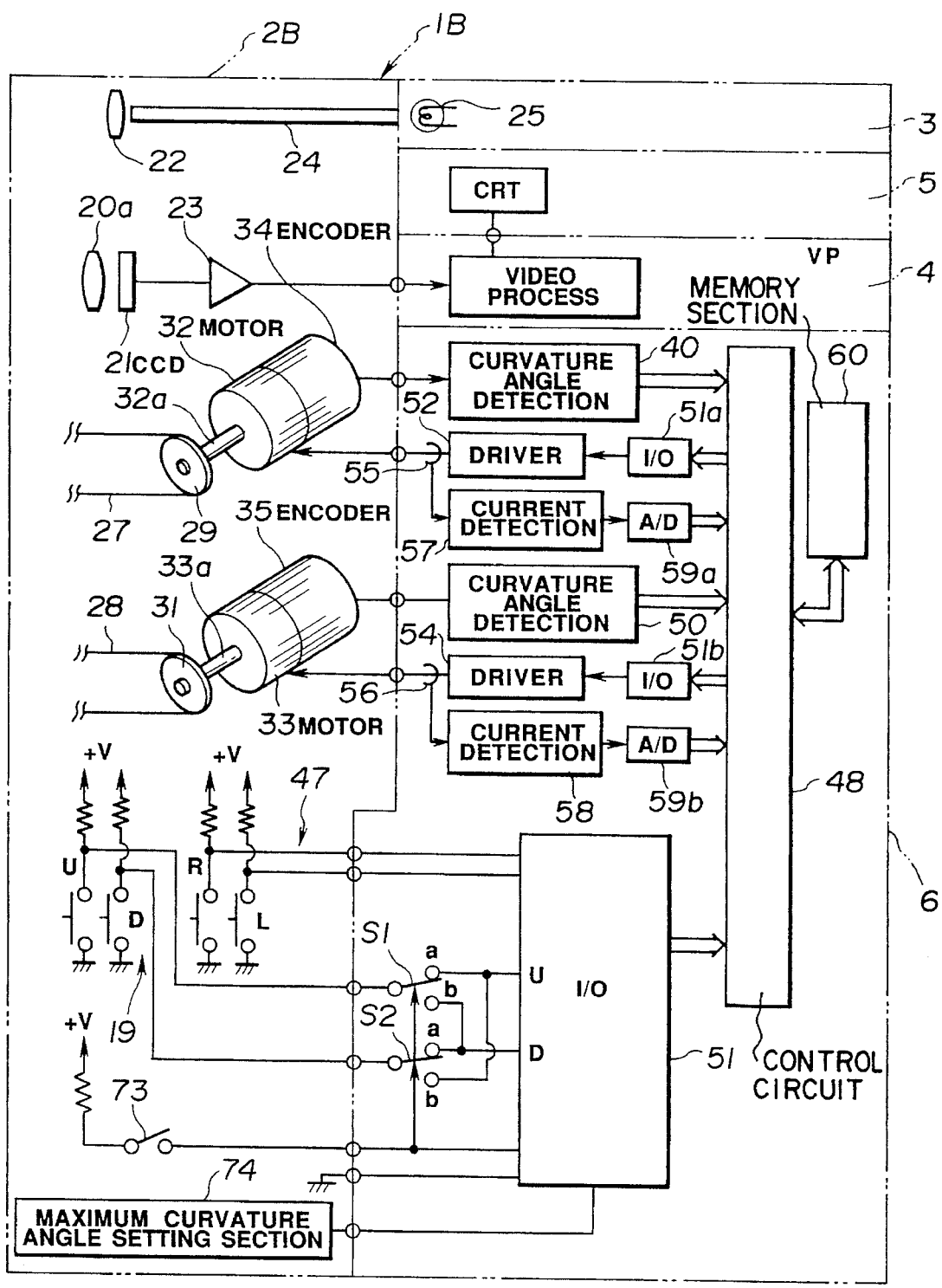

FIG. 10 shows an arrangement wherein a mechanism is provided in which, in FIG. 3, outputs from the respective switches U and D can be switched by an output from the change-over switch 73. As shown in FIG. 10, when the change-over switch 73 is turned OFF, an output from the change-over switch 73 is "H". A pair of analog switches S1 and S2 in which the output is applied to the change-over terminal are such that the outputs from the respective switches U and D are led to a pair of U and D input terminals of an I/O 51 through contacts a of the respective switches U and D. The pair of analog switches S1 and S2 are interlocked with each other during switching operations.

When the change-over switch 73 is turned ON from this condition, the output from the change-over switch 73 is brought to "L". The analog switches S1 and S2 lead the outputs from the respective switches U and D and U input terminal of the I/O 51 through contacts b. That is, functions of the respective switches U and D are switched.

Moreover, as shown in FIG. 10, a maximum curvature-angle setting portion 74 is provided in the present embodiment. The maximum curvature-angle setting portion 74 is formed by, for example, a dip switch. In a case where a setting value of the maximum curvature angle is desired to be changed, setting of the dip switch should be changed. Thus, changing of the setting value is easy. For example, in a case where repeated use extends a pair of wires 27 and 28, setting of the dip switch increases or becomes large, as a first aid at the time there cannot be produced the original maximum curvature angle (the original maximum curvature angle decreases), even if a pair of motors 32 and 33 are rotated through the quantity the same as the previous one. By doing so, there can be produced the maximum curvature angle the same as the previous one.

In connection with the above, the maximum curvature-angle setting portion 74 may be a ROM to which curvature-angle data are written. Further, the maximum curvature-angle setting portion 74 may also be a resistor. In this case, a control circuit 48 reads a resistance value as curvature-angle data. Alternatively, the maximum curvature-angle setting portion 74 may be arranged such that the maximum curvature-angle setting portion 74 is a bar code, and a bar-code reader is arranged within a curvature-motor control device 6 to read the curvature-angle data.

Other features are similar in arrangement to the first embodiment, and the description thereof will be omitted.

The present embodiment is arranged such that, when the operator grasps a grasping portion 20, the change-over switch 19 can be operated by the thumb of the hand of the operator. When a change-over switch 73 is turned OFF, a switch arranged closest to the thumb (the U switch in the illustrated embodiment) is operated. Then, upward curvature is applied. Since the upward curvature switch which is the most in number of operations is arranged at a position the easiest in operation, the operator feels less fatigue. Particularly, the switch is so arranged as to be easy in operation for the operator skillful in endoscope operation. Alternatively, the switch can be switched according to the operator's liking or choice.

On the other hand, when the change-over switch 73 is turned ON, at the time an inserting section 8 is held vertically downwardly, upward curvature is applied when the upward switch (D switch) is operated, while downward curvature is applied when the downward switch (U switch) is operated. That is, for the operator, if the switch located in a direction desired to be curved is depressed, there can be produced the desired curvature. Since the vertical and lateral directions correspond to the vertical and lateral arrangement of the switches, the curvature direction and the direction in which the monitor image moves, an unfamiliar operator should depress a switch in a direction desired to be curved. Thus, the operator can operate without confusion.

If the change-over switch 73 is brought to a switch provided with an LED, it is possible for the operator to easily affirm or confirm the ON/OFF condition.

In connection with the above, there are many examples where the endoscope is used with the inserting section directed vertically downwardly. An example of change-over of the switches U and D has been described. However, there is also a case where the inserting section is used with the inserting section directed horizontally. Change-over may be due to the switches L and R. Alternatively, functions of all of the switches may be changed over.

In connection with the above, the endoscope may be an optical endoscope in which an image guide fiber is used, but may not be limited to the electronic endoscope of the example illustrated in the drawings.

According to the present embodiment, indication of the curvature indicating input means and correspondence of the curvature section in the curvature direction are switched by the switch means, reducing operator fatigue, taking ergonomics into consideration, for example. A feel of physical disorder is eliminated in the correspondence between the arrangement of the curvature indicating means and a direction of movement of the endoscope image and the curvature direction, or selection of the curvature operation functions can be executed in accordance with a demand or request from the operator.

Figure 11:
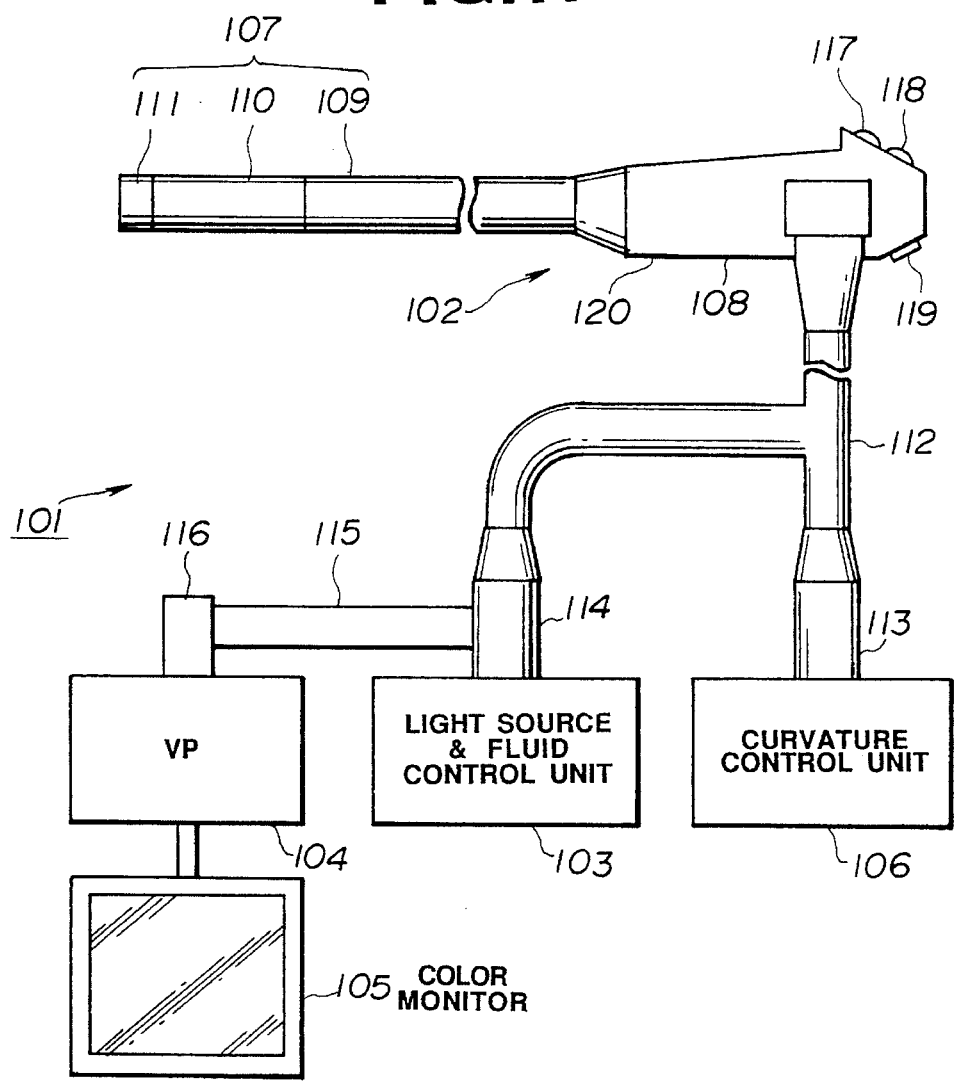

A third embodiment of the invention will next be described with reference to FIGS. 11 to 17 of the drawings. FIG. 11 is a view showing an entire arrangement of the third embodiment of the invention.

An endoscope apparatus 101 according to the third embodiment comprises an endoscope 102 provided therein with a solid-state image pickup element such as a CCD or the like, a light source device 103 for supplying an illuminating light to the endoscope 102, a video control device 104 for driving the solid-state image pickup element to convert the image pickup signal from the solid-state image pickup element to an image signal, a color monitor 105 for projecting the image signal from the video control device 104, and a curvature motor control device 106 for controlling curvature of a curvature portion 110 of the endoscope 102.

The endoscope 102 is provided with an inserting section 107 formed in an elongated fashion so as to be capable of being inserted into a subject, and an operating section 108 having a large diameter connected to a side of a rearward end of the inserting section 107. To the inserting section 107 are connected a flexible soft portion 109, and a plurality of curvature pieces in order from the side of the operating section 108. The inserting section 107 is so arranged that the curvature portion 110 and a hard forward arrangement portion 111 are connected to the inserting section 107 in four directions including vertical and lateral directions.

The forward arrangement portion 111 is provided with an objective optical system, and an illuminating optical system (not shown). A photoelectric transferring surface of the solid-state image pickup element which photoelectrically transfers a subject image to an image pickup signal to output the same is arranged at a focal position of the objective optical system. A light guide consisting of a fiber bundle for transmitting an illuminating light has been outgoing end thereof which is arranged at the illuminating optical system.

Moreover, a universal cable 112 branching into two on the way is connected to a side of the operating section 108. The ends of the branched portion of universal cable 112 are provided with a motor-control-device connector 113 detachably connected to the curvature motor control device 106, and a light guide connector 114 detachably connected to the light source device 103.

Further, a video control cable 115 extends from the side of the light guide connector 114. An end of the video control cable 115 is provided with a video-control-device connector 116 detachably connected to the video control device 104.

The signal cable connected to the solid-state image pickup element is inserted into the inserting section 107, the operating section 108 and the universal cable 112, and extends from the side of the light guide connector 114 to the video-control-device connector 116 through the video control cable 115.

Similarly, the light guide is inserted into the inserting section 107, the operating section 108, and the universal cable 112, and extends to the light guide connector 114. The light guide is connected such that an incident end thereof is exposed within the light source device 103.

The light source device 103 is provided with a light source (not shown). An illuminating light going out from the light source is incident upon the light-guide incident end of the light guide connector 114 so that the illuminating light is irradiated to the subject or the like from the illuminating optical system.

In connection with the above, the light source device 103 is a light source device for outputting surface successive lights including red, green and blue, in a case where the endoscope 102 is an electronic endoscope of a simple-plate RGB surface successive system. In a case where the endoscope 102 is an electronic endoscope of a single-plate color tip simultaneous system, the light source device 103 is a light source device for outputting a white light.

Further, the video control device 104 is provided with an image signal processing circuit (not shown). The image signal processing circuit has an input end which is connected to a connector receptor of the video-control-device connector 116, and an output end which is connected to the color monitor 105. The image signal processing circuit drives the solid-state image pickup element of the endoscope 102, and converts the image signal pickup signal from the solid-state image pickup element to an image signal, to output the image signal to the color monitor 105. As a result, an observing image of the subject is projected onto the color monitor 105.

On the other hand, the operating section 108 of the endoscope 102 is provided with a gas-feed/water-feed button 117 for cleaning an observing window of an objective optical system (not shown), and a suction button 118 for sucking or drawing body liquid or the like. The gas-feed/water-feed button 117 is operated whereby gas feed or water feed is executed. The suction button 118 is operated whereby suction of the body fluid or the like is executed from a suction channel (a treatment-instrument channel) (not shown) which is arranged within the endoscope 102.

Furthermore, the operating section 108 is provided with a cruciform curvature operating switch 119 serving as curvature operating means for curvature-operating the curvature portion 110. The curvature operating switch 119, a curvature mechanism to be described later, arranged within the operating portion 108, a drive motor 120 to be described later, serving as drive means for driving the curvature mechanism, and the curvature motor control device 106 serving as control means for controlling the drive motor 120 cooperate with each other to form a curvature device. The curvature device can curve the curvature portion 110 at an indicated curvature rate in vertical and lateral curvature directions.

The curvature operating switch 119 is capable of being pivoted or inclined in any cruciform direction, so that the curvature portion 110 can be operated to curve in four directions including vertical and lateral direction. The curvature operating switch 119 is connected to the curvature motor control device 106 by the motor-control-device connector 113 through a signal line (not shown) which is inserted through the universal cable 112.

Figure 12:
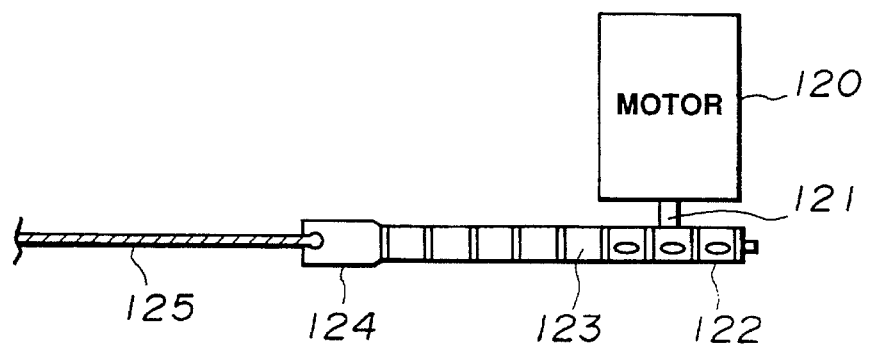
FIGS. 11 to 17 relate to a third embodiment of the invention, FIG. 11 being a view showing a whole or entire arrangement of an endoscope apparatus.

Moreover, the operating section 108 has built therein a curvature mechanism for curving the curvature portion 110. As shown in FIG. 12, the curvature mechanism comprises a sprocket 122 fixed to a drive shaft 121 of the drive motor 120 consisting of a direct-current motor, a chain 123 in mesh with the sprocket 122, a curvature operating wire 125 connected to an end of the chain 123 through a connecting element 124 and so on. Two sets of the curvature mechanisms similar to each other are provided for curvature in a vertical direction and for curvature in a lateral direction, and are controlled in driving by the curvature motor control device 106.

The curvature operating wire 125 is inserted into the curvature section 110 through the soft portion 109, and is connected to a curvature piece (not shown) at the forward end of the curvature portion 110. When the curvature operating wire 125 is operated in traction by the drive motor 120, the curvature operating wire 125 drives in curvature the curvature portion 110 in the vertical direction or in the lateral direction.

Figure 13:
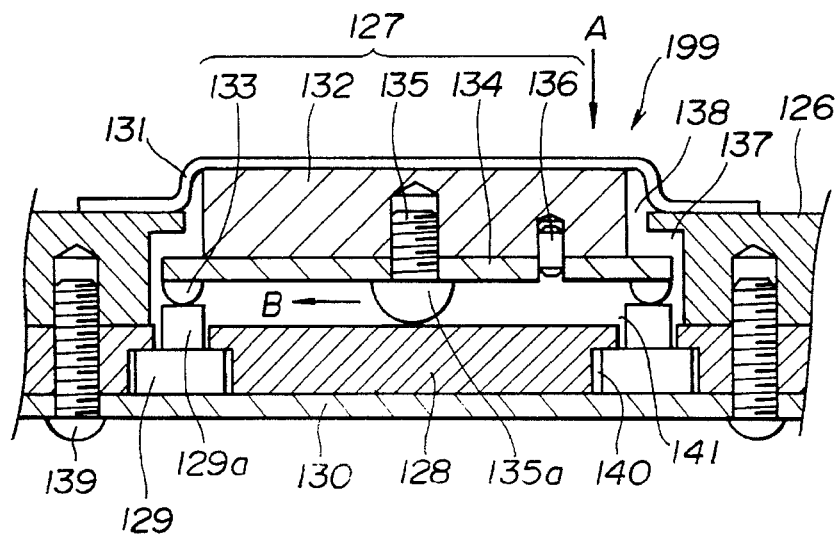

As shown in FIG. 13, the curvature operating switch 119 is mounted on a case 126 which forms an armor of the operating section 108. The curvature operating switch 119 comprises a cruciform pad arrangement portion 127 which is brought to a curvature operating portion, a switch presser 128 arranged below the cruciform pad arrangement portion 127, four two-stage ON-OFF switches 129 capable of being operated in two stage manner, a switch substrate 130 on which the two-stage ON-OFF switches 129 are mounted, and a round rubber sheet 131 serving as a waterproof element covering the cruciform pad arrangement portion 127.

The cruciform pad arrangement portion 127 comprises a cruciform pad 132 in the form of a cruciform, a disc 134 in which four urging pins 133 for urging the two-stage ON-OFF switch 129 are fixed on a circle equidistantly, a screw 135 having a generally hemispherical head 135*a*, and a positioning pin 136. The cruciform pad 132 and the disc 134 are positioned by the positioning pin 136 such that the urging pin 133 corresponds to a curvature direction of the cruciform pad 132 in vertical and lateral directions, and are fastened to each other at a central portion by the screw 135.

The disc 134 of the cruciform pad arrangement portion 127 is received in a circular counterbore opening 137 provided in the case 126, and the cruciform pad 132 projects to the outside of the case 126 from a cruciform through bore 138 which is a size smaller than the counterbore opening 137. A stem 129*a* that is an urging portion of each of the two-stage ON-OFF switches 129 is so arranged as to be opposed against the corresponding urging pin 133.

The switch presser 128 is provided with rectangular counterbore openings 140 for receiving therein respectively the two-stage ON-OFF switches 129, and rectangular through bores 141 each of which is a size smaller than the corresponding rectangular counterbore opening 140 and into which the stem 129*a* of each of the two-stage ON-OFF switches 129 is insertable. The switch substrate 130 is fixed to the side of an inner surface of the case 126 by screws 139 while sandwiching the switch presser 128. The two-stage ON-OFF switches 129 are fixed respectively to the rectangular counterbore openings 140.

In this case, a head 135*a* of the screw 135 of the cruciform pad arrangement portion 127 is so supported as to be movable on the switch presser 128. The urging pins 133 are located respectively on the stems 129*a* of the two-stage ON-OFF switches 129. When the cruciform pad arrangement portion 127 is inclined toward an optional direction of the vertical and lateral directions, a corresponding switch of the four two-stage ON-OFF switches 129 is turned ON.

Further, the arrangement is such that the rubber sheet 131 is fixed to the case 126 so as to cover the cruciform pad arrangement portion 127, to prevent water from entering from a location between the cruciform pad arrangement portion 127 and the cruciform through bore 138 at cleaning of the endoscope 102. Thus, the arrangement is small in size and has superior waterproof characteristics.

In connection with the above, there is no case where the cruciform pad arrangement portion 127 is out of the case 126, because the disc 134 is larger than the cruciform through bore 138.

Figure 14:
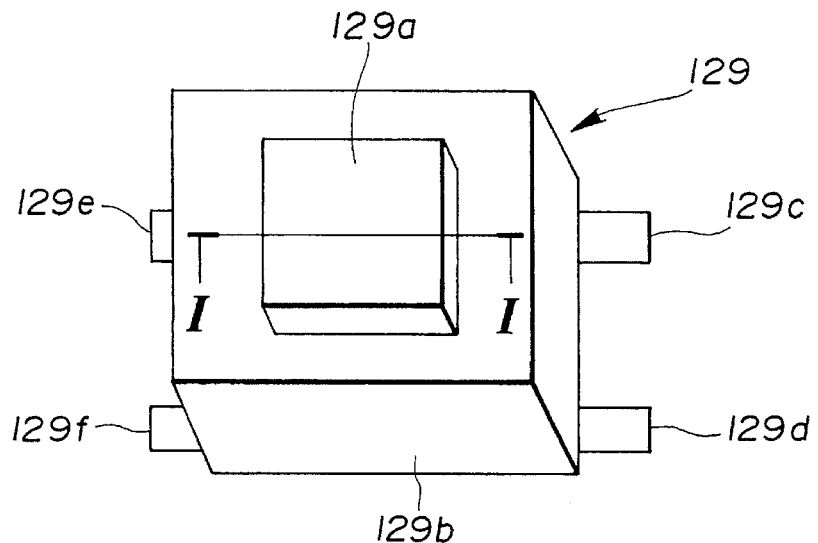

Here, as shown in FIG. 14, the two-stage ON-OFF switch 129 is such that the stem 129*a* projects out of a case 129*b* that is a switch armor, and the four terminals 129*c*, 129*d*, 129*e* and 129*f* that are terminal portions of the switch are provided on a side of the case 129*b*.

Figure 15:
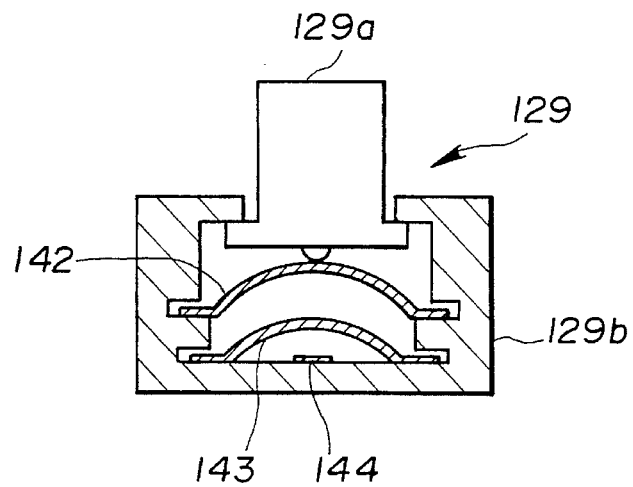

As shown in FIG. 15, a first click plate 142 made of a metal, a second click plate 143 similarly made of a metal, smaller than the first click plate 142, and a conductor 144 are provided in order from a location below the stem 129*a*, within the two-stage ON-OFF switch 129.

The first and second click plates 142 and 143 are both curved so that respective ends thereof are supported by the case 129*b*, and central projections each in the form of a curvature of the first and second click plates 142 and 143 and a conductor 144 are arranged substantially along an axial center of the stem 129*a*.

Furthermore, by wiring (not shown), the first click plate 142 and the terminal 129*c*, the second click plate 143 and the terminal 129*d*, and the conductor 144 and the terminal 129*e* are connected respectively to each other. The remaining terminal 129*f* is not connected as a terminal exclusive for fixture of a substrate.

When the stem 129*a* of the two-stage ON-OFF switch 129 is depressed once, the first click plate 142 is deformed by the stem 129*a* so as to be into contact with the second click plate 143. Thus, the first click plate 142 and the second click plate 143 are conducted to each other so that the terminal 129*c* and the terminal 129*d* are conducted to each other.

When the stem 129*a* is further pushed under this condition, the first click plate 142 and the second click plate 143 are deformed by the stem 129*a*. The first click plate 142, the second click plate 143, and the conductor 144 are in contact with each other and are conducted to each other. Thus, all of the terminals 129*c*, 129*d* and 129*e* are conducted to each other.

Figure 16:
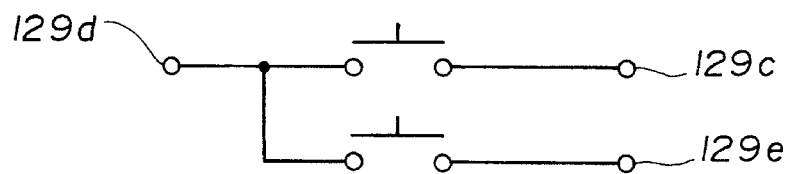

That is, as shown in FIG. 16, the two-stage ON-OFF switch 129 is so arranged as to form two switches between the terminals 129*d*–129*c* and between the terminals 129*d*–129*e*. A first-stage switch is formed between the terminals 129*d*–129*c*. A second-stage switch is formed between the terminals 129*d*–129*e*.

In connection with the above, when a force is not applied to the stem 129*a*, the first click plate 142 and the second click plate 143 are returned to their respective original configurations, so that the first click plate 142, the second click plate 143, and the first conductor 144 are separated from each other.

Figure 17:
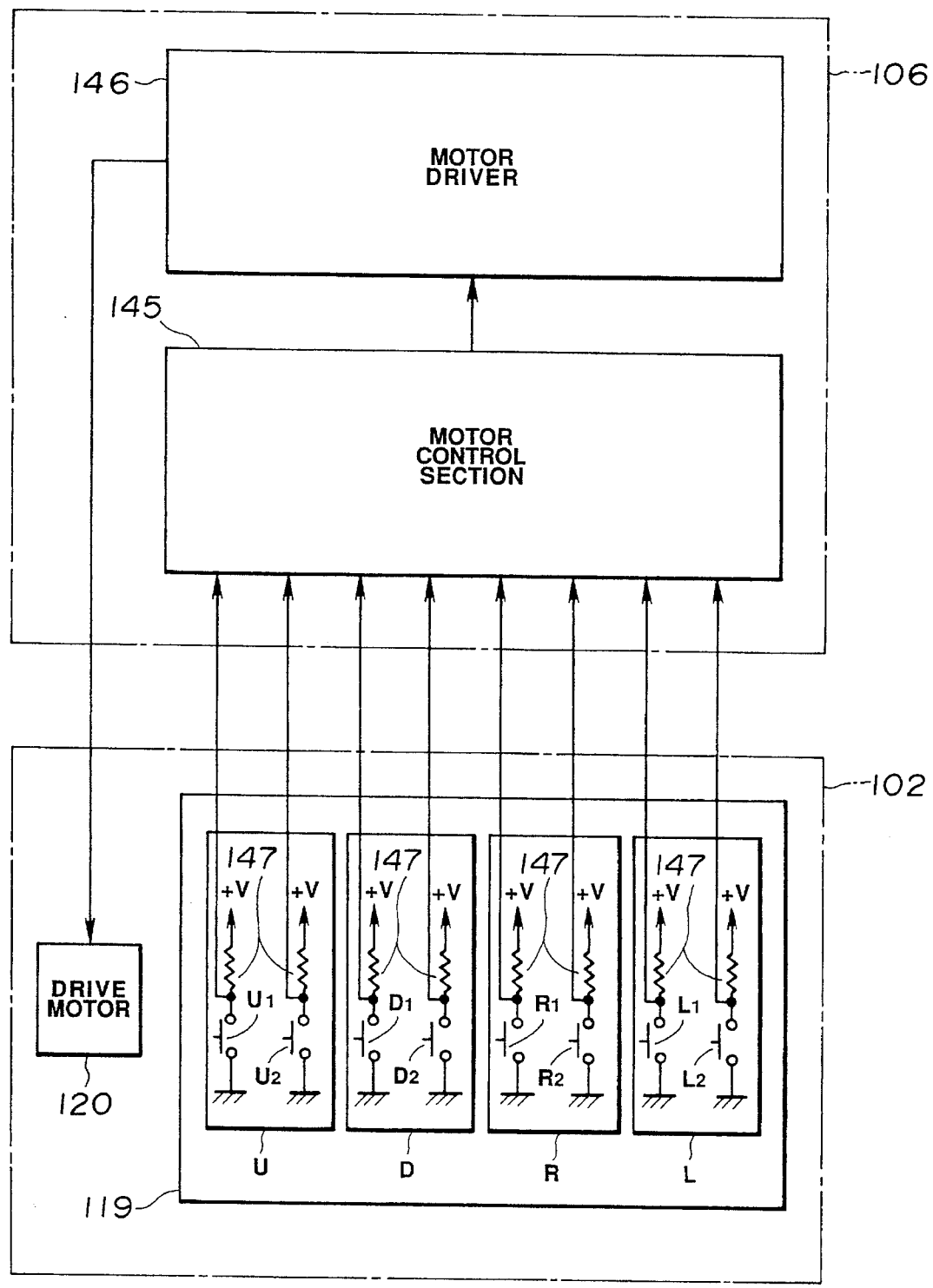

A curvature motor control device 106 will next be described. As shown in FIG. 17, the curvature motor control device 106 is provided with a motor control section 145 to which a curvature operating switch 119 in which four (4) two-stage ON-OFF switches 129 are incorporated is connected, and a motor driver 146 for driving the drive motor 120 of the curvature mechanism.

Here, it is assumed that four two-stage ON-OFF switches 129 corresponding to vertical and lateral curvature directions of the curvature operating switch 119 are switches U, D, R and L, respectively. Then, as described previously, there are two switches within each of the switches. Hereunder, it is assumed that the first-stage and second-stage switches within the switch U are switches U1 and U2, the first-stage and second-stage switches within the switch D are switches D1 and D2, the first-stage and second-stage switches within the switch R are switches R1 and R2, and the first-stage and second-stage switches within the switch L are switches L1 and L2.

Each of the switches U1, U2, D1, D2, R1, R2, L1 and L2 is such that the terminal on the side connected to the motor control portion 145 is pulled up to the power source V through a corresponding one of resistors 147, and the other terminal is grounded. If citing is made to the switch U, the switch U1 is turned ON when first depression is made. When depression is further executed, both the switch U1 and the switch U2 are turned ON at second depression. Thus, an ON-signal of a low level is outputted to the motor control portion 145.

A circuit arrangement of the motor control portion 145 is such that the motor control portion 145 receives a signal from, for example, the switch U which indicates upward curvature, and causes small current to pass through the drive motor 120 within the endoscope 102 from the motor driver 146 when the ON signal of a low level is inputted only from the switch U1 and from the switches U1 and U2, when an ON signal of a low level is inputted both from the switches U1 and U2, large current is caused to pass through the drive motor 120 from the motor driver 146. Similar arrangements can be applied to the switches D, R and L in the other directions.

Curvature operation and curvature drive control will next be described with reference to the curvature section 110 of the endoscope 102.

First, in a case where the curvature section 110 of the endoscope 102 is curved, apart of the curvature operating switch 119 arranged on the operation section 108 corresponding to a desired curvature direction is depressed.

For example, in FIG. 13, when the cruciform pad arrangement portion 127 is depressed in an A direction, the curvature section 110 is curved upwardly. When the cruciform pad arrangement portion 127 is depressed only through one step in the A direction, the cruciform pad arrangement portion 127 is inclined with the head 135*a* of the screw 135 serving as a fulcrum. The urging pin 133 depresses the stems 129*a* of the respective two-stage ON-OFF switch 129.

At this time, if the head 135*a* that is the fulcrum is restricted or restrained, a space between the cruciform pad 132 of the cruciform pad arrangement portion 127 on the urging side (A side) and the cruciform through bore 138 provided in the case 126 of the operating section 108 is reduced or narrowed. However, since the head 135*a* is not in fact fixed, the head 135*a* of the screw 135 is moved in a B direction in FIG. 13, and a space on the side opposite to the A side is substantially uniformized.

That is, in a case of a curvature operating switch which uses a conventional cruciform pad, since the cruciform pad is fixed so as not to be moved from the center of rotation, a wide space is formed on the side opposite to the side where the cruciform pad is urged. Thus, rattle or backlash occurs, damaging operability. In a case of the curvature operating switch 119 according to the present embodiment, rattle does not occur between the cruciform pad 132 and the case 126 of the operating section 108 at operation, so that operability can be improved.

The first-stage switch U1 of the two-stage ON-OFF switch 129 (the upward switch U) is turned ON, and the ON signal of a low level is sent only from the switch U1 to an upward control end of the motor control section 145 within the curvature motor control device 106. The motor control section 145 causes a small amount of current to flow to the drive motor 120 within the endoscope 102, from the motor driver 146. The drive motor 120 is rotated at a low speed so that the curvature section 110 is curved slowly upwardly.

Further, when the cruciform arrangement portion 127 of the curvature operating switch 119 is pushed in the A direction to operate the second stage, both the switch U1 and the switch U2 are turned ON, so that the ON signal of the low level is sent both from the switches U1 and U2 to the upward control end of the motor control section 145. Then, the motor control section 145 controls the flow of a large current from the motor driver 146 to the drive motor 120. The drive motor 120 is rotated at high speed so that a curvature rate of the curvature section 110 increases.

That is, since the two-stage ON-OFF switch 129 is provided for every vertical and lateral curvature direction of the curvature operating switch 119, it is possible to simultaneously indicate the curvature direction and the curvature speed. Furthermore, since the endoscope is small in size and is waterproof, handling operability is considerably improved. Moreover, by a click feel at the time the two-stage ON-OFF switch 129 is depressed at curvature operation, curvature operation can be executed while gripping or grasping a change of curvature speed. Thus, safety is further improved.

In connection with the above, in the present embodiment, the two-stage ON-OFF switch 129 is used as the curvature operating switch 119. However, the arrangement may be such that a multi-stage switch more than three stages is used to execute control at a further fine curvature speed.

Figure 18:
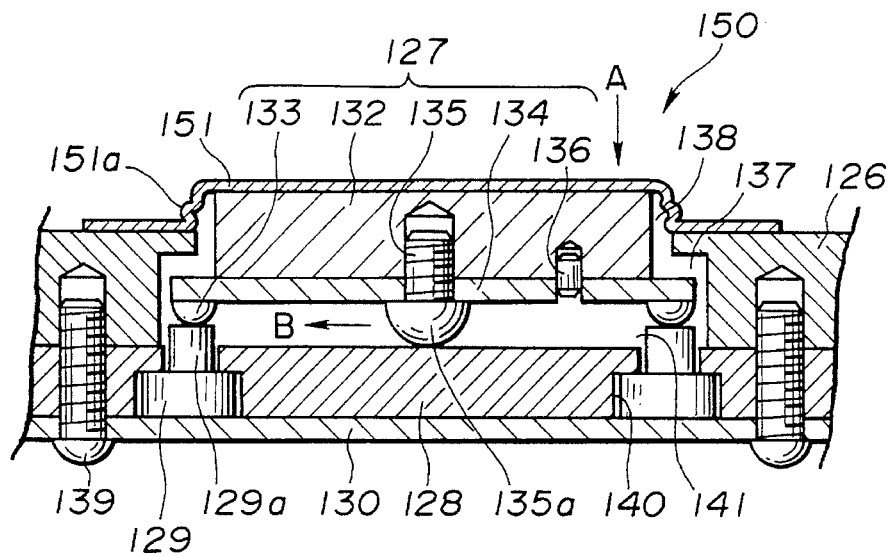
FIGS. 18 to 20 relate to a fourth embodiment of the invention, FIG. 18 being a cross-sectional view showing the curvature operating switch in the second embodiment of the invention.

FIG. 18 shows a structure of a curvature operating switch according to a fourth embodiment of the invention.

The present embodiment is arranged such that the curvature operating switch 119 in the aforesaid third embodiment is brought to a curvature operating switch 150 covered with a rubber sheet 151 having bellows, the internal arrangement within the curvature motor control device 106 is partially modified, and the curvature speed is changed with time, although the curvature speed is constant at low speed and at high speed in the third embodiment.

In connection with the above, in the following description, the same or identical reference numerals are applied to parts and elements the same as or identical with those of the aforementioned third embodiment, and the description thereof will be omitted.

As shown in FIG. 18, the curvature operating switch 150 is provided with the rubber sheet 151 having a bellows portion 151*a* which is provided circumferentially. The rubber sheet 151 is fixed to a case 126 in the form covering a cruciform pad arrangement portion 127.

That is, when the cruciform pad arrangement portion 127 of the curvature operating switch 150 is pushed in a direction A, the cruciform arrangement portion 127 is inclined while ahead 135*a* of a screw 135 shifts toward a direction B, so that a side opposite to the pushed A side is raised. In the present embodiment, however, since the bellows portion 151a is provided on the rubber sheet 151, the folded bellows portion 151a is only straightened, but there is no case where a force with which the rubber is stretched occurs. For this reason, there can be produced a superior urging touch at operation of the curvature operating switch 150, as compared with the third embodiment of the invention.

Figure 20:
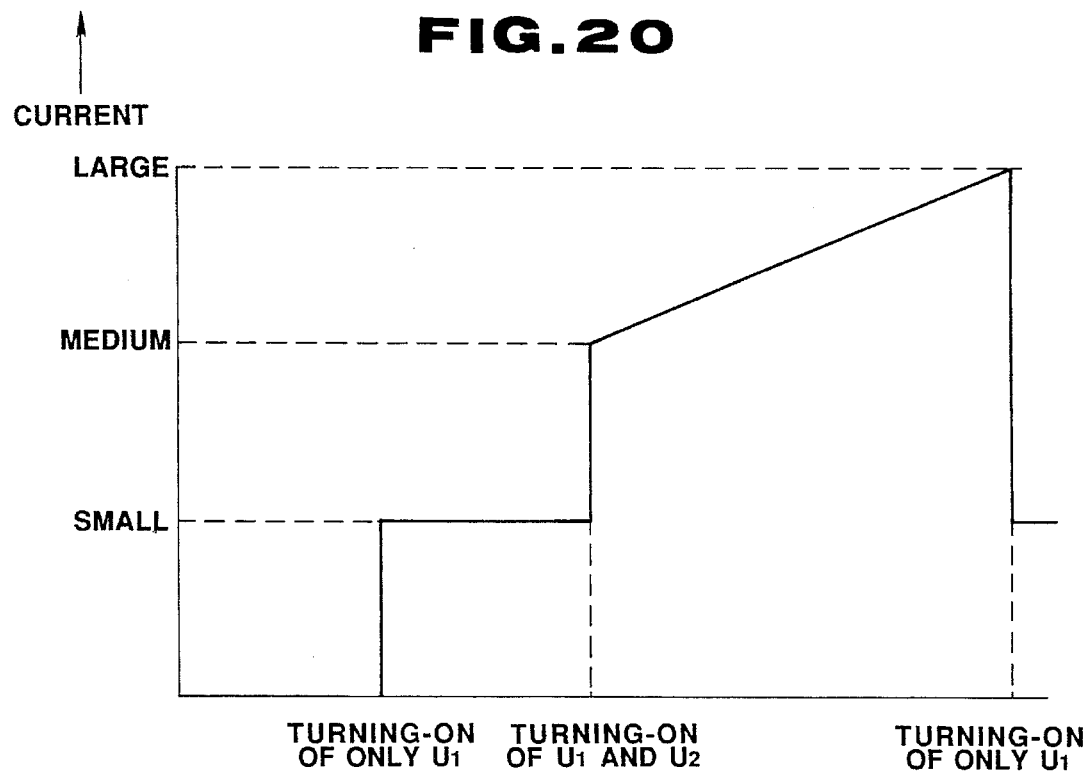
Figure 19:
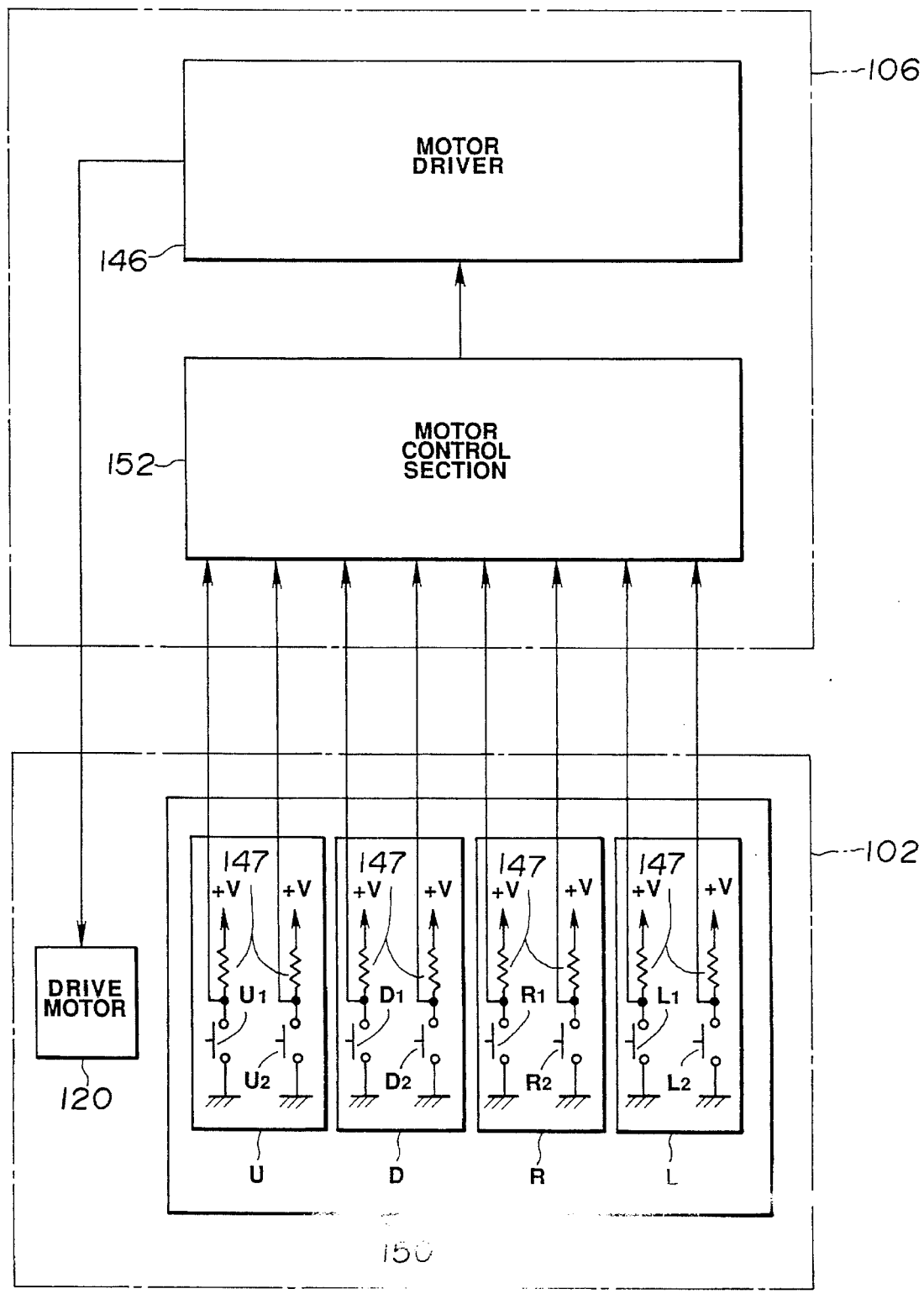

Furthermore, as shown in FIG. 19, a curvature motor control unit 106 is provided with a motor control section 152 which improves a function of the motor control section 145 in the third embodiment. As shown in FIG. 20, the motor control section 152 controls such that, when, for example, an ON signal only from a switch U1 is inputted to the motor control section 152, constant or predetermined small current flows from a motor driver 146 to a drive motor 120. Moreover, when the ON signal is inputted both from the switches U1 and U2, the curvature motor control device 106 controls such that current flowing through the drive motor 120 increases middle~large in accordance with time through which the switch is depressed.

That is, when a corresponding part of the curvature operating switch 150 is depressed through one stage in order to curve a curvature section 110 of the endoscope 102 upwardly, the switch U1 is turned ON, and the ON signal of the low level is inputted to the upward control end of the motor control section 152 within the curvature motor control device 106. Then, the motor control section 152 executes control such that a small amount of current flows to the drive motor 120 within the endoscope 102 from the motor driver 146. Thus, the drive motor 120 is rotated at low speed, and the curvature section 110 is curved slowly.

Furthermore, when the cruciform pad arrangement portion 127 of the curvature operating switch 150 is depressed to operate a second stage, both the switch U1 and the switch U2 are turned ON so that both the ON signals of the low levels are sent from the switches U1 and U2 to the upward control end of the motor control section 152.

The motor control section 152 causes middle current to flow to the drive motor 120 from the motor driver 146, to gradually increase the current in accordance with the time through which the switch is depressed. As a result, the drive motor 120 within the endoscope 102 is rotated at mid~high speed, and the curvature section 110 is also speedily curved gradually from the middle order. Operation due to other switches D, R and L is also similar to that of the switch U.

In the present embodiment, since the curvature speed of from low speed~high speed can be precisely controlled finely, a quick or fine curvature operation can be executed. Other advantages are similar to those of the aforesaid third embodiment of the invention.

In connection with the above, the present embodiment is arrangement such that the current of the drive motor 120 is small and constant at the first operation in the various curvature directions of the curvature operation switch 150, while the current of the drive motor 120 is variable from the mid~large current at the second-stage operation. However, the invention should not be limited to this specific embodiment. The arrangement may be such that a mode in which the current is variable at operation of the first stage from small~mid current, and the current is constant as large current at the second-stage operation, a mode in which the current is variable at operation of the first stage from small~mid current, and the current is variable at operation of the second stage from mid~large current and so on are changeable by inputting from the outside.

Figure 21:
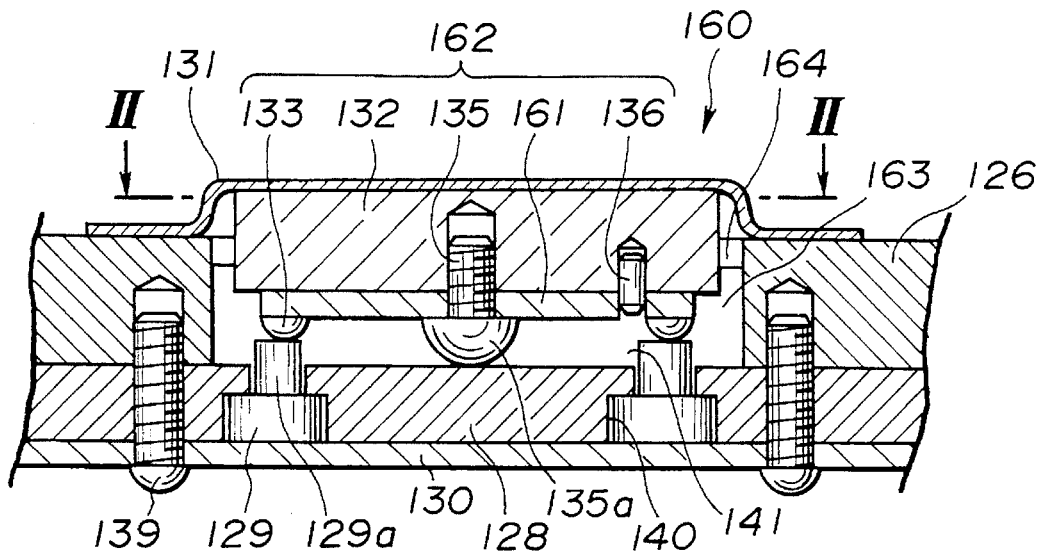
FIGS. 21 to 23 relate to a fifth embodiment of the invention, FIG. 21 being a cross-sectional view showing a curvature operating switch in the fifth embodiment of the invention.

FIG. 21 is a cross-sectional view of a curvature operating switch in a fifth embodiment of the invention.

The present embodiment is arranged such that a curvature operating switch 160 is used in which the curvature operating switch 119 in the third embodiment is reduced in size and, further, a priority right is applied to inputting from the curvature operating switch 160.

As shown in FIG. 21, the curvature operating switch 160 is brought to an arrangement in which a disc 134 of the cruciform pad arrangement portion 127 is brought to a disc 161 smaller than a cruciform pad 132, with respect to the curvature operating switch 119 in the third embodiment. The arrangement is such that around counterbore opening 163 and a cruciform through bore 164 substantially the same in size as the counterbore opening 163 are formed in a case 126 which forms an armor of the operating section 108 of the endoscope 102, and a cruciform pad arrangement portion 162 provided with the disc 161 is received in the case 126.

Figure 22:
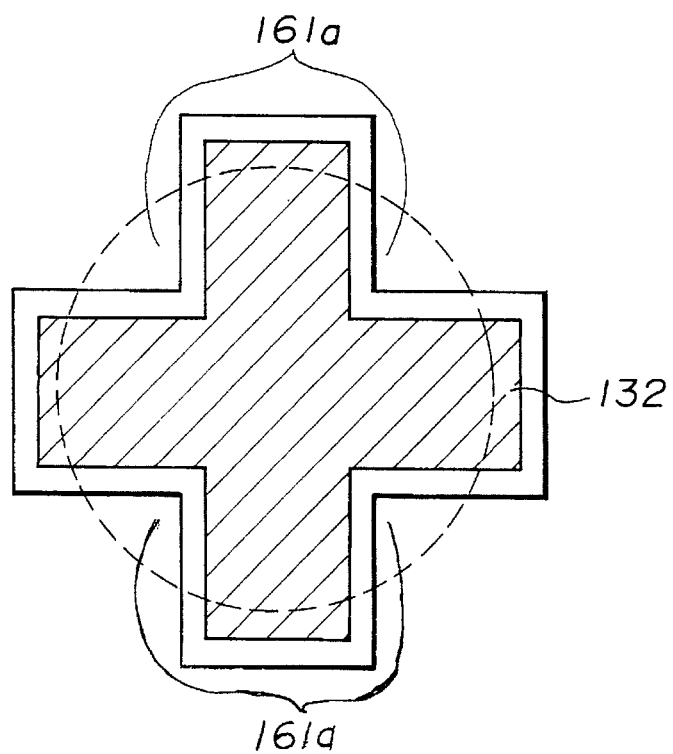

As will be seen from a view (a portion omitted) as viewed from line II—II in FIG. 21 shown in FIG. 22, the cruciform pad arrangement portion 162 is arranged such that coming-out or coming-off is prevented from occurring by four catching portions 161a that are portions which abut against the case 126 of the disc 161.

The curvature operating switch 160 of the present embodiment is such that, as compared with the third embodiment, the disc 161 is reduced in size, whereby it is possible to miniaturize the entire switch. Moreover, the center of rotation of the cruciform pad 132 is not fixed, but is movable in a direction opposite to the pressed or urging direction. The gap or clearance between the cruciform pad 132 and the cruciform through bore 164 in the case 126 is a minimum. Thus, rattle does not occur.

Figure 23:
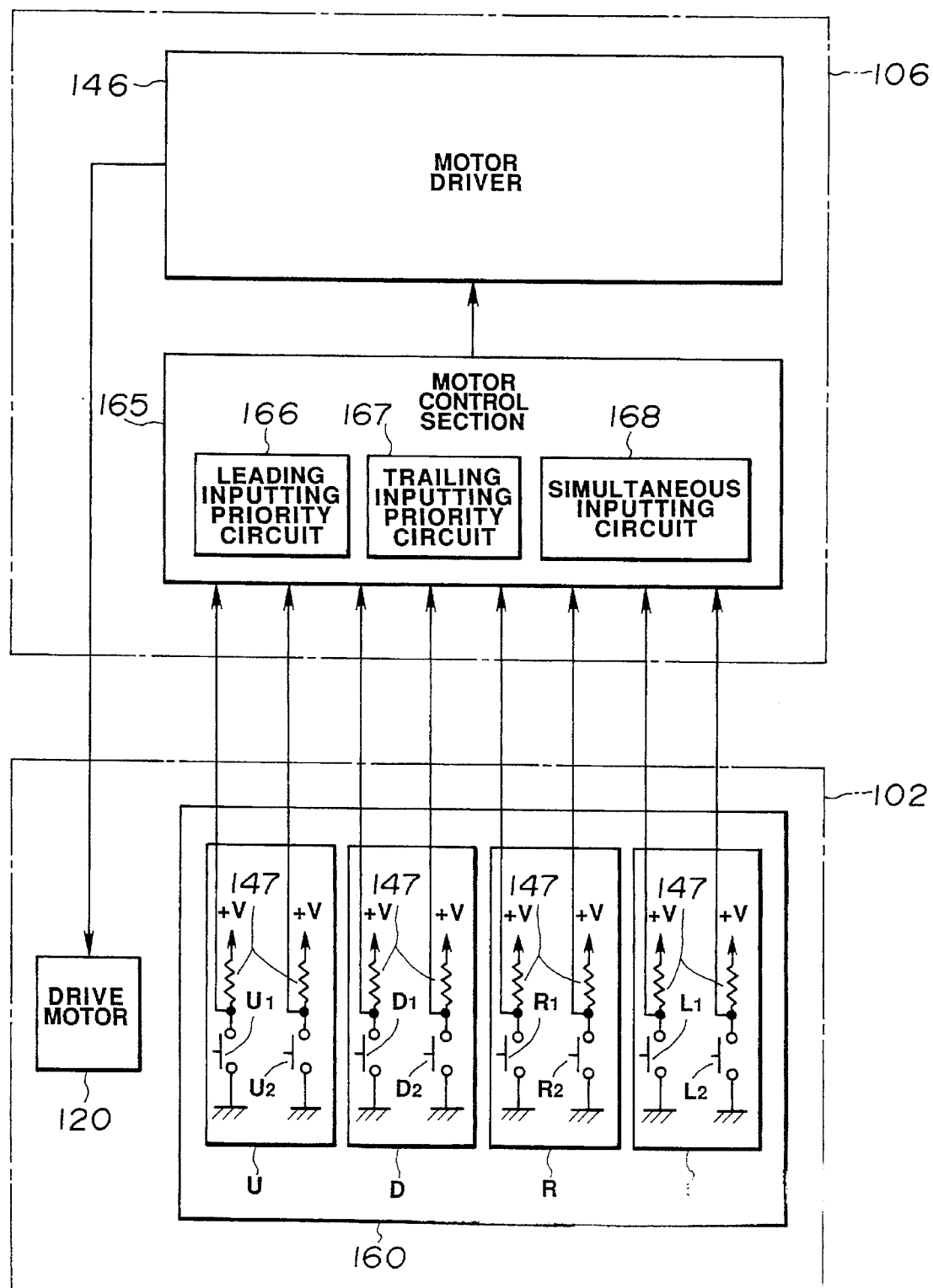

Further, as shown in FIG. 23, in the present embodiment, a curvature motor control device 106 is provided with an input-priority judging or discriminating function. That is, with respect to the motor control section 145 in the third embodiment, three circuits including a preceding-input priority circuit 166, a succeeding-input priority circuit 167, and a simultaneous or concurrent input circuit 168 are incorporated within a motor control section 165 in the present embodiment. It is possible to select any one of the circuits to use the circuit from the outside.

Function of the three circuits of the motor control section 165 will hereunder be described with a specific operational example cited.

First, in a case where the preceding input priority circuit 166 is selected, if a switch R is also depressed in the middle of depression of a switch U, only the signal from the switch U preceedingly inputted is fetched as an input at the motor control section 165, and a signal from the switch E inputted succeedingly is ignored and is not fetched as an input. Accordingly, a motor driver 146 is so controlled as to cause current for driving the curvature mechanism to flow upwardly. Thus, the curvature portion 110 of the endoscope 102 is curved upwardly.

On the other hand, in a case where the succeeding input priority circuit 167 is selected, if the switch R is also depressed similarly in the middle of depression of the switch U, the motor control portion 165 fetches, as an input, only a signal from the switch R inputted succeedingly, and a signal from the switch U originally inputted is ignored and is not fetched as an input. Accordingly, the motor driver 146 is so controlled as to cause current for driving the curvature mechanism in aright-hand direction to flow, so that the curvature portion 110 is curved in the right-hand direction.

Lastly, in a case where the simultaneous input circuit 168 is selected, if the switch R is also depressed similarly in the middle of depression of the switch U, the motor control portion 165 fetches, as an input, a signal from the switch U preceedingly inputted, and a signal from the switch R inputted succeedingly. Accordingly, the motor driver 146 is controlled to cause current for driving the curvature mechanism in an upward direction and aright-hand direction to flow, so that the curvature portion 110 is curved in the upward direction and the right-hand direction.

In the present embodiment, an input priority function of the motor control section 165 is set in accordance with the desire of the operator, whereby more soft and prompt curvature operation can be executed. Other functions and advantages are similar to those of the aforementioned third embodiment.

As described above, according to the third to fifth embodiments of the invention, the multi-stage switches in which operation at least equal to or more than two stages is possible are arranged every each direction of the curvature operation to form the curvature operating means. Accordingly, it is made possible to smoothly execute the operation indicating the curvature direction and the operation indicating the curvature speed without interruption of one of the operations. Moreover, the device can be made waterproof and miniaturization or reduction in size are made easy.

An endoscope apparatus according to a sixth embodiment of the invention will next be described with reference to FIGS. 24 to 30 of the drawings, in which dangerous malfunction can be prevented from occurring, increasing safety.

Figure 24:
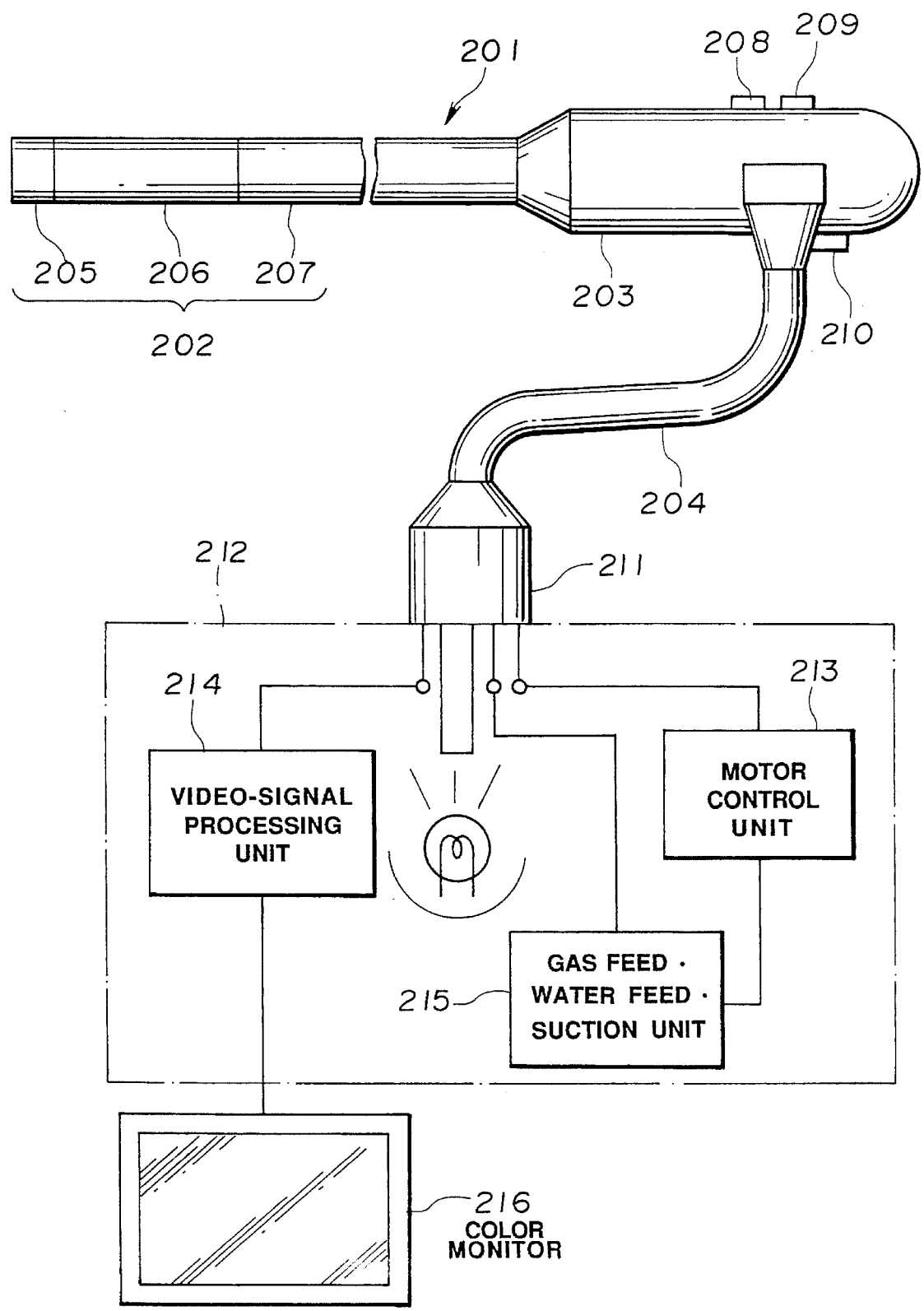
FIGS. 24 to 30 relate to a sixth embodiment of the invention, FIG. 24 being a view showing a whole or entire arrangement of an endoscope apparatus according to the sixth embodiment of the invention.

In FIG. 24, an electronic endoscope 201 comprises an elongated inserting section 202, an operating section 203 great in width formed at a rear end of the inserting section 202, and a universal cable 204 extending to the outside from the operating section 203.

Further, the inserting section 202 comprises a hard forward-end arrangement portion 205, a curvable curvature portion 206 and a flexible flexing tube portion 207 from the side of a forward end.

Moreover, the operating section 203 is provided with a gas-feed/water-feed switch 208, a suction switch 209 and a curvature switch 210 for curvature-operating the curvature portion.

Furthermore, a connector 211 for connection to an illuminating light source device 212 is mounted on a forward end of extension of the universal cable 204.

A motor control unit 213, a video-signal processing unit 214 and a gas-feed/water-feed and suction unit 215 are arranged within a body of the illuminating light source unit 212. When the connector 204 of the endoscope 201 is connected to the illuminating light source device 212, the motor control unit 213, the video-signal processing unit 214 and the gas-feed/water-feed and suction unit 215 are automatically connected to the side of the endoscope 201. Here, the gas-feed/water-feed and suction unit 215 and the motor control unit 213 are electrically connected to each other. Further, an image signal processed by the video-signal processing unit 214 is transmitted to a color monitor 216.

Figure 25:
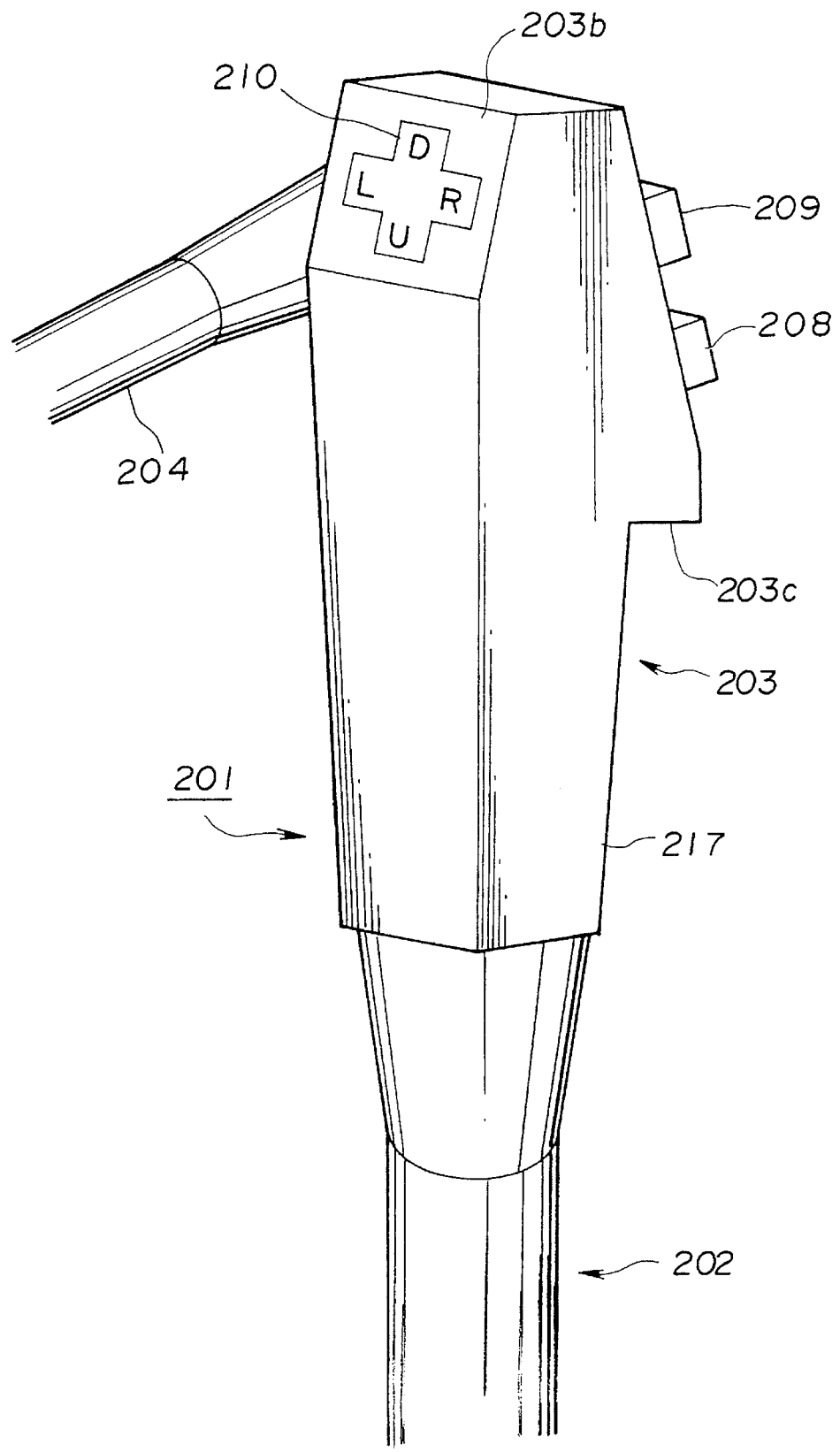

The curvature switch 210 is brought to a cruciform pad configuration as shown in FIG. 25. The switch 210 is provided with four (4) ON-OFF switches below a pad corresponding to vertical and lateral directions so as to be capable of issuing indication or instruction to curve the curvature portion 206 to an upper, a lower, the right-hand and the left-hand directions. Moreover, similarly to FIG. 7, the curvature switch 210 is provided with an inclined-surface portion 203b and a projection 203c serving as an antislipping device.

A position of the curvature switch 210 is located adjacent to a thumb of an operator when the operator grasps a grasping portion 217 grasped by the operator, with respect to the grasping portion 217, so that operation of the switch 210 can be executed by the thumb.

Reversely, the gas-feed/water-feed switch 208 and the suction switch 209 are located in a direction of a first finger and a second finger.

Figure 26:
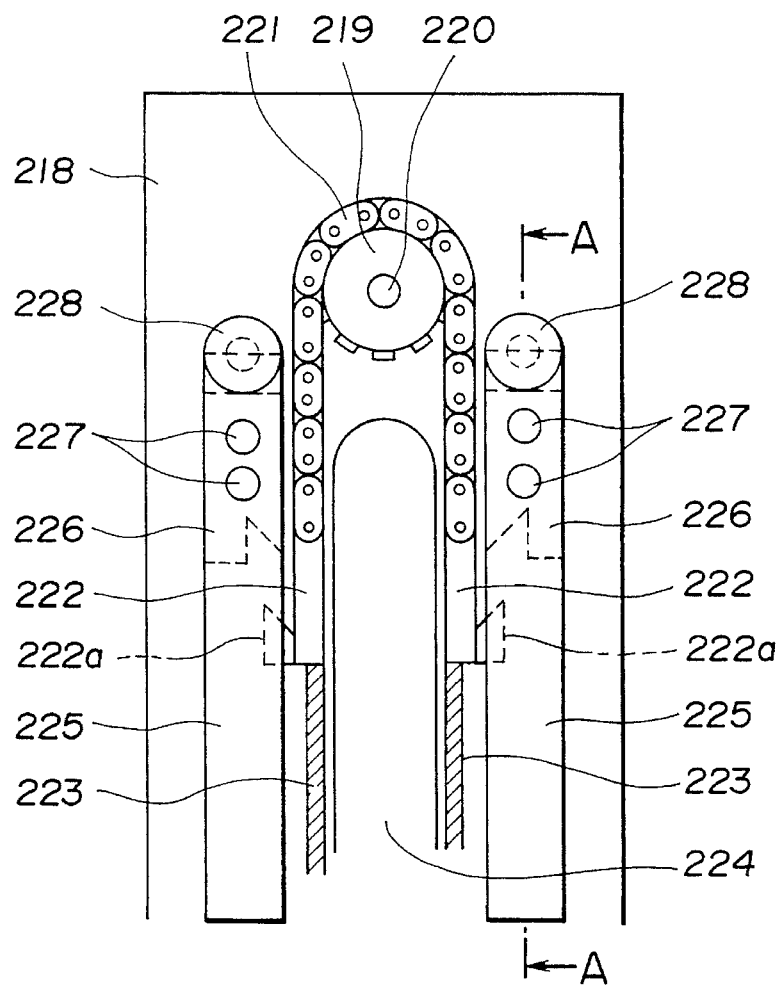

FIG. 26 is a view showing a curvature mechanism in a UD direction, within the operating section 203. An RL direction is the same in shape or configuration as the UD direction, and will be omitted.

In FIG. 26, a bottom board 218 is fixed within the operating section by a method (not shown). A sprocket 219 which is engaged with a drive gear fixed to a UD curvature motor (not shown) is rotatably supported on the bottom board 218 by a shaft 220 fixed to the bottom board 218.

Figure 27:
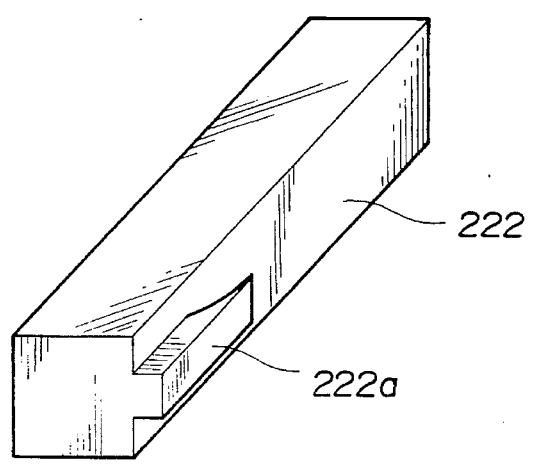

A chain 221 is engaged with the sprocket 219, and a chain end 222 is fixedly mounted on an end of the chain 221. The chain end 222 is provided with a hook 222a as shown in FIG. 27. Further, an angle wire 223 is fixedly mounted on the other end of the chain end 222. The other end of the angle wire 223 passes through the inserting section 202 illustrated in FIG. 24, and is fixedly mounted on the side of the forward-end arrangement portion 205 of the curvature section 206.

A center guide 224 for preventing both ends of the chain 221 from accessing each other is fixedly mounted on the bottom board 218 at a position clamped by the chain 221. Moreover, a side guide 225 for preventing both the ends of the chain 221 from being spaced away from each other is fixedly mounted on the opposite side of the center guide 224 of the chain 221.

Figure 28:
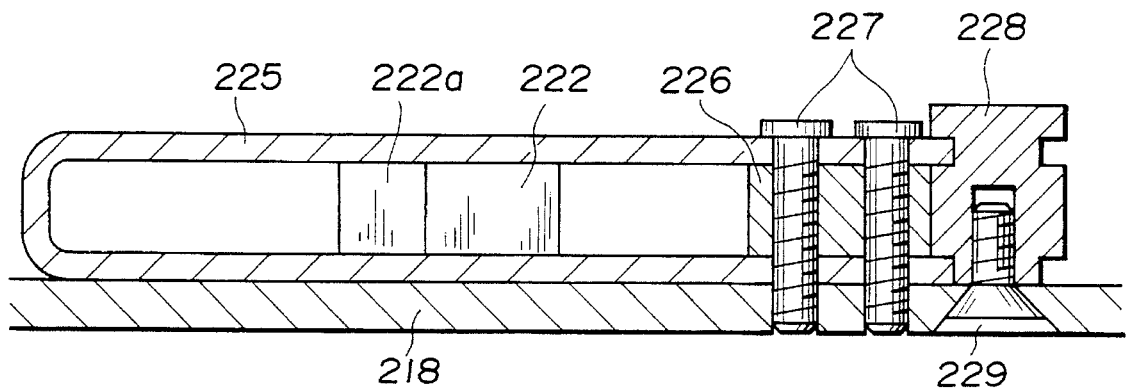

As shown in FIG. 28 which is a cross-sectional view taken along a line A—A in FIG. 26, the side guide 225 is one in which an elongated plate is bent into a U-shaped configuration, and the hook 222a of the chain end 222 is movably clamped between elements of the U-shaped configuration. Further, a chain end stopper 226 for deciding a quantity of movement of the chain guide 222 is clamped by an open end side of the U-shaped configuration of the side guide 225, and is fixedly mounted thereon.

The fixing is executed such that screws 227 pass through respective bores thereof provided in the side guide 225 and the chain end stopper 226 and joined to the bottom board 218. Moreover, the open end of the side guide 225 is provided therein with a semicircular cut-out. The cut-out is fitted into a groove in a side guide lock element 228 which is circular or columnar in configuration and which has a groove in a peripheral direction. The side guide lock element 228 is fixedly mounted on the bottom board 218 by a flat countersunk head screw 229.

Figure 29:
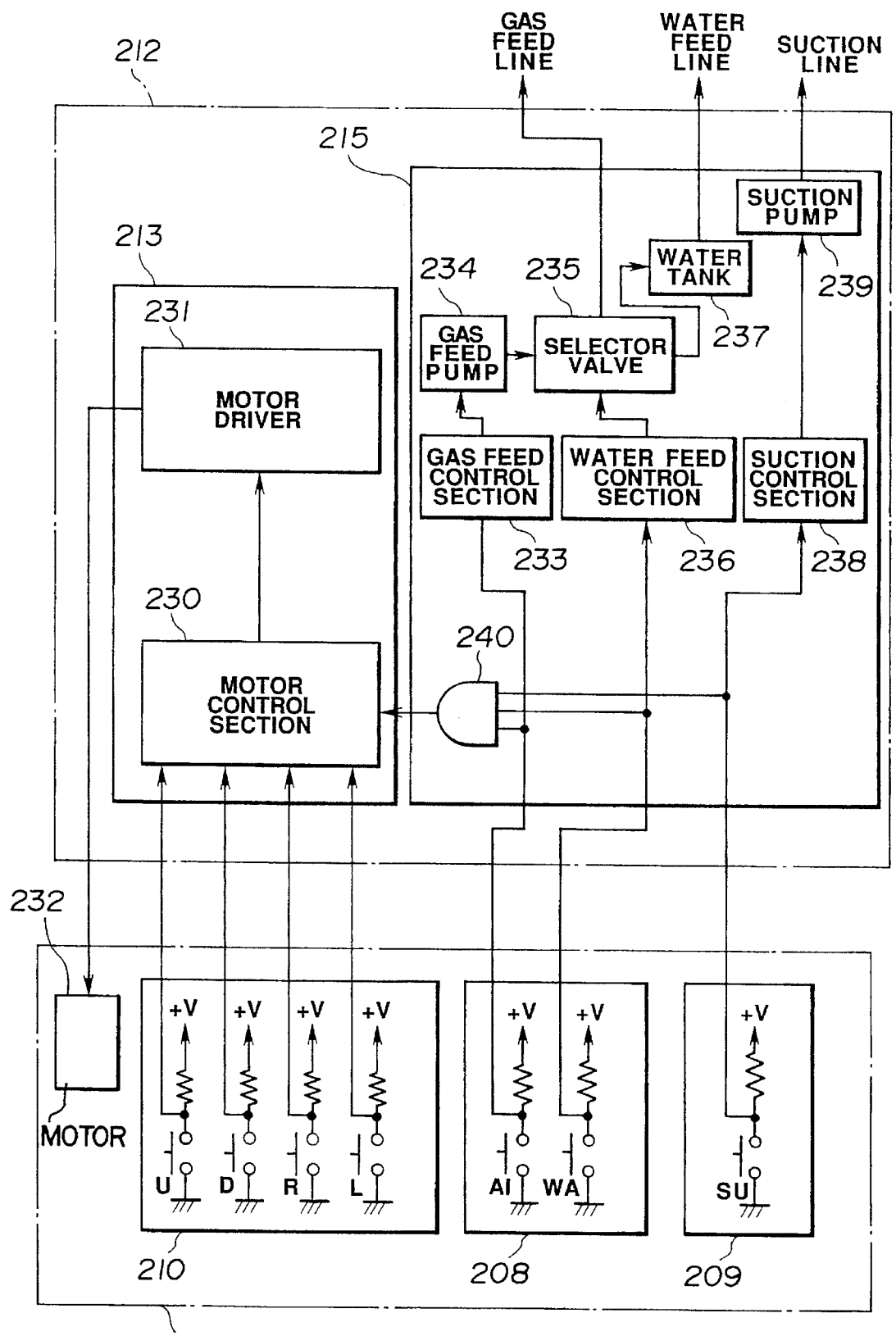

FIG. 29 is a connection view of a control system in relation to the curvature switch 210, the gas-feed/water-feed switch 208 and the suction switch 209.

The curvature switch 210, the gas-feed/water-feed switch 208 and the suction switch 209 are arranged within the electronic endoscope 201. The curvature switch 210 has four (4) switches (referred simply to as "switches U, D, R and L") corresponding respectively to curvature operations in vertical and lateral directions (U, D, R and L directions). The curvature switch 210 is connected to a motor control section 230 within the motor control unit 213 within the light source device 212.

One of the contacts, which are connected to the motor control section 230, of the respective four (4) switches U, D, R and L cooperating with each other to form the curvature switch 210 is pulled up by a resistor and a power source (not shown). The other contacts of the respective switches U, D, R and L are grounded. The switches U, D, R and L output an ON signal of "L" to the motor control section 230 when the switches are turned ON.

The motor control section 230 receives a signal from the curvature switch 210, to activate the corresponding direction of a motor driver 231 during a period of time that the "L" signal is received. The motor driver 231 is brought to a structure driving a motor 232 within the electronic endoscope 201 during being activated.

Next, the gas-feed/water-feed switch 208 is a two-stage switch. At a first stage, the gas feed switch AI is turned ON. At further depression, the gas feed switch AI and a water feed switch WA are turned ON. These switches also issue "L" signals, respectively, when the switches are turned ON, similarly to the curvature switch 210. The gas feed switch AI is connected to a gas feed control section 233. The gas feed control section 233 drives a gas feed pump 234 when the gas feed control section 233 receives the "L" signal. The gas feed pump 234 feeds gas to a gas feed line (not shown) of the electronic endoscope 201 through a change-over valve 235.

Figure 30:
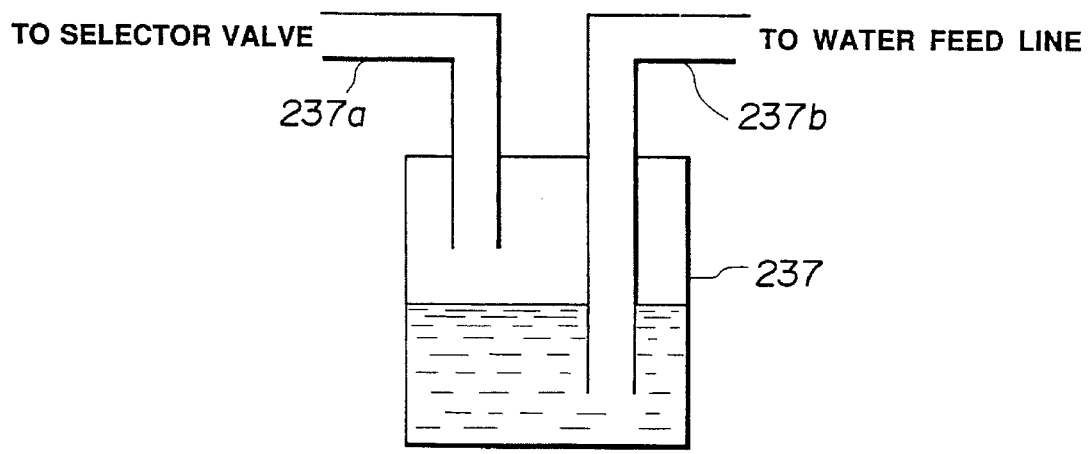

Next, the water feed switch WA is connected to a water feed control section 236. When the water feed control section 236 receives the "L" signal, the water feed control section 236 actuates the change-over valve 235, to introduce air from the gas feed pump 234, into a water tank 237. Here, the water tank 237 is a sealed container filled therein with water as shown in FIG. 30. The sealed container comprises a gas feed tube 237a from the change-over valve 235, which is arranged on the water surface, and a water feed tube 237b connected to the water feed line (not shown) within the electronic endoscope 201, which is arranged below the water surface.

Air introduced from the gas feed tube 235 depresses the water surface. The depressed water passes through the water feed tube 237b, and is introduced into the water feed line, to execute water feed.

Next, the suction switch 209 is turned ON to also issue the "L" signal, similarly to the curvature switch 210 and the gas-feed/water-feed switch 208. A suction control section 238 connected to the suction switch 209 drives a suction pump 239 when the suction control section 238 receives the "L" signal. The suction pump 239 executes suction through a suction line (not shown) within the electronic endoscope 201.

Further, the output signals from the gas-feed/water-feed switch 208 and the suction switch 209 are also inputted to a three-input AND circuit 240. The AND circuit 240 sends a signal to the motor control section 230. The motor control section 230 is brought to a circuit arrangement in which, when the motor control section 230 receives an "L" signal from the AND circuit 240, the motor control section 230 does not activate the motor driver 231, even if the motor drive section 230 receives the "L" signal from the curvature switch 210.

Next, functions of the curvature switch 210, the gas-feed/water-feed switch 208 and the suction switch 209 will be described.

When the switch U for executing curvature operation in an Up direction of the curvature switch 210 of the electronic endoscope 201 in FIG. 29 is depressed, the "L" signal is sent to the motor control section 230 within the light source device 212 with respect to a control end in the Up direction. Then, the motor control section 230 activates the Up direction of the motor driver 231. The motor driver 231 drives the motor 232 within the electronic endoscope 201, during being activated. The motor 232 rotates the sprocket 219 illustrated in FIG. 26, through a drive gear (not shown), to move the chain 221 engaged with the sprocket 219.

The chain 221 moves the angled wire 223 through the chain end 222. The angled wire 223 pulls or draws the forward-end arrangement portion 205 of the curvature section 206 in FIG. 24, whereby the curvature section 206 is curved in the Up direction (in a direction opposite to the light source device 212 in FIG. 24).

Here, when a finger which depresses the switch U executing curvature operation in the Up direction of the curvature switch 210, an "H" signal is sent with respect to a control end of the motor control section 230 in the Up direction. Then, the motor driver 231 stops activation in the Up direction. The motor 232 stops causing curvature of the curvature section 206 in the Up direction to also stop.

Next, when the first stage of the gas-feed/water-feed switch 208 is turned ON in FIG. 29, a condition is brought to a gas-feed condition, and only the gas feed switch AI is turned ON. Then, the "L" signal is sent to the gas feed control section 233 within the light source device 212. When the gas feed control section 233 receives the "L" signal, the gas feed control section 233 drives the gas feed pump 234. The gas feed pump 234 executes gas feed to a gas feed line (not shown) of the electronic endoscope 201 through the change-over valve 235.

Moreover, when the gas-feed/water-feed switch 208 is further turned ON up to the second stage, a condition is brought to the water feed condition, and the gas feed switch AI and the water feed switch WA are turned ON. When the water feed switch WA is turned ON, the "L" signal is sent to the water feed control section 236. When the water feed control section 236 receives the "L" signal, the water feed control section 236 drives the change-over valve 235 so that gas feed from the gas feed pump 234 is delivered to the water tank 237, not to the gas feed line.

Then, the air is introduced into the water tank 237 from the gas feed tube 237a in FIG. 30. Because of the inflow air, water is depressed. The depressed water is sent to the water feed line through the water feed tube 237b.

When the gas-feed/water-feed switch 208 is turned OFF, the "H" signal is sent to the gas feed control section 233 and the water feed control section 236. When the gas feed control section 236 receives the "H" signal, driving of the gas feed pump 234 stops. Moreover, when the water feed control section 236 receives the "H" signal, the water feed control section 236 brings the change-over valve 235 to a condition under which the gas feed pump 234 and the gas feed line are connected to each other. In this manner, gas-feed/water-feed stops.

Next, when the suction switch 209 is turned ON, the "L" signal is sent to the suction control section 238. Then, the suction control section 238 drives the suction pump 239. The suction pump 239 executes suction through a suction line.

When the curvature switch 210 is depressed in the middle of depression of the gas-feed/water-feed switch 208 or the suction switch 209, the motor control section 230 receives the "L" signal from the AND circuit 240, because signal lines from the gas-feed/water-feed switch 208 and the suction switch 209 are so connected as to be inputted to the motor control section 230, through the three-input AND circuit 240, so as not to drive the motor driver 231. Accordingly, the motor 232 is not driven, and the curvature section 206 is also not curved.

According to the sixth embodiment functioning in this manner, even if the curvature switch 210 is erroneously depressed at gas-feed/water-feed and suction, the curvature section 206 is not curved so that safety can be secured.

A seventh embodiment of the invention will next be described with reference to FIGS. 31 and 32.

The present embodiment is one having a changed curvature switch 210 (a type in which curvature is applied during a period of time the curvature switch 210 is depressed) according to the sixth embodiment, to a type in which a curvature switch position (angle) and a curvature angle of the curvature section correspond to 1 to 1.

Differences from the sixth embodiment are four points including a) a type of the curvature switch, b) a control system of a motor control section, c) A/D converting means being provided in front of the motor control section, and d) an encoder being provided on the motor. Others are the same as the first embodiment. The same or identical reference numerals are applied to parts or elements the same as those of the first embodiment, and the description thereof will be omitted.

Figure 31:
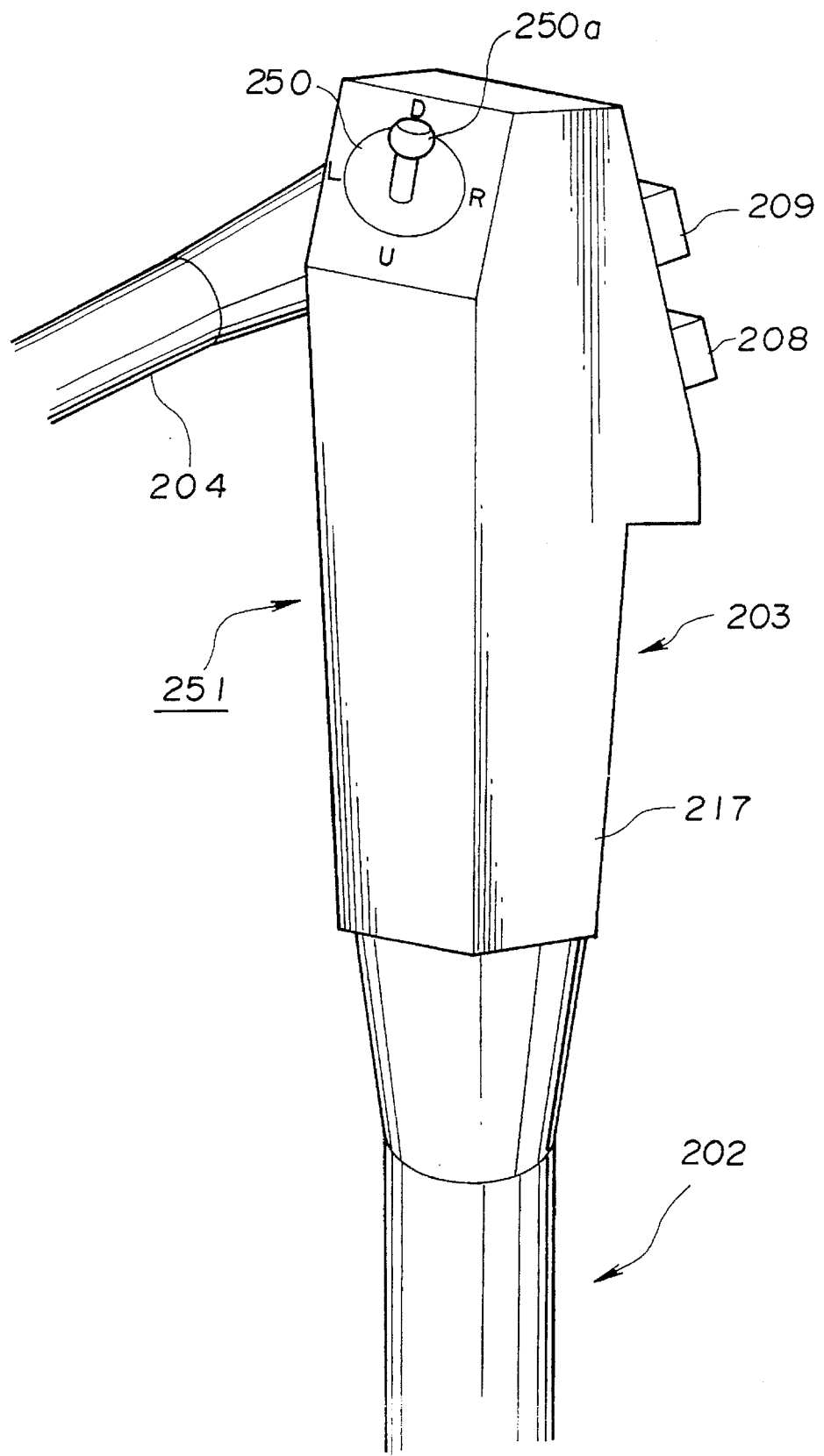
FIGS. 31 to 32 relate to a seventh embodiment of the invention, FIG. 31 being a perspective view showing an operating section formed with operating means such as a curvature switch or the like in the seventh embodiment of the invention.

In FIG. 31, a curvature switch 250 is a switch in which a shaft portion 250a is capable of being tilted or inclined in U, D, R and L (upper, lower, left-hand and right-hand) directions, and is a switch for executing curvature operation of the curvature section 206 of the inserting section 202. As shown in FIG. 32, a trimmer resistor is arranged within the curvature switch 250. An inclined angle of the shaft portion 250a is converted to an electric signal (voltage). The converted electrical signal is transmitted to a motor control section 255 through an A/D converter within a light source device 212 to be described subsequently.

Furthermore, a position of the curvature switch 250 resides in a direction of a thumb of an operator with respect to a grasping portion 217 grasped by the operator when the operator grasps the grasping portion 217. Operation of the curvature switch 250 is so arranged as to be capable of being operated by the thumb.

Reversely, a gas-feed/water-feed switch 208 and a suction switch 209 are located in directions of the first finger and the second finger.

Figure 32:
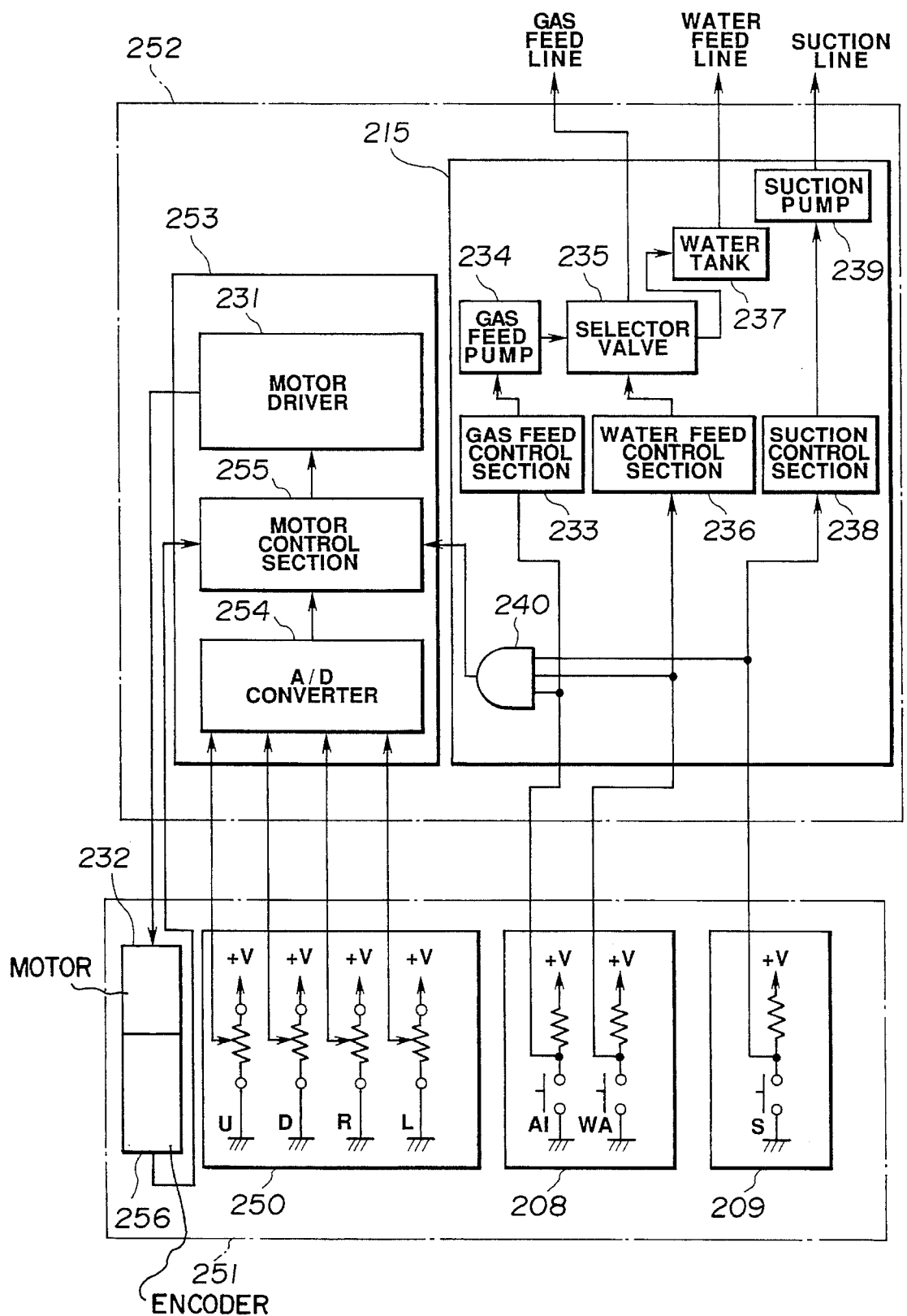

FIG. 32 is a connection view showing a relationship in control system among the curvature switch 250, the gas-feed/water-feed switch 208 and the suction switch 209.

The curvature switch 250, the gas-feed/water-feed switch 208 and the suction switch 209 are arranged within an electronic endoscope 251.

The curvature switch 250 is arranged by trimmer resistors corresponding respectively to Up, Down, Right and Left. The curvature switch 250 is connected to an A/D converter 254 within a motor control unit 253 within a light source device 252. Contacts of the trimmer resistors within the curvature switch 250, on the side of the A/D converter 254 are pulled up by an electric source (not shown). Further, other contacts are grounded.

By the fact that the shaft portion 250a in FIG. 31 is inclined, the trimmer resistors send voltage of 0–+V to the A/D converter 254. The A/D converter 254 has a function of converting voltage that is an analog quantity to a digital quantity, and is connected to the motor control section 255 so as to transmit data after conversion to the motor control section 255.

The motor control section 255 functions to control a motor driver 231 such that the digital quantities of U, D, R and L and a quantity of rotation of the encoder provided on a motor to be described subsequently are brought to the same as each other. The motor driver 231 functions to drive a motor 232 in a direction indicated by the motor control section 255, during being activated. Moreover, an encoder 256 is provided on the motor 232, to send information of the rotational angle of the motor 232 to the motor control section 255.

The gas-feed/water-feed switch 208 and the suction switch 209 are the same in arrangement as those of the sixth embodiment, and the description thereof will be omitted.

Further, the motor control section 255 is arranged in circuit such that the motor control section 255 receives an output from a three-input AND circuit 240; in a case where the output is "L" (the gas-feed/water-feed switch 208 or the suction switch 209 is under an ON-condition), control of the motor driver 231 temporarily stops; and when the output becomes "H", the motor 232 is controlled through the motor driver 231 so as to become slowly the same as the digital quantity from the A/D converter 254.

Operation will next be described.

When the curvature switch 250 is inclined toward, for example, the U direction, a resistance value of the inside trimmer resistance relating to the Up direction changes, whereby a voltage value sent to the A/D converter 254 changes. Then, the A/D converter 254 converts the voltage value after changing to a digital quantity from the analog quantity, to transmit the digital quantity to the motor control section 255. The motor control section 255 rotates the motor 232 through the motor driver 231 such that the digital quantity and a condition of the encoder 256 are coincident with each other. Thus, the curvature section 206 is curved in the Up direction by the motor 232.

Even if the curvature switch 250 is depressed during operation of the gas-feed/water-feed switch 208 or the suction switch 209, the "L" signal is inputted into the motor control section 255 through the three-input AND circuit 240 so that the motor control section 255 does not activate the motor driver 231. Thus, the curvature section 206 is not curved.

In a case where, after completion of operation of the gas-feed/water-feed switch 208 and the suction switch 209, a condition of the curvature switch 250 is changed from a condition prior to operation, the curvature section 206 is slowly curved so as to be brought to a curvature switch condition after completion of the operation.

According to the seventh embodiment functioning in this manner, even if the curvature switch 250 is erroneously moved at gas-feed/water-feed and suction, the curvature section 206 is moved slowly to a position indicated by the curvature switch 250 after completion of operation of the gas-feed/water-feed switch 208 and the suction switch 209. Accordingly, there is no case where the curvature switch 250 and the curvature section 206 do not correspond to each other.

Furthermore, since the curvature section 206 is not moved suddenly, safety is increased.

An eighth embodiment of the invention will next be described with reference to FIGS. 33 and 34.

The present embodiment is one in which a switch return motor is provided on the curvature switch of the seventh embodiment.

Differences from the seventh embodiment are three points including a) a return motor of a curvature switch being provided on a trimmer resistor, b) difference in control system of a motor control section, and c) difference in activating system of a motor driver.

Figure 33:
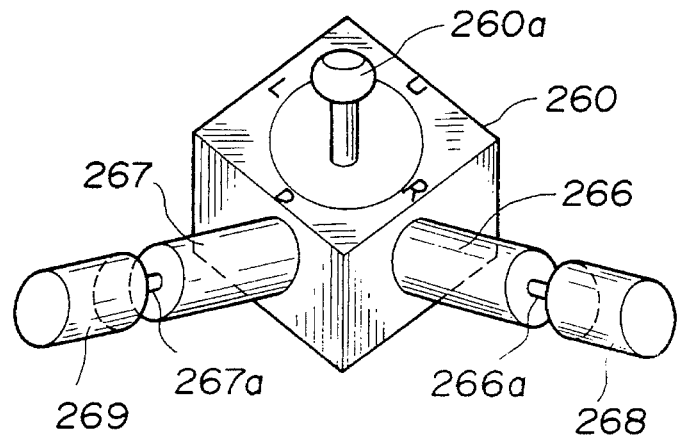
FIGS. 33 to 34 relate to an eighth embodiment of the invention, FIG. 33 being a perspective view showing a curvature switch provided with a motor for returning the curvature switch in the eighth embodiment of the invention.

A curvature switch 260 indicated in FIG. 33 provided on an electronic endoscope 261 is a switch having a shaft 260a which is capable of being inclined in U, D, R and L directions. A UD trimmer resistor 266 and an RL trimmer resistor 267, which are interlocked and rotated with the shaft 260a and which have respective rotary shafts thereof for measuring an inclined angle of the shaft 260a are provided on the side of the curvature switch 260. A UD rotary shaft 266a that is a rotary shaft of the UD trimmer resistor 266 is arranged on the UD trimmer resistor 266, while an RL rotary shaft 267a is arranged on the RL trimmer resistor 267.

A UD return motor 268 for rotating the rotary shaft 266a is connected to the UD rotary shaft 266a, while an RL return motor 269 is connected to the RL rotary shaft 267a.

Figure 34:
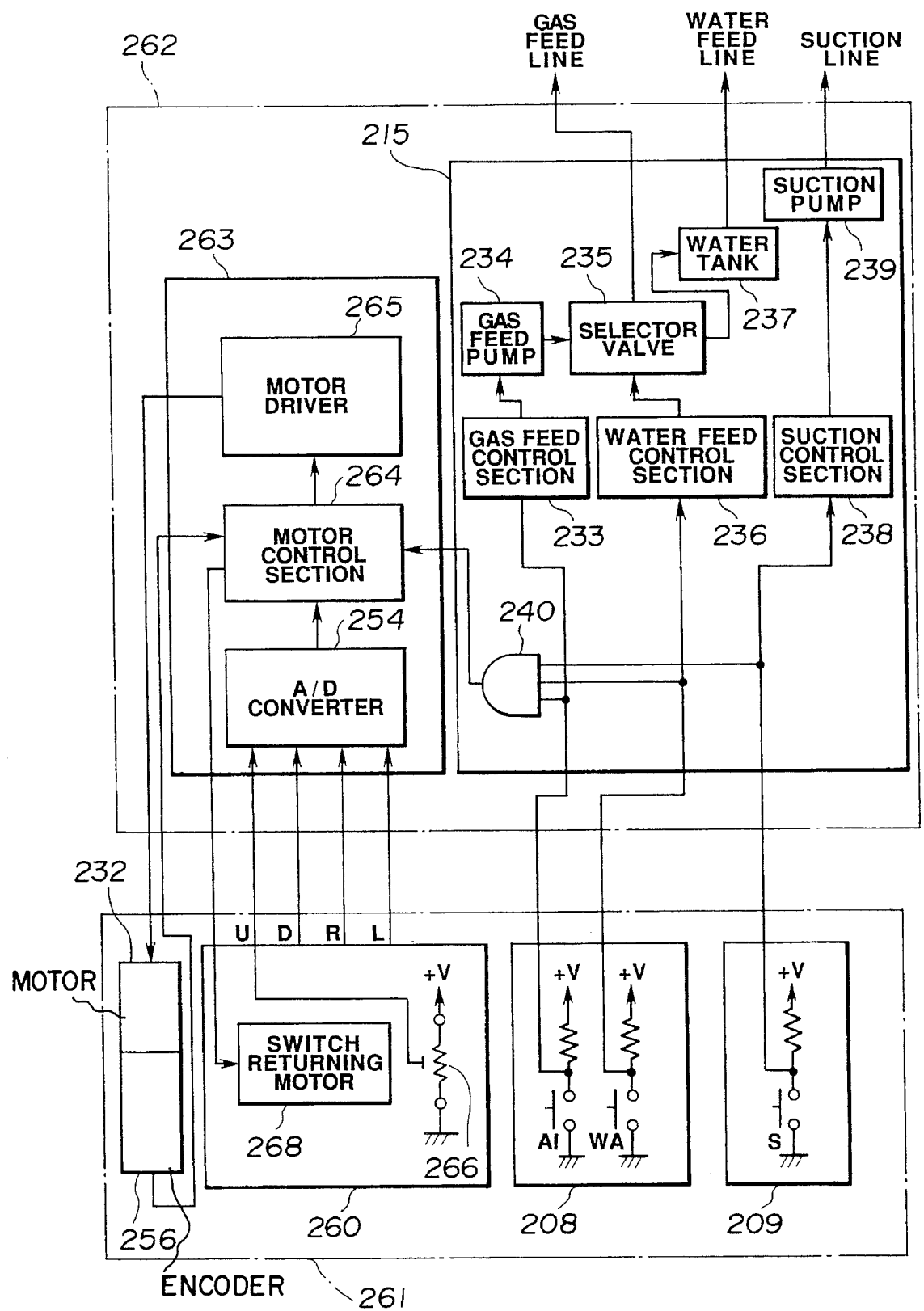

FIG. 34 shows a relationship in control system among the curvature switch 260, the gas-feed/water-feed switch 208 and the suction switch 209. In this connection, in FIG. 34, only connection in a U-direction is shown, but connections in other directions are omitted because the connections are similar in structure to each other.

Control of the UD return motor 268 is executed by a motor driver 265 and a motor control section 264 within a motor control unit 263 within a light source device 262. The motor control section 264 is brought to a circuit which activates the motor driver 265 only when the curvature switch 260 is operated simultaneously with operation of a gas-feed/water-feed switch 208 or a suction switch 209, until a quantity of rotation of an encoder 256 and a digital quantity from a trimmer resistor through an A/D converter 254 are equalized to each other after completion of operation of the gas-feed/water-feed switch 208 and the suction switch 209 to slowly rotate the motor driver 265 by the UD return motor 268.

Even if the curvature switch 260 is operated at operation of the gas-feed/water-feed switch 208 or the suction switch 209, the curvature section 206 does not move as described with reference to the sixth and seventh embodiments.

However, if the condition of the curvature switch 260 is changed from time before operation to time after operation of the gas-feed/water-feed switch 208 and the suction switch 209, the motor control section 264 activates the motor driver 265, to drive the return motor (268 or the like), to thereby move the trimmer resistor slowly such that the digital quantity sent to the A/D converter 254 is coincident with the quantity of rotation of the encoder 256, by inclination of the curvature switch 260. Thus, the curvature switch 260 is moved, and the condition of the curvature section 206 and the condition of the curvature switch 260 are made coincident with each other.

The eighth embodiment has increased safety, since the curvature section 206 does not move, in addition to the advantages of the seventh embodiment.

A ninth embodiment of the invention will next be described with reference to FIGS. 35 and 36.

The present embodiment is one in which a freeze switch and a release switch are added to the operating section of the sixth embodiment. Here, what is the freeze switch is a switch which freezes image fetching from a forward end of an inserting section to operate a freeze function capable of producing a still picture. The release switch is a switch which operates the freeze condition to produce a still picture and which indicates to photograph the still picture with respect to a camera photographing device (not shown).

Differences from the sixth embodiment are as follows: a) addition of the freeze switch, b) addition of the release switch, and c) difference in control system of a motor control section within a light source device. Others are the same as those of the sixth embodiment, and the description will be made by means of the reference numerals the same as those of the sixth embodiment.

Figure 35:
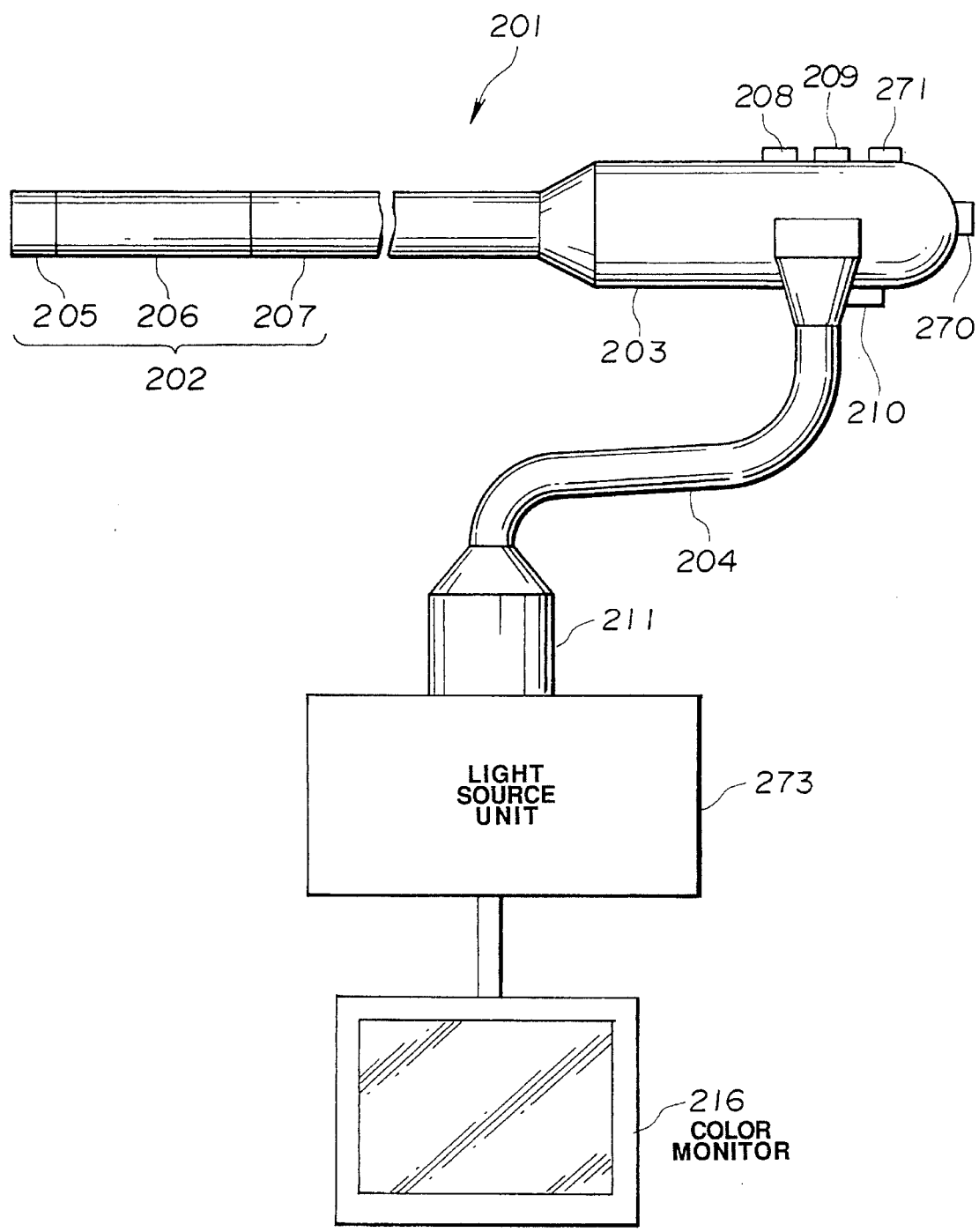
FIGS. 35 and 36 relate to a ninth embodiment of the invention, FIG. 35 being a whole or entire arrangement view showing an endoscope apparatus according to the ninth embodiment of the invention.

In FIG. 35, an operating section 203 of an electronic endoscope 201 is provided with a gas-feed/water-feed switch 208, a suction switch 209, a curvature switch 210, a freeze switch 270 and a release switch 271.

Here, an image from a side of a forward-end arrangement portion 205 of the inserting section 202 is projected on a color monitor 216 from an element of a CCD (not shown) through a universal cable 204 and a light source device 273.

As described previously, the freeze switch 270 is a switch which produces a still picture on the color monitor 216, while the release switch 271 is a switch which produces a still picture on the color monitor 216 and which indicates to photograph a still picture with respect to a camera photographing device (not shown).

Figure 36:
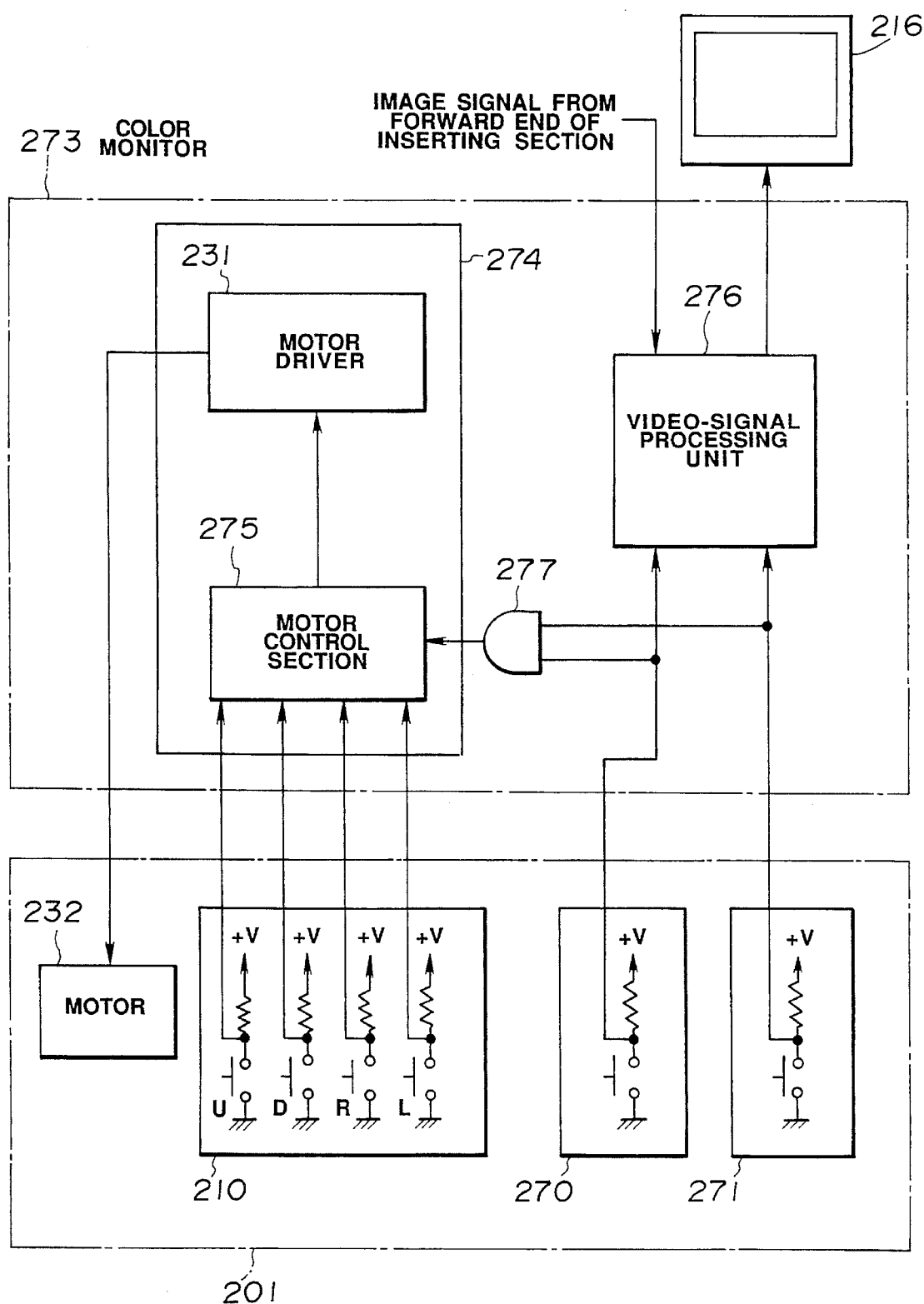

FIG. 36 shows a relationship in a control system between the curvature switch 210, and the freeze switch 270 and the release switch 271. The gas-feed/water-feed switch 208 and the suction switch 209 are the same as those of the sixth embodiment, and the description thereof will be omitted. The curvature switch 210 is a switch which generates an "L" signal at turning-ON similarly to the sixth embodiment. An output from the curvature switch 210 is connected to a motor control section 275 within a motor control unit 274 within the light source device 273.

The freeze switch 270 and the release switch 271 are also switches which generate "L" signals at turning-ON, respectively. Outputs from the respective switches are connected to a video-signal processing unit 276 within the light source device 273. The video-signal processing unit 276 has a function of processing an image signal from the forward end of the inserting section, to project an image on the color monitor 216.

Moreover, the video-signal processing unit has a function of connecting fetching of a photographing signal from the forward end of the inserting section when the video-signal processing unit receives the "L" signal from the freeze switch 270, to project a still picture on the color monitor 216, and a function to project the still picture on the color monitor 216 when the "L" signal from the release switch 271 is received, and to indicate a camera photographing device (not shown) to photograph the still picture.

Further, the outputs from the respective freeze switch 270 and release switch 271 are inputted also to a two-input AND circuit 277. An output end of the AND circuit 277 is connected to the motor control section 275. The motor control section 275 is brought to a circuit arrangement in which, when the motor control section 275 receives the "L" signal from the two-input AND circuit 277, the motor control section 275 does not activate a motor driver 231, even if the "L" signal is received from the curvature switch 210. Others are the same as those of the sixth embodiment, and the description thereof will be omitted. Operation will next be described.

When the freeze switch 270 or the release switch 271 is depressed, the "L" signal is sent to the video-signal processing unit 276 so that the still picture is displayed on the color monitor 216 and still-picture photographing is executed. The "L" signal is also sent to the motor control section 275 through the two-input AND circuit 277. Thus, inputting due to the curvature switch 210 is made invalid.

In addition to the advantages of the sixth embodiment, there are advantages that, when the freeze switch 270 and the release switch 271 are depressed, or even if the curvature switch 210 is erroneously depressed in the middle of being depressed, a curvature portion 206 does not move, and the image on the color monitor 216 corresponds to the actual condition of the curvature section 206, so that the ninth embodiment has increased safety.

A tenth embodiment of the invention will next be described with reference to FIGS. 37 to 40.

The present embodiment is an embodiment in which a seesaw switch for raising-up forceps is added to the operating section of the sixth embodiment.

Differences from the sixth embodiment include: a) addition of a forceps raising-up table to a forward-end arrangement section, b) addition of a forceps raising-up switch for operating the forceps raising-up table to an operating section, and c) addition of a forceps raising-up motor control section and a motor driver into a motor control unit within a light source device. Others are the same as those of the sixth embodiment, and the description will be made with the reference numerals the same as those in the first embodiment applied.

Figure 37:
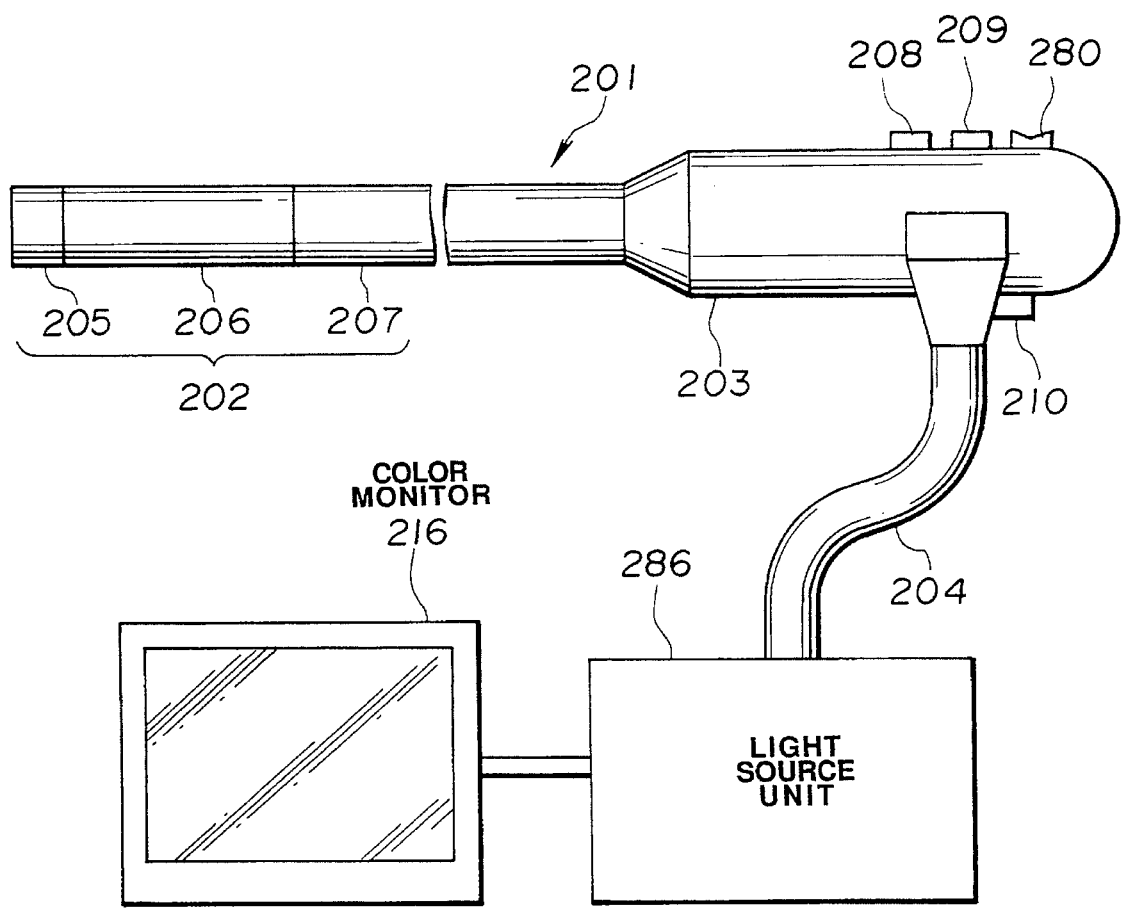
FIGS. 37 to 40 relate to a tenth embodiment of the invention, FIG. 37 being an entire arrangement view showing an endoscope apparatus according to the tenth embodiment of the invention.
Figure 38:
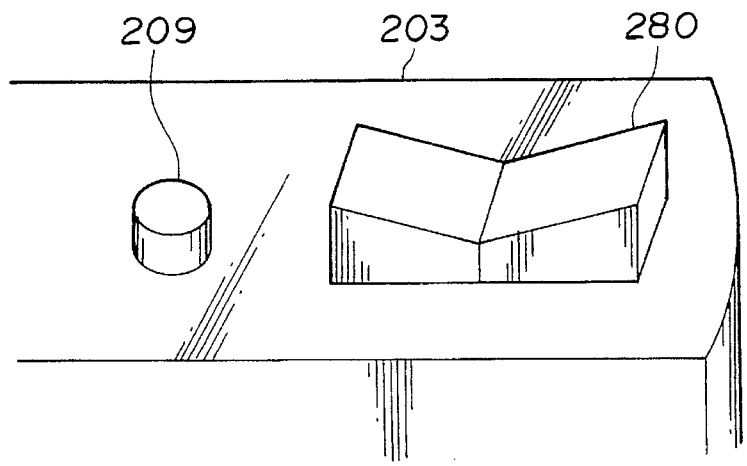

In FIG. 37, an operating section 203 of an electronic endoscope 201 is provided with a gas-feed/water-feed switch 208, a suction switch 209, a curvature switch 210, and a forceps raising-up switch 280. The forceps raising-up switch 280 is a seesaw switch as shown in FIG. 38, and is composed of two ON-OFF switches (not shown) which are arranged within the seesaw switch.

When a side B of the forceps raising-up switch 280 is depressed, a forceps raising-up table 281 to be described later is brought to a position perpendicular to a forward-end arrangement portion 205. That is, the forceps raising-up table 281 operates in a direction raising up. When the other side C of the forceps raising-up switch 280 is depressed, the forceps raising-up table 281 is brought to a position parallel to the forward-end arrangement portion 205. That is, the forceps raising-up table 281 is so arranged as to operate in a lying direction.

Figure 39:
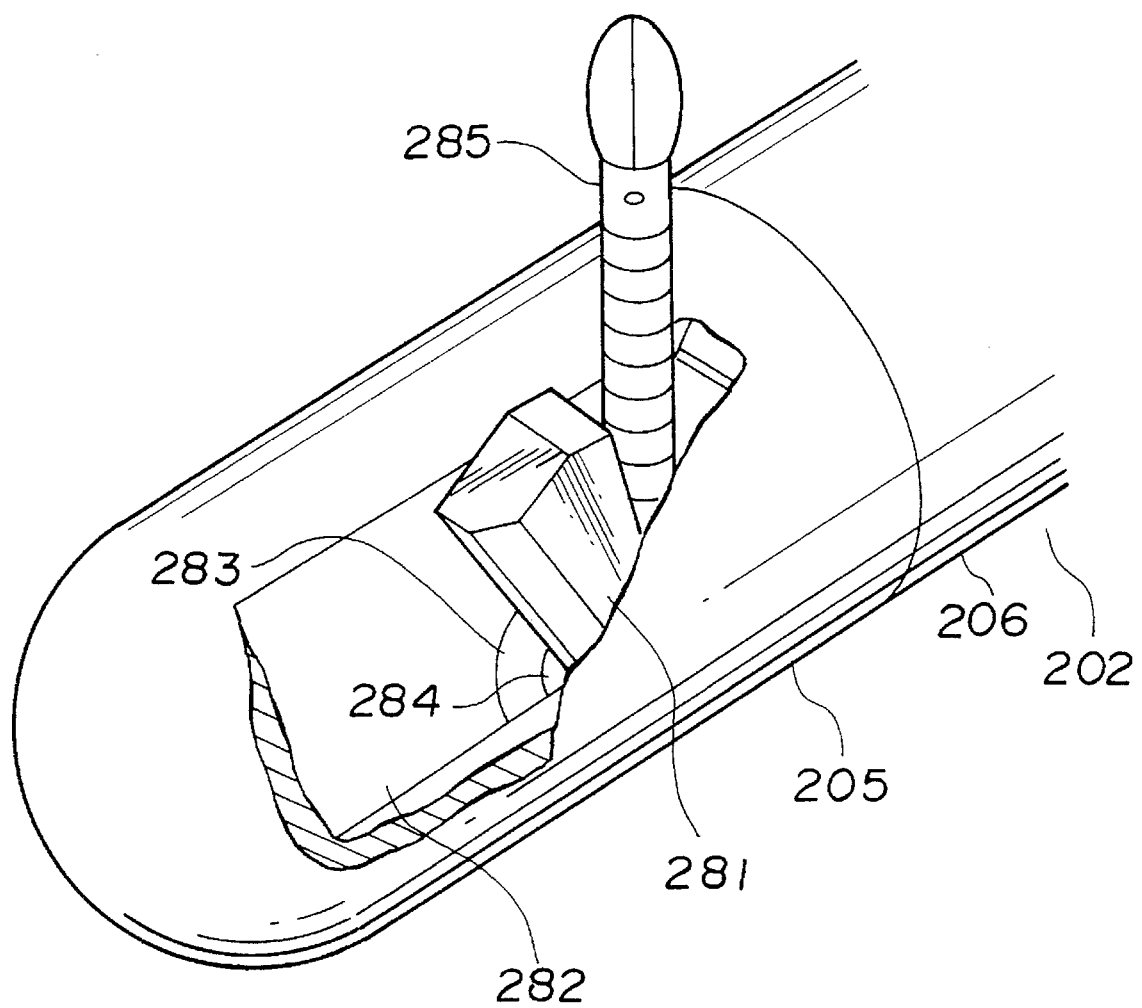

FIG. 39 shows a structure of the forward-end arrangement portion 205. The forward-end arrangement portion 205 is formed with an accommodating or receiving chamber 282. The receiving chamber 282 is provided with a forceps raising-up motor 283. The forceps raising-up table 281 for changing a derivative direction of a treatment instrument 285 is fixedly mounted on a rotary shaft 284 of the forceps raising-up motor 283. That is, when the forceps raising-up motor 283 is energized, the rotary shaft 284 is rotated. Accompanied with the rotation, the forceps raising-up table 281 is also operated so as to be brought to parallel–vertical conditions with respect to the forward-end arrangement portion 5.

Figure 40:
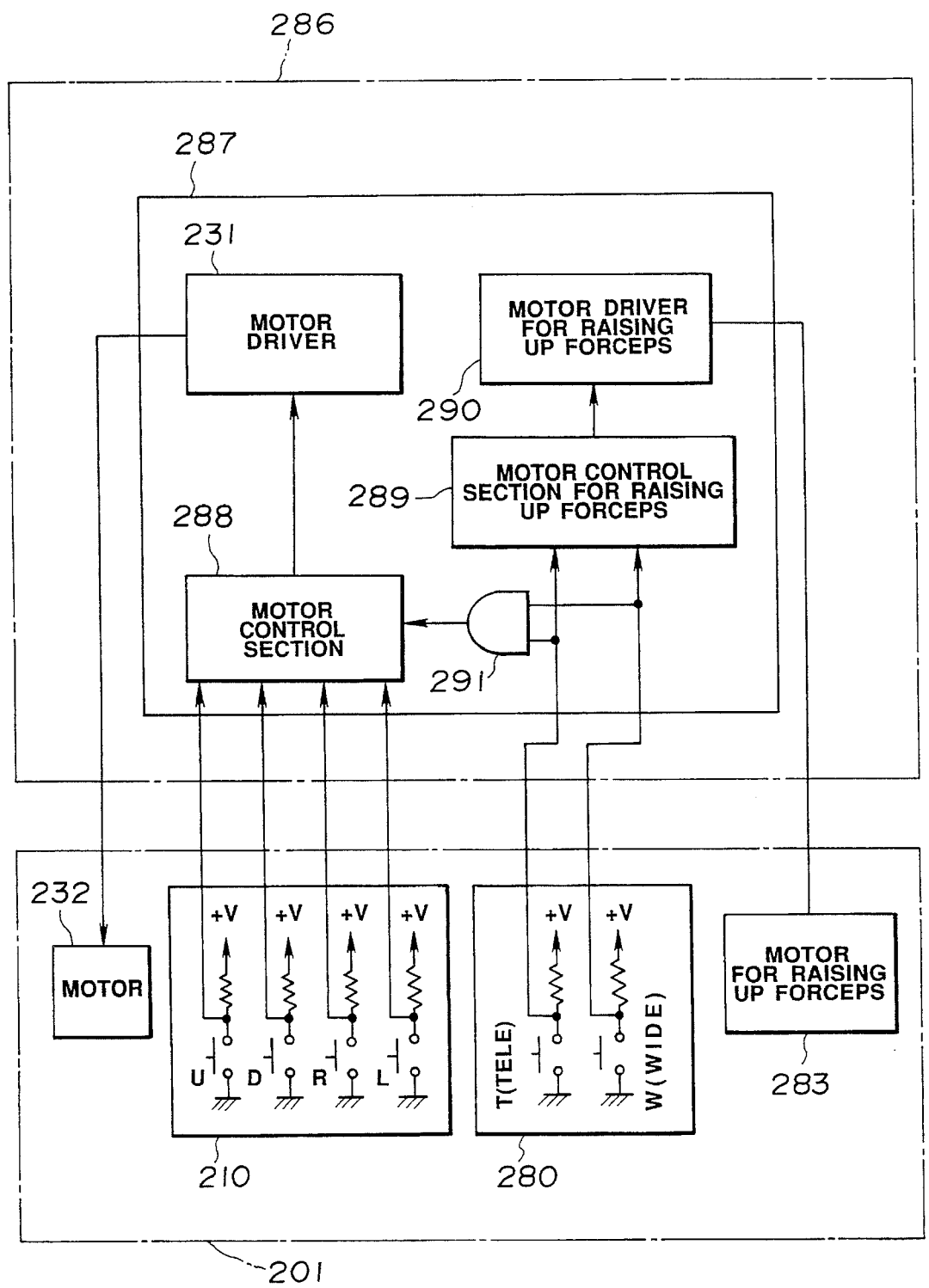

FIG. 40 shows a relationship in a control system between the curvature switch 210 and the forceps raising-up switch 280. The gas-feed/water-feed switch 208 and the suction switch 209 are the same as those of the sixth embodiment, and the description thereof will be omitted. The curvature switch 210 is a switch which issues an "L" signal at turning ON, similarly to the sixth embodiment. An output from the switch is connected to a motor control section 288 located within a motor control unit 287 which is, in turn, located within a light source device 286.

The forceps raising-up switch 280 is also a switch which generates the "L" signal at turning ON. An output from the switch is connected to a forceps raising-up motor control section 289 within the motor control unit 287. When the forceps raising-up motor control section 289 receives the "L" signal from a B (vertical direction) switch or a C (parallel direction) switch within the forceps raising-up switch 208, a forceps raising-up motor driver 290 is activated. The forceps raising-up motor driver 290 rotates a forceps raising-up motor 283 during activation of the forceps raising-up motor driver 290, whereby the forceps raising-up table 281 is moved so as to be brought to the parallel N vertical position in accordance with the switch condition.

Furthermore, the output from the forceps raising-up switch 280 is also inputted to a two-input AND circuit 291, and an output end of the forceps raising-up switch 280 is connected to the motor control section 288. The motor control section 288 is brought to a circuit arrangement in which, when the motor control section 288 receives the "L" signal from the two-input AND circuit 291, the motor control section 288 does not activate a motor driver 231 even if the motor control section 288 receives the "L" signal from the curvature switch 210. Others are the same in arrangement as the sixth embodiment of the invention, and the description thereof will be omitted.

The operation will next be described. When the B side of the forceps raising-up switch 280 is depressed, the "L" signal is sent to the forceps raising-up motor control section 289 so that the forceps raising-up table 281 is moved vertically, and the "L" signal is sent to the motor control section 288 through the two-input AND circuit 291 so that inputting due to the curvature switch 210 is made invalid.

In addition to the advantages of the sixth embodiment, there can be produced advantages that, even if the curvature switch 210 is erroneously depressed when the forceps raising-up switch 280 is depressed, or in the middle of being depressed, a curvature portion 206 is not moved so that the tenth embodiment is safe.

An eleventh embodiment of the invention will next be described with reference to FIGS. 41 to 45.

The present embodiment is one in which a zoom switch is added to the operating section of the sixth embodiment. Here, what is the zoom switch is a switch in which a moving lens of the zoom lens serving as an objective lens system provided at the forward end of the inserting section is retracted and advanced in an optical axis direction to adjust the moving lens to a TELE condition and a WIDE condition.

Differences from the sixth embodiment include: a) provision of a zoom lens mechanism serving as an objective lens system, within a forward-end arrangement portion, b) addition of a zoom switch for operating the zoom lens mechanism, to an operating section, and c) addition of a zoom motor control section and a motor driver within a motor control unit within a light source device. Others are the same as those of the sixth embodiment, and the description will be made to parts and elements to which the reference numerals the same as those in the sixth embodiment are applied.

Figure 41:
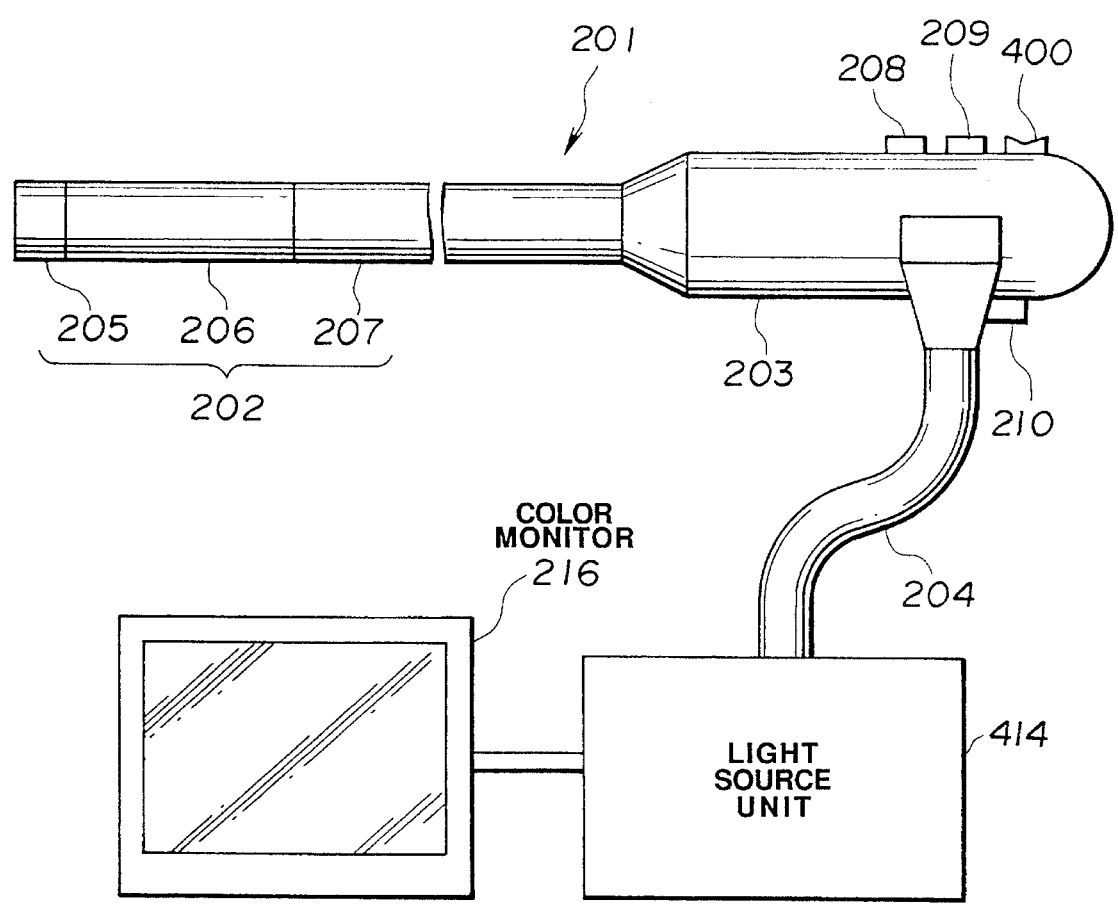
FIGS. 41 to 45 relate to an eleventh embodiment of the invention, FIG. 41 being an entire arrangement view showing an endoscope apparatus according to the eleventh embodiment of the invention.
Figure 42:
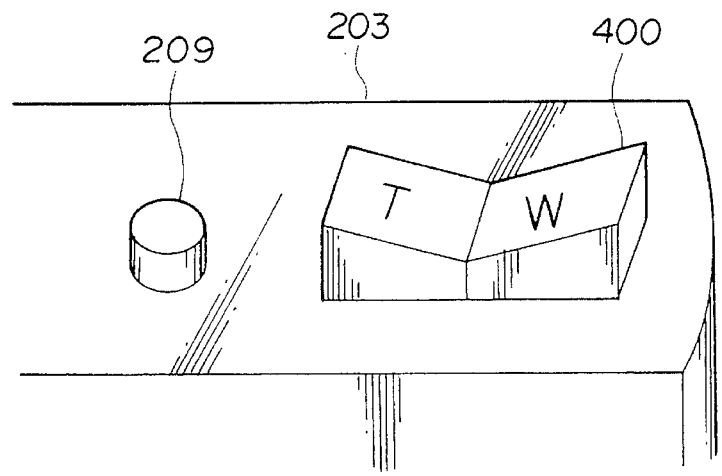

In FIG. 41, an operating section 203 of an electronic endoscope 201 is provided with a gas-feed/water-feed switch 208, a suction switch 209, a curvature switch 210, and a zoom switch 400. As shown in FIG. 42, the zoom switch 400 is brought to a seesaw switch, and is arranged by two ON-OFF switches (not shown) which are arranged within the seesaw switch. The zoom lens mechanism is so arranged as to be moved such that, when a W side is depressed, an image from the forward end is brought to WIDE, while, when a T side is depressed, the image from the forward end is brought to TELE.

Figure 43:
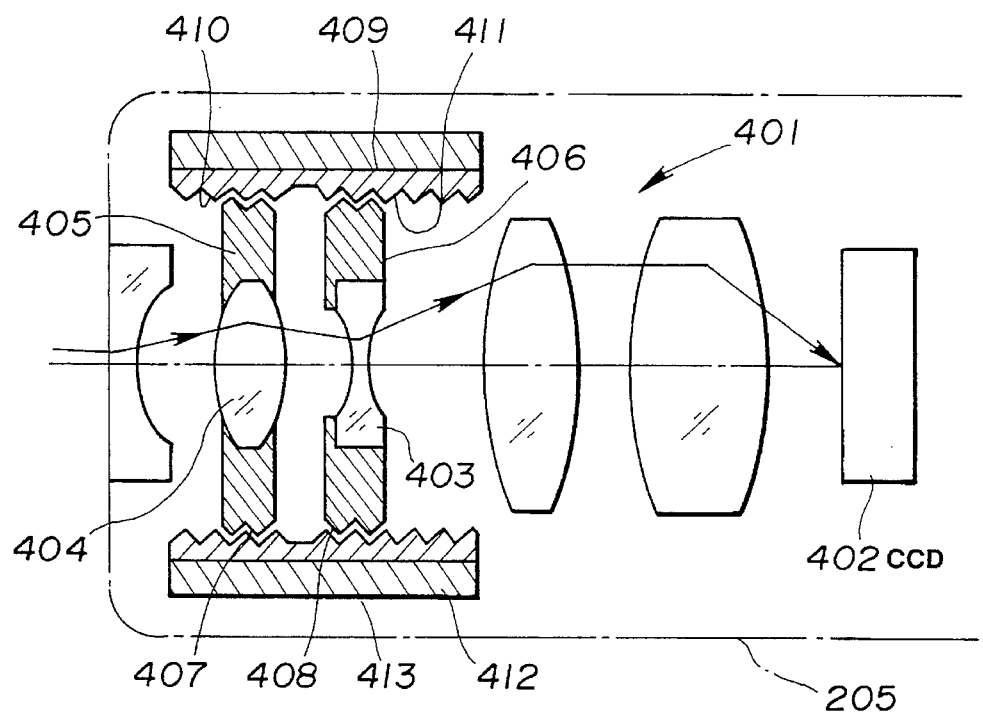

FIG. 43 shows a structure of the forward-end arrangement portion 205. The forward-end arrangement portion 205 is arranged such that a boring bore is bored axially and opens in the forward end surface. The boring bore is provided with an objective lens system 401 which extends axially. A CCD (solid-state image pickup element) 402, for example, is arranged further within the objective lens system 401 in opposed relation thereto.

A variator 403 and a compensator 404 serving, for example, as moving lenses located adjacent to the proximal end of the forward-end arrangement portion 205 are provided within the objective lens system 401. The variator 403 and the compensator 404 are mounted such that respective peripheral portions are fitted in the lens frames 405 and 406, respectively.

Here, the compensator 404 is fitted in a one lens frame 405. The outer peripheral surface of the lens frame 405 is formed with a helical uneven or irregular portion 407 over an optical axis direction.

Moreover, the variator 403 is fitted in an other lens frame 406. An outer peripheral surface of the lens frame 406 is provided with an irregular portion 408 formed into a helical configuration in a direction, for example, opposite to the irregular portion 407.

A substantially cylindrical rotor 409 is provided on the sides of the outer peripheries of the respective lens frames 405 and 406. The rotor 409 has an inner surface thereof which is provided with irregular portions 410 and 411 which are threadedly engaged respectively with the lens frames 405 and 406. These irregular portions are arranged such that the rotor 409 is normally rotated whereby the variator 403 and the compensator 404 approaches each other in the optical-axial direction, while the rotor 409 is reversely rotated whereby the variator 403 and the compensator 404 are spaced away from each other in the optical axial direction.

The rotor 409 has an outer portion thereof which is covered with a stator 412, and cooperates with the stator 412 and the rotor 409 of the rotary shaft thereof to form an ultrasonic motor 413. That is, when the rotor 409 of the ultrasonic motor 413 is rotated normally, the variator 403 and the compensator 404 approach each other. Thus, a WIDE condition is produced.

Figure 44:
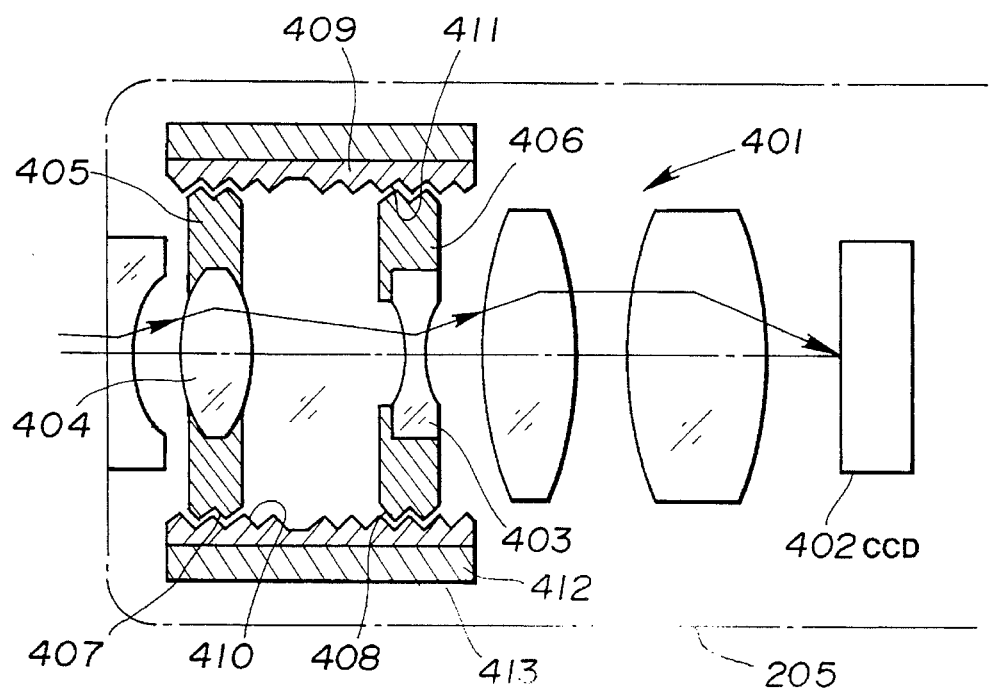

FIG. 44 shows the TELE condition in which the rotor 409 is reversely rotated, and the variator 403 and the compensator 404 are spaced away from each other.

Figure 45:
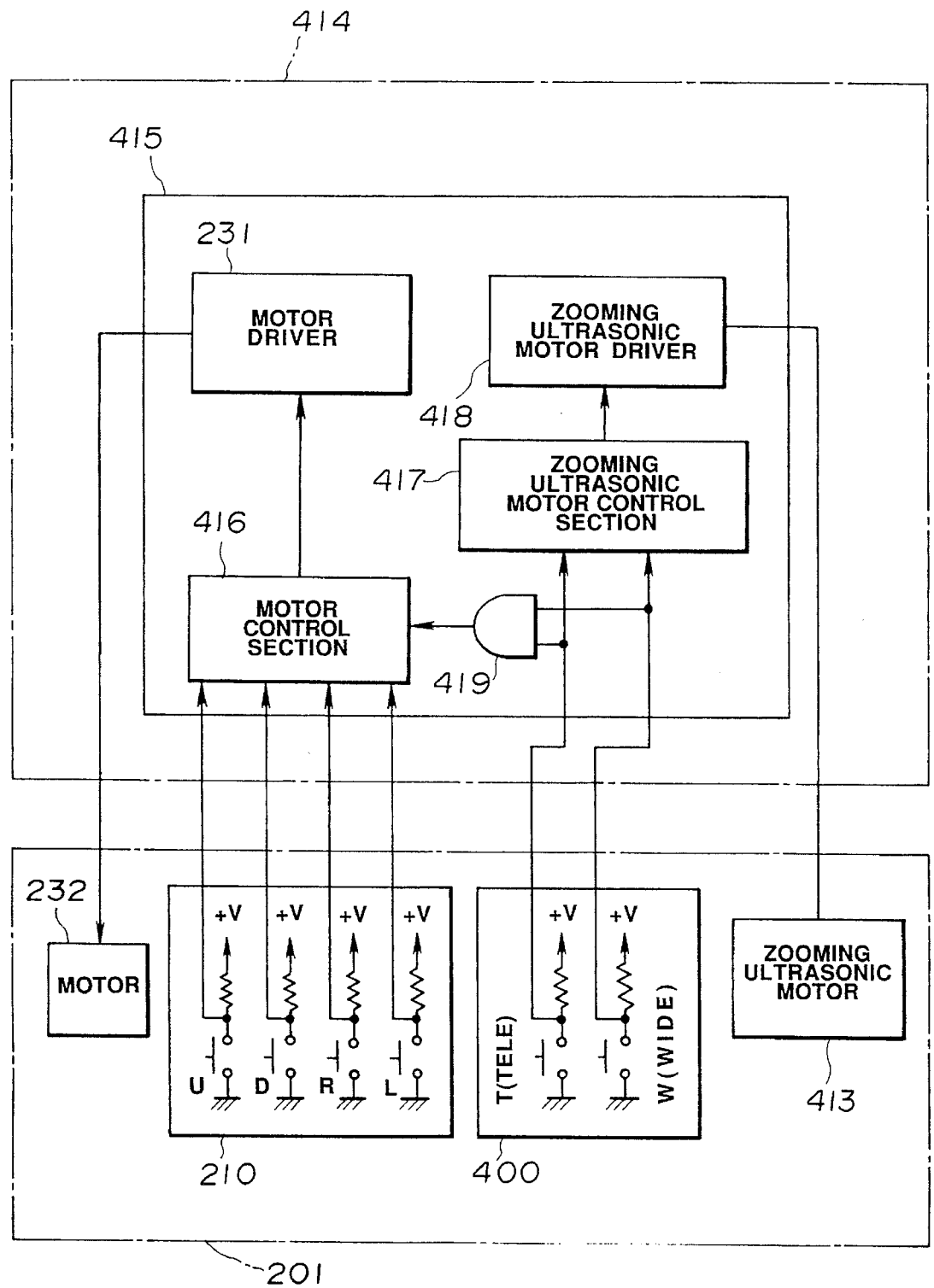

FIG. 45 shows a relationship in control system between the curvature switch 210 and the zoom switch 400. The gas-feed/water-feed switch 208 and the suction switch 209 are the same as those of the sixth embodiment, and the description thereof will be omitted.

The curvature switch 210 is a switch which generates an "L" signal upon turning ON similarly to the sixth embodiment. An output therefrom is connected to a motor control section 416 within a motor control unit 415 within a light source device 414.

The zoom switch 400 is also a switch which generates the "L" signal upon turning ON. An output therefrom is connected to a zoom ultrasonic motor control section 417 within the motor control unit 415. When the zoom ultrasonic motor control section 417 receives the "L" signal from the W (WIDE) switch or the (TELE) switch within the zoom switch 400, the zoom ultrasonic motor control section 417 activates the zoom ultrasonic motor driver 418.

During the period of time the zoom ultrasonic motor driver 418 is activated, a zoom ultrasonic motor 413 is rotated whereby the variator 403 and the compensator 404 in FIG. 43 are so moved as to be brought to WIDE–TELE in accordance with the switch condition.

Further, an output from the zoom switch 400 is also inputted to a two-input AND circuit 419. An output end thereof is connected to the data control section 416. The motor control section 416 is brought to a circuit arrangement in which, when the motor control section 416 receives the "L" signal from the two-input AND circuit 419, the motor control section 416 does not activate a motor driver 231 even if the "L" signal is received from the curvature switch 210. Others are the same as those of the sixth embodiment, and the description thereof will be omitted.

Operation will next be described. When a W side of the zoom switch 400 is depressed, the "L" signal is sent to the zoom ultrasonic motor control section 417 so that the variator 403 and the compensator 404 approach each other. Thus, an image from the forward end of the inserting section is brought to the WIDE condition. The "L" signal is sent to the motor control section 416 through the two-input AND circuit 419 so that inputting due to the curvature switch 210 is made invalid.

According to the present embodiment, in addition to the advantages produced by the sixth embodiment, there can be produced advantages where a curvature portion 206 does not move even if the curvature switch 210 is erroneously depressed when the zoom switch 400 is depressed or in the middle of being depressed so that the present embodiment has increased safety.

A twelfth embodiment of the invention will next be described with reference to FIGS. 46 and 47.

The present invention is one in which the forceps raising-up switch of the tenth embodiment is arranged in place of the angle switch of the sixth embodiment. Others are the same as those of the previous embodiments, and the description thereof will be made with the same reference numerals applied.

Figure 46:
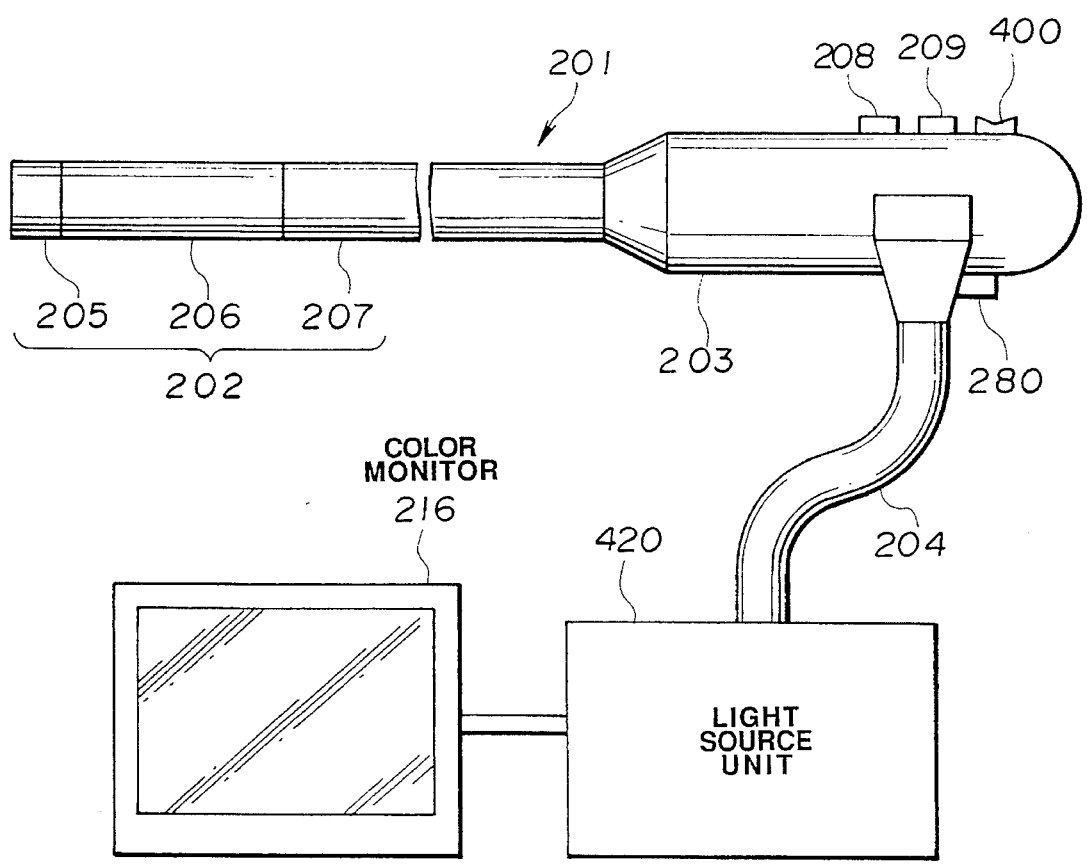
FIGS. 46 and 47 relate to a twelfth embodiment of the invention, FIG. 46 being a whole or entire arrangement view showing an endoscope apparatus according to the twelfth embodiment of the invention.

In FIG. 46, an operating section 203 of an electronic endoscope 201 is provided with a gas-feed/water-feed switch 208, a suction switch 209, a zoom switch 400 and a forceps raising-up switch 280. Further, the zoom switch 400 and the forceps raising-up switch 280 are arranged in an opposed direction with the operating section 203 put therebetween.

Figure 47:
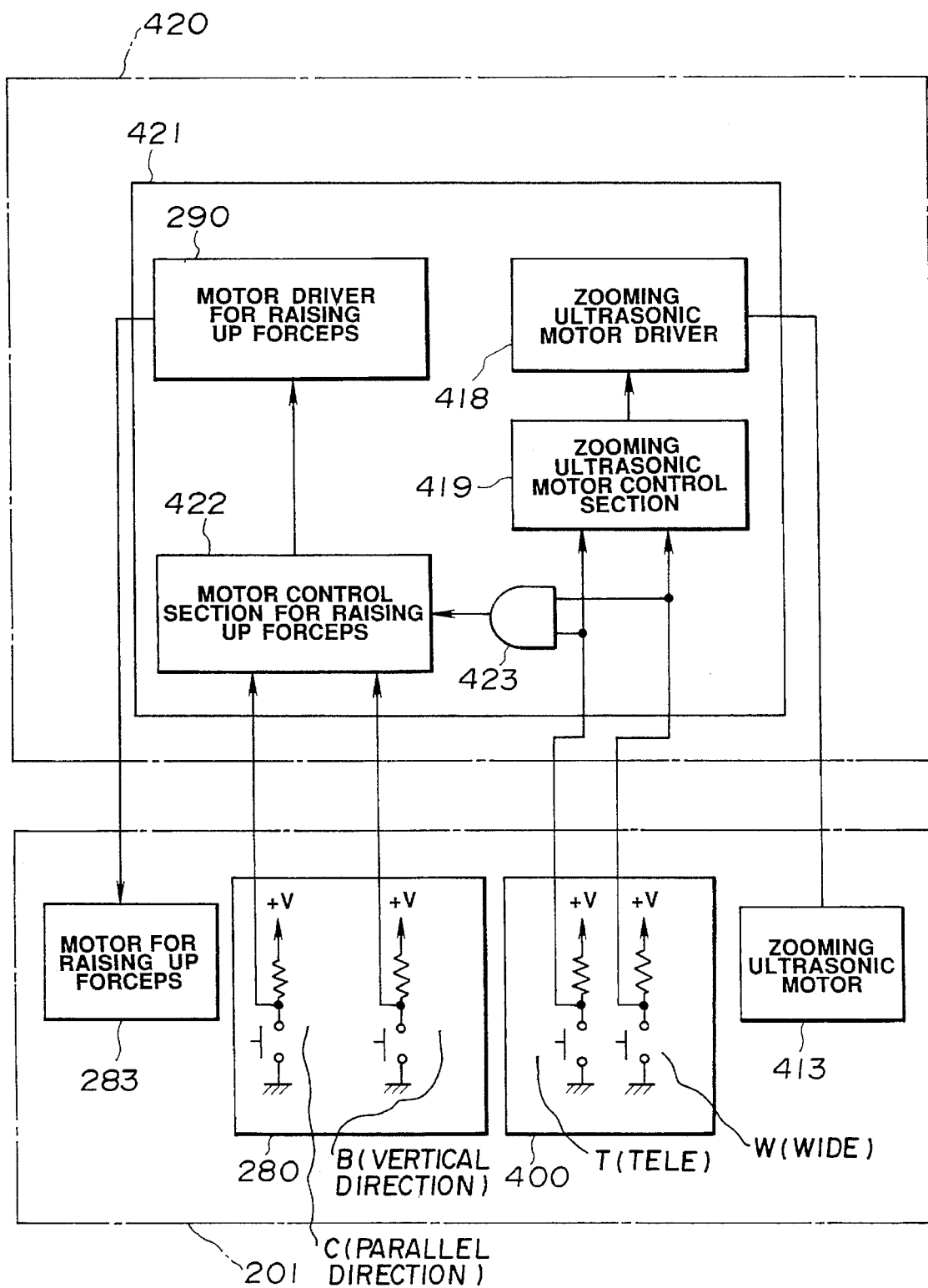

FIG. 47 shows a relationship in control system between the zoom switch 400 and the forceps raising-up switch 280.

The forceps raising-up switch 280 is a switch which generates an "L" signal upon turning ON. An output therefrom is connected to a forceps raising-up motor control section 422 within a motor control unit 421 within a light source device 420. The forceps raising-up motor control section 422 drives a forceps raising-up motor driver 290, when the forceps raising-up motor control section 422 receives the "L" signal from a B (vertical direction) or C (parallel direction) switch within the forceps raising-up switch 280.

The forceps raising-up motor driver 290 is arranged such that, during being activated, the forceps raising-up motor driver 290 rotates a forceps raising-up motor 283, whereby the forceps raising-up table moves according to the switch condition.

The zoom switch 400 is also a switch which generates the "L" signal upon turning ON. An output therefrom is connected to a zoom ultrasonic motor control section 417 within the motor control unit 421.

The zoom ultrasonic control section 417 activates a zoom ultrasonic motor driver 418 when the zoom ultrasonic control section 417 receives the "L" signal from the T (TELE) switch or the W (WIDE) switch within the zoom switch 400. The zoom ultrasonic motor driver 418 is arranged such that, during activation, the zoom ultrasonic motor driver 418 rotates a zoom ultrasonic motor 413, whereby the zoom lens moves in accordance with the switch condition.

Further, an output from the zoom switch 400 is also inputted to a two-input AND circuit 423. An output end therefrom is connected to the forceps raising-up motor control section 422. The forceps raising-up motor control section 422 is brought to a circuit arrangement in which, when the forceps raising-up motor control section 422 receives the "L" signal from the two-input AND circuit 423, the forceps raising-up motor control section 422 does not activate the forceps raising-up motor driver 290, even if the forceps raising-up motor control section 422 receives the "L" signal from the forceps raising-up switch 280. Operation of the present embodiment will next be described.

When the W (WIDE) side of the zoom switch 400 is depressed, the "L" signal is sent to the zoom ultrasonic motor control section 417, the zoom lens is so moved as to be brought to the WIDE condition, and the "L" signal is sent to the forceps raising-up motor control section 422 through the AND circuit 423. Thus, inputting due to the forceps raising-up switch 280 is made invalid.

According to the twelfth embodiment of the invention, safety can be secured because, even if the forceps raising-up switch 280 is erroneously depressed when the zoom switch 400 is depressed or in the middle of being depressed, the forceps raising-up table 281 does not move.

In connection with the above, in the above-described embodiment, the drive means may not be the motor, but may be one which utilizes hydraulic pressure, a shape memory alloy or the like.

Figure 48:
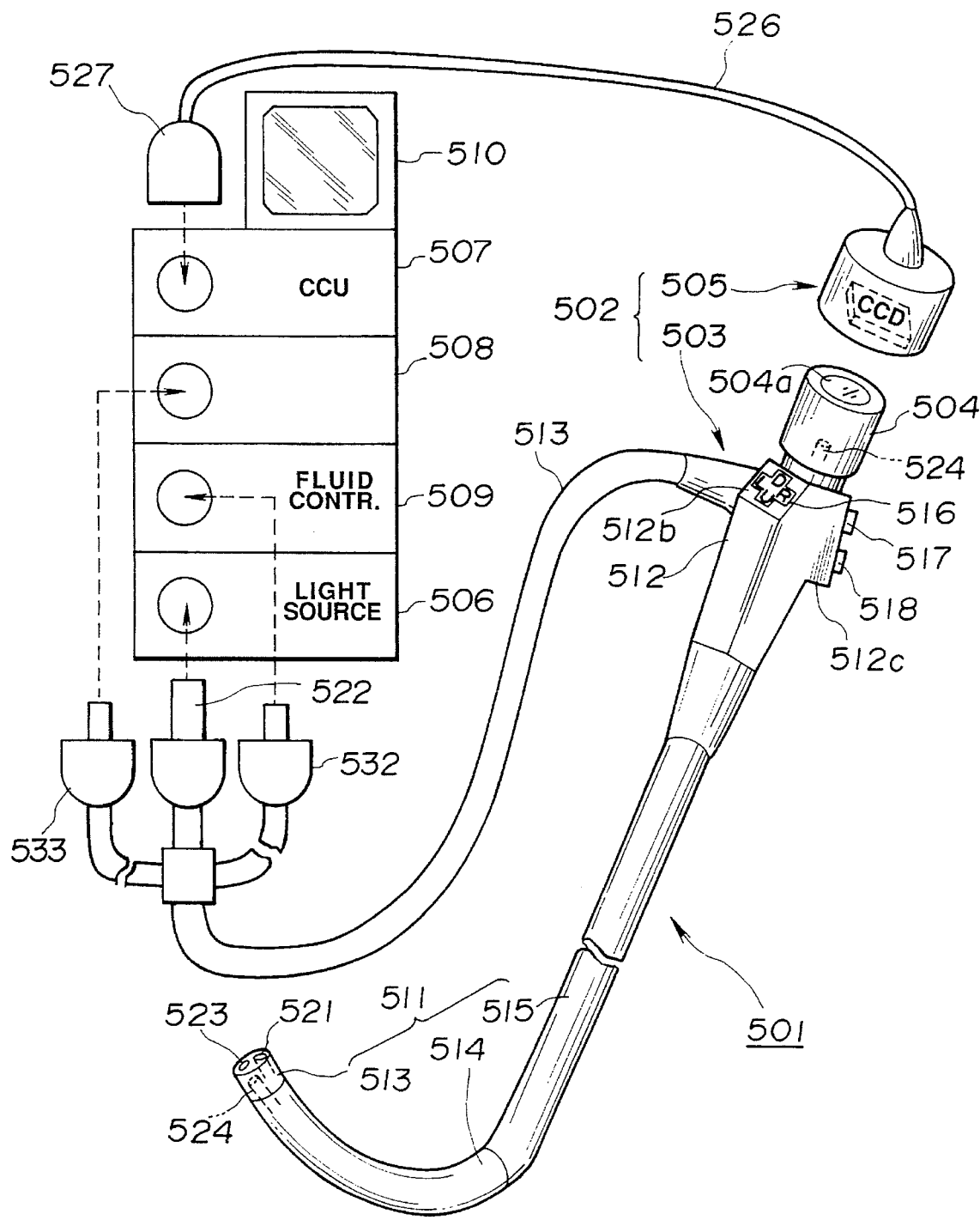
FIG. 48 is an entire or whole arrangement view showing an endoscope apparatus according to a thirteenth embodiment of the invention.

Furthermore, it is also possible to use a TV camera outside mounted scope in which a TV camera is mounted on a fiber scope in place of the electronic endoscope. FIG. 48 shows an endoscope apparatus 501 according to a thirteenth embodiment of the invention, which uses a TV camera outside mounted scope 502, in place of the electronic endoscope according to the first embodiment, for example.

The endoscope apparatus 501 comprises the TV camera outside mounted scope 502 in which a TV camera 505 is mounted on an ocular portion 504 of a fiber scope 503, a light source device 506 for supplying an illuminating light to the fiber scope 503, a camera control unit (a function thereof is the same as the VP 4, and the camera control unit will be referred simply to as "CCU") 507 for executing signal processing with respect to the TV camera 505, a curvature control device 508 provided with a curvature control mechanism, a hydraulic control device 509 provided with a control mechanism for fluid, and a color monitor 510 connected to the CCU 507, an image signal outputted from the CCU 507 being inputted to the color monitor 510 whereby the color monitor 510 displays an image of a subject image-picked-up.

The fiber scope 503 includes an elongated inserting section 511, a wide-width operating section 512 provided at a proximal end of the inserting section 511, an ocular section 504 provided at a rearward end of the operating section 512, and a light guide cable 513 extending from a side of the operating section 512.

Moreover, the inserting section 511 has a hard forward-end arrangement portion 513, a curvature portion 514 formed at a rearward end of the forward-end arrangement portion 513, and a flexible tube portion 515 formed at a rearward end of the curvature portion 514.

The inserting section 512 is provided with a curvature operating switch portion 516, a gas-feed/water-feed switch 517 and a suction switch 518 similar to those of the electronic endoscope 2' illustrated in FIG. 7, for example.

The operating section 512 is provided with an inclined-surface portion 512b and an antiskid projection 512c similarly to FIG. 7.

A light guide 521 has a forward end surface thereof which is mounted on an illuminating window of the forward-end arrangement portion 513. A light guide connector 522 of a light guide cable 513 is connected to the light source device 506, whereby the illuminating light is supplied from the lamp within the light source device 506.

The illuminating light is transmitted by the light guide 521, goes out forwardly from the end surface of the illuminating window, and illuminates the subject.

The illuminated subject focuses an optical image onto a focal surface by an objective lens 523 which is mounted on the observing window. The forward end surface of an image guide 524 is arranged on the focal surface. The optical image is transmitted to the other end surface adjacent to the ocular portion 504 by the image guide 524. The transmitted image is focused onto the CCD 525 through an ocular lens 504a and lenses of the TV camera 505, and is photoelectrically transferred. A signal therefrom is signal-processed by the fact that a connector 527 mounted on a distal end of the cable 526 of the TV camera 505 through a cable 526 of the TV camera 505 is connected to the CCU 507, is converted to a standard image signal, and is displayed by the color monitor 510.

The inserting section 511 is also provided with a gas-feed/water-feed line and a suction line. These lines are also inserted through the light guide cable 513, and reach a gas-feed/water-feed and suction connecter 532 at the distal end of the lines. The gas-feed/water-feed and suction connector 532 is connected to the fluid control device 509, whereby, in a case where the gas-feed/water-feed switch 517 and the suction switch 518 are operated, it is possible to execute turning-ON and -OFF of the gas-feed/water-feed and suction operations in accordance with the operation of the gas-feed/water-feed switch 517 and the suction switch 518.

Further, a signal line, a curvature wire and the like connected to the curvature operating switch portion 516 connect to a connector 533 at the distal end of the cable 513 to the curvature control device 508 through the light guide cable 513, whereby the curvature section 514 can be curved in accordance with operation of the curvature operating switch portion 516.

The apparatus 501 is arranged such that the TV camera outside mounted scope 502 is used in place of the electronic endoscope 2 according to the first embodiment, and the light source and fluid control device 3 is further separated into the light source device 506 and the fluid control device 509. Accordingly, various constitutional elements are basically the same in arrangement as those of the first embodiment, and the description thereof will be omitted.

In connection with the above, it is possible to partially combine the above-described various embodiments to form a different embodiment.

In the above-described embodiments, the basic configuration of the operating section in which the curvature indicating element and the fluid control operating element are arranged is a prismatic tubular element. However, if the object of the invention can be achieved, the configuration of the operating section may be a columnar tube element, a spherical configuration or the like.

We claim:

1. An endoscope comprising:

an elongated inserting section including a curvable curvature portion formed adjacent to a distal end of said inserting section, wherein said curvature portion is curvable in more than two directions;

illuminating-light outgoing means for projecting an illuminating light from said distal end of said inserting section;

an objective optical system formed at said distal end of said inserting section, for observing an object illuminated by said illuminating light;

a fluid line having an opening thereof formed adjacent to said distal end of said inserting section, for executing at least one function of outflow and inflow of fluid with respect to said opening:

an operating section formed at a proximal end of said inserting section, and provided with a grasping portion capable of being grasped by a hand of an operator:

a cross-pad having a plurality of touch-actuated pad sections for controlling curvature in a plurality of directions including one upward-direction curvature indicating touch-actuated pad section being disposed nearest the inserting section of the endoscope in said plurality of touch-actuated pad sections, said cross-pad being mounted on a first surface of said operating section for executing a curvature operation in an indicated direction selectable from said more than two directions to curve said curvature portion in said direction, wherein said upward-direction curvature indicating touch-actuated pad section indicates curving of said curvature portion in a direction corresponding to an upward direction of afield of view of said objective optical system, and wherein said first surface is inclined with respect to an adjacent surface of said grasping portion located on the same side of said operating section as said first surface;

at least one fluid control operating element arranged on a second surface of said operating section, and arranged at a position substantially opposed to said cross-pad mounted on said first surface for executing operation to control at least one function of the outflow and the inflow of said fluid;

detecting means for detecting whether or not said cross-pad and said fitlid control operating element are simultaneously operated and inhibiting means for inhibiting operation of said curvature section when said cross-pad is activated whenever said detecting means detects that said cross-pad and said fitlid control operating element are simultaneously operated.

2. An endoscope according to claim 1, including gas-feed and liquid-feed means connected to a proximal end of said fluid line for supplying gas and liquid to said distal end, and for causing the gas and the liquid to flow out from said opening.

3. An endoscope according to claim 2, wherein said fluid control operating element is a gas-feed and liquid-feed switch for controlling operation of said gas-feed and liquid-feed means.

4. An endoscope according to claim 1, including suction means connected to a distal end of said fluid line, for causing the gas and the liquid to flow in toward a side of said fluid line from said opening.

5. An endoscope according to claim 4, wherein said fluid control operating element is a suction switch for controlling operation of said suction means.

6. An endoscope according to claim 1, including curvature drive means for curving and driving said curvature portion.

7. All endoscope according to claim 1, wherein said endoscope is connected to separate curvature drive means for curving and driving said curvature portion.

8. An endoscope according to claim 1, wherein said endoscope includes switch means for switching correspondence between said plurality of directions and a curvature direction in which said curvature section is curved.

9. An endoscope according to claim 1, including control means for executing slow operation of said curvature section when said curvature direction indicating element is actuated after operation of said fluid control operating element has been completed whenever said detecting means detects that said curvature direction indicating means and said fluid control operating element are simultaneously operated.

10. An endoscope according to claim 1, wherein said cross-pad includes curvature direction indicating multi-stage ON/OFF switches for controlling the execution of said touch-activated pad sections by depression of said switches.

11. An endoscope according to claim 1, including a light guide cable extending from a third surface of said operating section located between said first surface and said second surface.

12. An endoscope according to claim 11, further including a projection provided on said second surface for reducing a slipping tendency.

13. An endoscope according to claim 1, further including a light guide cable, wherein said first surface of said operating section is substantially square-shaped, and wherein said cable extends from a third surface adjacent to said first surface on which said cross-pad is arranged, said third surface also being adjacent said second surface on which said fitlid control operating element is arranged.

14. An endoscope comprising:

an elongated inserting section including a curvable curvature portion formed adjacent to a distal end of said inserting section, wherein said curvature portion is curvable in more than two directions;

illuminating-light outgoing means for projecting an illuminating light from said distal end of said inserting section;

an objective optical system formed at said distal end of said inserting section, for observing an object illuminated by said illuminating light;

a fluid line having an opening thereof formed adjacent to said distal end of said inserting section, for executing at least one function of outflow and inflow of fluid with respect to said opening;

an operating section formed at a proximal end of said inserting section, and provided with a grasping portion capable of being grasped by a hand of an operator;

a cross-pad having a plurality of touch-actuated pad sections for controlling curvature in a plurality of directions including one upward-direction curvature indicating touch-actuated pad section being disposed nearest the inserting section of the endoscope in said plurality of touch-actuated pad sections, said cross-pad being mounted on a first surface of said operating section for executing a curvature operation in an indicated direction selectable from said more than two directions to curve said curvature portion in said direction, wherein said upward-direction curvature indicating touch-actuated pad section indicates curving of said curvature portion in a direction corresponding to an upward direction of afield of view of said objective optical system, wherein said first surface is inclined with respect to an adjacent surface of said grasping portion located on the same side of said operating section as said first surface, and wherein said cross-pad includes curvature direction indicating multi-stage ON/OFF switches for controlling the execution of said touch-actuated pad sections by depression of said switches;

at least one fluid control operating element arranged on a second surface of said operating section, and arranged at a position substantially opposed to said cross-pad mounted on said first surface section for executing operation to control at least one function of the outflow and the inflow of said fluid, a driving motor for driving said curvature portion; and a control portion supplying a small first amount of electrical current into said driving motor when a first stage of one of said multi-stage ON/OFF switches is ON, said control portion supplying a second amount of electrical current greater than said first amount of electrical current into said driving motor when a second stage of one of said multi-stage ON/OFF switches is ON.

* * * * *